United States Patent
Wright et al.

(10) Patent No.: US 10,226,532 B2
(45) Date of Patent: *Mar. 12, 2019

(54) COMPOSITIONS AND METHODS INVOLVING POLYMER, SOLVENT, AND HIGH VISCOSITY LIQUID CARRIER MATERIAL

(71) Applicant: DURECT CORPORATION, Cupertino, CA (US)

(72) Inventors: Jeremy C. Wright, Los Altos, CA (US); Wilma Tamraz, San Jose, CA (US); John J. Leonard, Morgan Hill, CA (US); John W. Gibson, Springville, AL (US); Keith E. Branham, Pelham, AL (US); Stefania Sjobeck, Glumsloev (SE); Brooks Boyd, Emeryville, CA (US); Christopher M. Rubino, Latham, NY (US)

(73) Assignee: DURECT CORPORATION, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/652,655

(22) Filed: Jul. 18, 2017

(65) Prior Publication Data

US 2018/0036412 A1 Feb. 8, 2018

Related U.S. Application Data

(63) Continuation of application No. 14/773,642, filed as application No. PCT/US2014/023397 on Mar. 11, 2014, now Pat. No. 9,737,605.

(60) Provisional application No. 61/824,827, filed on May 17, 2013, provisional application No. 61/798,874, filed on Mar. 15, 2013, provisional application No. 61/776,336, filed on Mar. 11, 2013.

(51) Int. Cl.

| | |
|---|---|
| *A61K 9/00* | (2006.01) |
| *A61M 5/20* | (2006.01) |
| *A61M 5/24* | (2006.01) |
| *A61M 5/30* | (2006.01) |
| *A61K 47/20* | (2006.01) |
| *A61K 47/22* | (2006.01) |
| *A61K 47/26* | (2006.01) |
| *A61M 5/315* | (2006.01) |
| *A61K 31/519* | (2006.01) |

(52) U.S. Cl.
CPC ............ *A61K 47/22* (2013.01); *A61K 9/0019* (2013.01); *A61K 9/0021* (2013.01); *A61K 31/519* (2013.01); *A61K 47/20* (2013.01); *A61K 47/26* (2013.01); *A61M 5/2033* (2013.01); *A61M 5/2046* (2013.01); *A61M 5/2053* (2013.01); *A61M 5/24* (2013.01); *A61M 5/30* (2013.01); *A61M 5/315* (2013.01); *A61M 2205/8206* (2013.01)

(58) Field of Classification Search
CPC ........ A61K 47/22; A61K 47/26; A61K 47/20; A61K 31/519; A61K 9/0021; A61K 9/0019; A61M 5/2046; A61M 5/2033; A61M 5/315; A61M 5/24; A61M 5/30; A61M 5/2053; A61M 2205/8206
See application file for complete search history.

(56) References Cited

U.S. PATENT DOCUMENTS

| | | |
|---|---|---|
| 4,530,840 A | 7/1985 | Tice et al. |
| 4,622,219 A | 11/1986 | Haynes |
| 4,725,442 A | 2/1988 | Haynes |
| 4,767,628 A | 8/1988 | Hutchinson |
| 4,891,225 A | 1/1990 | Langer |
| 4,906,474 A | 3/1990 | Langer |
| 4,938,763 A | 7/1990 | Dunn et al. |
| 4,957,744 A | 9/1990 | Della Valle et al. |
| 5,149,543 A | 9/1992 | Cohen et al. |
| 5,534,269 A | 7/1996 | Igari et al. |
| 5,643,605 A | 7/1997 | Cleland et al. |
| 5,747,058 A | 5/1998 | Tipton et al. |
| 5,871,778 A | 2/1999 | Kino |
| 5,968,542 A | 10/1999 | Tipton |

(Continued)

FOREIGN PATENT DOCUMENTS

| | | |
|---|---|---|
| EP | 0998917 | 5/2000 |
| EP | 1210942 | 6/2002 |

(Continued)

OTHER PUBLICATIONS

Lu et al. ("In vivo evaluation of risperidone-SAIB in situ system as a sustained release delivery system in rats", 2008) (Year: 2008).*

(Continued)

*Primary Examiner* — Robert A Wax
*Assistant Examiner* — Quanglong N Truong
(74) *Attorney, Agent, or Firm* — Greenblum & Bernstein, P.L.C.

(57) ABSTRACT

Compositions may include a pharmaceutical active agent, a high viscosity liquid carrier material (HVLCM), a lactic acid-based polymer, and an organic solvent. Related compositions and methods are also disclosed. For instance, a carrier formulation for controlled release of injectable drugs is disclosed. The formulation may include a non-water soluble high viscosity liquid which may be sucrose acetate isobutyrate, a lactic-acid based polymer which may be a poly(lactic acid)(glycolic acid), and an organic solvent which maintains the composition in a monophasic form at 25° C. in one atmosphere. Drug in the formulation may be released upon administration such that less than 10% (e.g. 2-8%) of drug is released in the first 5 hours; 10% to 80% of the drug is released during a period of 5 hours to 7 days after administration; and 10% to 40% of the drug is released gradually over a period of 7 days to 28 days from initial administration. The drug may be an anti-schizophrenia agent delivered by injection.

20 Claims, 41 Drawing Sheets

(56) References Cited

U.S. PATENT DOCUMENTS

| | | | |
|---|---|---|---|
| 6,130,200 | A | 10/2000 | Brodbeck et al. |
| 6,291,013 | B1 | 9/2001 | Gibson et al. |
| 6,331,311 | B1 | 12/2001 | Brodbeck et al. |
| 6,413,536 | B1 | 7/2002 | Gibson et al. |
| 6,468,961 | B1 | 10/2002 | Brodbeck et al. |
| 6,673,767 | B1 | 10/2004 | Brodbeck et al. |
| 6,956,059 | B2 | 10/2005 | Coupland |
| 7,820,202 | B2 | 10/2010 | Bodmeier |
| 7,824,700 | B2 | 11/2010 | Cleland |
| 7,833,543 | B2 | 11/2010 | Gibson et al. |
| 7,927,618 | B2 | 4/2011 | Bodmeier |
| 8,133,507 | B2 | 3/2012 | Yum et al. |
| 8,852,638 | B2 | 10/2014 | Luk et al. |
| 9,044,450 | B2 | 6/2015 | Luk et al. |
| 9,572,812 | B2 | 2/2017 | Wright et al. |
| 9,597,402 | B2 | 3/2017 | Luk et al. |
| 9,737,605 | B2 | 8/2017 | Wright et al. |
| 2002/0064547 | A1 | 5/2002 | Chern et al. |
| 2003/0009145 | A1 | 1/2003 | Struijker-Boudier et al. |
| 2004/0018238 | A1 | 1/2004 | Shukla |
| 2004/0101557 | A1* | 5/2004 | Gibson .......... A61K 8/60 424/484 |
| 2004/0161382 | A1 | 8/2004 | Yum et al. |
| 2004/0258731 | A1 | 12/2004 | Hayashi et al. |
| 2005/0079202 | A1 | 4/2005 | Chen et al. |
| 2005/0106214 | A1 | 5/2005 | Chen |
| 2007/0077304 | A1 | 4/2007 | Luk et al. |
| 2007/0108405 | A1 | 5/2007 | Khoo et al. |
| 2007/0196416 | A1 | 8/2007 | Chien et al. |
| 2008/0051700 | A1* | 2/2008 | Schuster .......... A61M 5/30 604/68 |
| 2008/0152708 | A1 | 6/2008 | Gibson et al. |
| 2008/0206321 | A1 | 8/2008 | Yum et al. |
| 2008/0287464 | A1* | 11/2008 | Wright .......... A61K 9/0019 514/259.41 |
| 2009/0023690 | A1 | 1/2009 | Yum et al. |
| 2009/0325879 | A1* | 12/2009 | Norton .......... A61K 9/0024 514/5.9 |
| 2010/0266655 | A1 | 10/2010 | Dadey |
| 2010/0292195 | A1 | 11/2010 | Dadey |
| 2013/0171202 | A1 | 7/2013 | Gutierro et al. |
| 2013/0289053 | A1 | 10/2013 | Wright et al. |
| 2014/0308352 | A1 | 10/2014 | Wright et al. |
| 2017/0143721 | A1 | 5/2017 | Wright et al. |
| 2017/0239252 | A1 | 8/2017 | Luk et al. |

FOREIGN PATENT DOCUMENTS

| | | |
|---|---|---|
| EP | 1649850 | 4/2006 |
| EP | 1317254 | 2/2007 |
| EP | 1248596 | 3/2007 |
| EP | 1940351 | 4/2012 |
| EP | 2529756 | 12/2012 |
| EP | 2361609 | 7/2013 |
| EP | 2167039 | 9/2016 |
| GB | 2165148 | 4/1986 |
| JP | S61-37725 | 2/1986 |
| JP | H04-056736 | 5/1992 |
| JP | H05-078634 | 3/1993 |
| JP | H09-315957 | 12/1997 |
| JP | 2001-509146 | 7/2001 |
| JP | 2001-516728 | 10/2001 |
| JP | 2003-063954 | 3/2003 |
| JP | 2004-511431 | 4/2004 |
| WO | 1998/27963 | 6/1998 |
| WO | 99/13913 | 5/1999 |
| WO | 00/24374 | 5/2000 |
| WO | 02/08351 | 1/2002 |
| WO | 2002/00137 | 1/2002 |
| WO | 2002/067895 | 9/2002 |
| WO | 2002/076344 | 10/2002 |
| WO | 2003/041684 | 5/2003 |
| WO | 2003/041685 | 5/2003 |
| WO | 2003/041757 | 5/2003 |
| WO | 2004/000269 | 12/2003 |
| WO | 2004/000395 | 12/2003 |
| WO | 2004/011054 | 2/2004 |
| WO | 2004/011065 | 2/2004 |
| WO | 2004/032980 | 4/2004 |
| WO | 2004/043432 | 5/2004 |
| WO | 2004/026357 | 9/2004 |
| WO | 2004/094414 | 11/2004 |
| WO | 2005/048989 | 6/2005 |
| WO | 2005/070332 | 8/2005 |
| WO | 2005/089670 | 9/2005 |
| WO | 2005/115346 | 12/2005 |
| WO | 2007/084460 | 1/2007 |
| WO | 2007/061896 | 5/2007 |
| WO | 2008/124013 | 10/2008 |
| WO | 2008/143992 | 11/2008 |
| WO | 2009/100222 | 2/2009 |
| WO | 2011/151355 | 12/2011 |
| WO | 2011/151356 | 12/2011 |
| WO | 2012/074883 | 6/2012 |
| WO | 2014/164754 | 10/2014 |

OTHER PUBLICATIONS

U.S. Appl. No. 14/658,072, filed Mar. 13, 2015, Yum, et al.
Berge, L., et al., "Pharmaceutical Salts", *J. of Pharmaceut. Sci.*, vol. 66:1 Jan. 1977 pp. 1-19.
Carraway KM, Meador SK, Sullivan SA, Gibson JW, Tipton AJ, Drug release from a controlled release aerosol: Effects of formulation variables Southern Biosystems, Inc., Birmingham, ALAAPS Indianapolis Nov. 2000.
Communication of a Notice of Opposition, Notice of Opposition and Opponents Grounds of Opposition, from EP 2361609, mailed May 7, 2014.
Desai, et al., "Surface modification of polymer biomaterials for reduced thrombogenicity", *Polym. Mater. Sci. Eng.* 63:731-735, 1991.
Dong, et al., "Development of injectable biodegradable in-situ forming gel implants", *Progress in Pharmaceutical Sciences*, 31:109-113. 2007.
Eliaz, et al., "Characterization of a polymeric PLGA-injectable implant delivery system for the controlled release of proteins", *J. Biomed. Mater. Res.* 2000, 50:388-396.
Erickson NM, Kines PP, Meador SK, Middleton JC, Williams CT, Williams JC, "An in vitro degradation study comparing poly(DL-lactide co-glycolide) with acid end groups and ester end groups", 20th Southern Biomedical Engineering Conference 2001.
English language translation of Office Action dated Jun. 15, 2012, from Japanese Application No. 2008-533726.
English Language translation of Japanese Office Action dated Apr. 14, 2015 for JP2013-002422.
Gomeni, R., et al., "A model-based approach to characterize the population pharmacokinetics and the relationship between the pharmacokinetic and safety profiles of RBP-7000, a new, long-acting, sustained-release formulation of Risperidone", *J. Clin. Pharmaco.* 58(10) 1010-1019 2013.
Hatefi, et al., "Biodegradable injectable in situ forming drug delivery system", *J. of Contr. Rel.* vol. 80, Jan. 1, 2002, pp. 9-28.
Hou H, etal., *China Med. Press* pp. 223-226, 2011.
Johnson CA, Thompson DL, Jr., Sullivan SA, Gibson JW, Tipton AJ, Simon BW, Burns PJ, "Biodegradable delivery systems for Estradiol: Comparison between Poly (DL-lactide) microspheres and the SABER delivery system", *Proceed Int 'l. Symp. Control. Rel. Bioact. Mater.*, 26 (1999), Controlled Release Society, Inc.
Kulkarni RK, et al., "Polylactic acid for surgical implants", *Arch. Surg.* vol. 93, Nov. 1966, 839-843.
Laffont, C., et al., "Population pharmacokinetic modeling and simulation to guide dose selection for RBP-7000, a new sustained-release formulation for Risperidone", *J. Clin. Pharma.* 55(1) 93-103 2014.
Laffont, C., et al., "Population pharmacokinetics and prediction of dopamine D2 Receptor occupancy after multiple doses of RBP-7000, a new sustained-release formulation of risperidone, in schizophrenia patients on stable oral risperidone treatment", *Clin. Pharmacokinetics*, 53:533-543 2014.
Lambert et al., Journal of Controlled Release, 1995 33:189-195.

(56) References Cited

OTHER PUBLICATIONS

Lin, et al., Á novel risperidone-loaded SAIB-PLGA mixture matrix depot with a reduced burst release: effect of solvents and PLGA on drug release behaviors in vitro/in vivo, *J. Mater. Sci.: Mater. Med.* (2012) 23:443-455.
Lu, Y., et al., "Sucrose Acetate Isobutyrate as an in situ forming system for sustained riperidone release", *J. Pharm. Sci.*, vol. 96, No. 12, Dec. 2007, 3252-3262.
Lu, Y., et al., "In vivo evaluation of risperidone-SAIB in situ system as a sustained release delivery system in rats", *Eur. J. Pharma and Biopharm.*, 68 (2007) 422-429.
Middleton, et al., Medical Device and Diagnostic Industry News Products and Suppliers 1998.
Middleton JC, Yarbrough JC, "The effect of PEG end groups on the degradation of a 75/25 poly(DL-lactide-co-glycolide", *Society for Biomaterials* 1999.
Okumu FW, Daugherty A, Dao LN, Fielder PJ, Brooks D, Sane S, Sullivan SA, Tipton AJ, Cleland JL, "Evaluation of the SABER TM delivery system for sustained release of growth hormone formulation design and in vivo assessment" 2001.
Okumu FW, Daugherty A, Sullivan SA, Tipton AJ, Cleland JL, "Evaluation of SABER TM as a local delivery system for rhVEGF-formulation design and in vitro assessment", 2000.
Okumu FW, Dao Le, Fielder PJ, Dybdal N, Brooks D, Sane S, Cleland JL, "Sustained delivery of human growth hormone from a novel gel system: SABER TM", *Biomaterials* 23 (2002) 4353-4358.
Opponent written submissions in patent No. EP2361609 dated Sep. 10, 2015 pp. 1-6.
Opposition Minutes and Opinion in patent No. EP2361609 dated Nov. 27, 2015 pp. 1-20.
Opponent's Grounds of Appeal in patent No. EP2361609 dated Mar. 29, 2016 pp. 1-13.
Patent owner's written submissions in patent No. EP2361609 dated Sep. 10, 2015 pp. 1-9.
Patent owner's Experimental Report in patent No. EP2361609 dated Aug. 18, 2015.
Summons to Oral Proceedings from European Patent Office in Opposition against EP patent No. 2361609 dated Feb. 16, 2015. pp. 1-6.
Patent owner's Written Submission in opposition against EP2361609 dated Nov. 19, 2014. pp. 1-10.
Penco M, et al., "A new chain extension reaction on poly(lactic-glycolic acid) (PLGA) thermal oligomers leading to high molecular weight PLGA-based polymeric products," *Polymer International*, 46:203-216, 1998.
Ravivarapu, et al., Journal of Pharmaceutical Sciences 89:732-741.
Shakeel, F., et al., "Solubility of antipsychotic drug risperidone in Transcutol + water co-solvent mixtures at 298.15 to 333.15 K", *J. of Molec. Liq.* 191 (2014) 68-72.
Sinha & Trehan, "Biodegradable Microspheres for Parenteral Delivery", *Critical Reviews in Therapeutic Drug Carrier Systems*, 22(6): 535-602 (2005).
Smith DA, Tipton AJ, "A novel parenteral delivery system", AAPS-Presentation TDD 7270 Annual Meeting, Seattle, WA (1996).
Sullivan SA, Yarbrough JC, Fengl RW, Tipton AJ, Gibson JW, "Sustained release of orally administered active using SABER TM delivery system incorporated into soft gelatin capsules", *Proceed. Int'l. Symo. Control. Rel. Bioact. Mater.*, 25 (1998), Controlled Release Society, Inc.
Sullivan SA, Meador SK, Carraway KM, Williams JC, Gibson JW, Tipton AJ, "Sustained release of lysozyme from the SABER delivery system", AAPS New Orleans, LA 1999.
Sullivan SA, Meador SK, Dodson KM, Williams JC, Gibson JW, Tipton AJ, "Sustained release of lysozyme from the SABER delivery system", Poster, Southern Biosystems, Inc. Birmingham AL AAPS New Orleans, LA 1999.
Sullivan SA, Meador SK, Dodson KM, Tipton AJ, Gibson JW, "Incorporation of polymer microparticles into sucrose acetate isobutyrate reduces burst and extends release", *Proceed. Int'l. Symp. Control. Rel. Bioact. Mater.*, 27, Controlled Release Society, Inc. (2000).
Tipton AJ, "Sucrose Acetate Isobutyrate (SAIB) for Parenteral Delivery", Reprinted from Modified-Release Drug Delivery Technology, Rathbone, Hadgraft, Roberts (Eds.), 2002 Marcel Dekker, Inc.
Wang, et al., "Drug release from injectable depots: two different in vitro mechanisms", *J. of Controlled Rel.*, 99, pp. 207-216, 2004.
Wang, et al., "Synthesis, characterization, biodegration, and drug delivery application of biodegradable lactic/glycolic acid polymers: I. Synthesis and characterization," *J. Biomater. Sci Polymer Edn*, vol. 11, No. 3, pp. 301-318 (2000).
Written Opinion of the International Searching Authority for International Application No. PCT/US2014/023397 dated Sep. 15, 2015.
Yapar, E., et al., "Injectable In Situ forming microparticles: A novel drug delivery system", *Tropical J. of Pharmaceut. Research*, 11(2) 307-318, Apr. 2012.
http://www.absorbables.com/technical/inherent_viscosity.html, published online 2013.
"Relday: First once-monthly subcutaneous risperidone for the management of schizophrenia," partnering overview, 2013.
Extracts from European Pharmacopoeia, 5$^{th}$ Ed., Jun. 15, 2004. pp. 5-7, 2374-2376.
Huang, et al., "Pharmacokinetics of the novel antipsychotic agent risperidone and the prolactin response in healthy subjects," *Clinical Pharmacology & Therapeutics*, 54(3), pp. 257-268. Sep. 1993.
Opponent's Further Submission in EP Patent No. 2361609, dated Mar. 6, 2017, pp. 1-14.
Patentee's Response to Grounds of Appeal in EP Patent No. 2361609, dated Aug. 12, 2016, pp. 1-53.
Sigma-Aldrich website "Amitriptyline hydrochloride" pp. 1-4.
Risperidone Product Information, Cayman Chemical, Ann Arbor, MI, p. 1.
Wang, et al., "Structure formation in injectable poly(lactide-co-glycolide) depots," *J. Control. Rel.*, 90, pp. 345-354, 2003.
Wright, Jeremy, "Experimental Report—In Vitro Release Profiles for Formulations containing Amitriptyline hydrochloride," submitted in European Patent No. 2,361,609, Aug. 10, 2016.

* cited by examiner

R139
Cumulative Release Rate of Risperidone

FIG. 16  R140
Cumulative Release Rate of Risperidone

FIG. 32

Base Structural Model for PO Dosing Only

| Parameter | Final Estimate | %SEM | Inter-individual Variability | %SEM |
|---|---|---|---|---|
| $T_{lag1}$ and $T_{lag2}$ (hr) | 0.323 | 0.73 | - | - |
| $K_{a,PO1}$ and $K_{a,PO2}$ (hr$^{-1}$) | 2.78 | 17.7 | 0.767 (87.6% CV) | 17.3 |
| CL/F (L/hr)$^a$ | 40.6 | 7.91 | 0.216 (46.5% CV) | 11.2 |
| $V_c$ and $V_{c_m}$ (L) | 103 | 5.00 | 0.0720 (26.9% CV) | 31.8 |
| $Cl_d$/F (L/hr) | 41.8 | 9.06 | - | - |
| $V_p$/F and $V_{p_m}$/F (L) | 41.5 | 8.54 | - | - |
| $E_h$ | 0.677 | 3.52 | 0.823 (logit transform) | 11.9 |
| $E_m$ | 0.439 | 2.77 | 0.267 (logit transform) | 43.5 |
| $CL_m$/F (L/hr) | 6.38 | 5.42 | 0.0600 (20.2% CV) | 14.2 |
| $CLd_m$/F (L/hr) | 4.88 | 27.9 | - | - |
| Residual Variability, $\sigma^2$ | 0.0252 (15.9% CV) | 14.4 | | |

Risperidone: $T1/2_\alpha = 0.447$, $T1/2_\beta = 2.71$

9-OH Risperidone: $T1/2_\alpha = 3.68$, $T1/2_\beta = 17.9$

FIG. 33

Base Structural Model for PO and SC Dosing

| Parameter | Final Estimate | %SEM | Inter-individual Variability | %SEM** |
|---|---|---|---|---|
| $T_{lag1}$ and $T_{lag2}$ (hr) | 0.323 | 0.73 | - | - |
| $K_{a,PO1}$ and $K_{a,PO2}$ (hr$^{-1}$) | 1.95 | 25.9 | 0.686 (82.8% CV) | 50.6 |
| CL/F (L/hr)$^a$ | 40.6 | 20.6 | 0.206 (45.4% CV) | 150 |
| $V_c$ and $V_{cm}$ (L) | 106 | 19.6 | 0.0479 (21.9% CV) | 67.7 |
| $Cl_d$/F (L/hr) | 38.0 | 65.0 | - | - |
| $V_p$/F and $V_{pm}$/F (L) | 39.8 | 29.4 | - | - |
| $F_h$ | 0.643 | 9.81 | 0.705 (logit transform) | 153 |
| $F_m$ | 0.446 | 19.4 | 0.105 (logit transform) | 271 |
| $CL_m$/F (L/hr) | 6.17 | 18.0 | 0.0477 (21.8% CV) | 67.7 |
| $Cl_{dm}$/F (L/hr) | 4.31 | 68.7 | - | - |
| $K_{a,SC1}$ (hr$^{-1}$) | 0.256 | 41.4 | 0.229 (47.9% CV) | 343 |
| $K_{a,SC2}$ and $K_{a,SC3}$ (hr$^{-1}$) | 0.00170 | 26.1 | 0.227 (47.6% CV) | 91.2 |
| FRC | 0.0264 | 19.8 | 0.171 (logit transform) | 93.6 |
| FRC2 | 0.734 | 16.9 | 0.822 (logit transform) | 102 |
| $T_{lag4}$ (hr) | 5.38 | 37.7 | 0.146 (38.2% CV) | 232 |
| $T_{lag9}$ (hr) | 175 | 3.22 | - | - |
| $F_{SC}$ | 1.95 | 25.9 | 0.0433 (20.8% CV) | 197 |
| $\sigma^2_{CCV\ parent}$ | 0.0439 (21.0% CV) | 16.8 | | |
| $\sigma^2_{CCV\ metabolite}$ | 0.0287 (16.9% CV) | 25.2 | | |

Structural Population PK Model – PO and SC Data

Note: To help with parameter estimation and identifiability, $V_c$ and $V_{c_m}$ were estimated using a single parameter assuming parent and metabolite distribute similarly (the same was done with $V_p$ and $V_{p_m}$)

COMPOSITIONS AND METHODS INVOLVING POLYMER, SOLVENT, AND HIGH VISCOSITY LIQUID CARRIER MATERIAL

CROSS-REFERENCED TO RELATED APPLICATIONS

The present application is a Continuation Application of U.S. application Ser. No. 14/773,642, filed Sep. 8, 2015, which is a National Stage of International Patent Application No. PCT/US2014/023397 filed Mar. 11, 2014, which claims priority to U.S. Provisional Application No. 61/824,827 filed May 17, 2013, U.S. Provisional Application No. 61/798,874 filed Mar. 15, 2013, U.S. Provisional Application No. 61/776,336 filed Mar. 11, 2013. The disclosures of U.S. application Ser. No. 14/773,642 and International Patent Application No. PCT/US2014/023397 are incorporated by reference herein in their entireties.

BACKGROUND OF THE INVENTION

Compositions that provide controlled delivery of pharmaceutical active agent offer several advantages. For instance, controlled delivery can reduce or obviate the need for repeated dosing. Further, biodegradable matrices for drug delivery are useful because they obviate the need to remove a drug-depleted device.

Noncompliance is prevalent with oral medications, e.g., in the treatment of schizophrenia and/or bipolar disorder. For instance, treatment of psychosis is very difficult. Patients cannot in general be relied upon to present for dosing or follow dosing instructions. It has also been established that the risk for relapse can substantially increase with noncompliant patients. Therefore, less complicated dosing and less frequent dosing is advantageous. Long-acting medications, e.g., antipsychotic medications, have several advantages over short-acting oral tablets or IM agents when administered, e.g., for the treatment of chronic schizophrenia and/or bipolar disorder, e.g., assurance of compliance resulting in fewer relapses and re-hospitalizations. By contrast, some of the current long-acting products (e.g., Risperdal Consta® long-acting injection) requires supplementation, e.g., with oral risperidone, both at the initiation of IM dosing and in the event of a missed dose, due to a 3-week lag between the time of dose administration and initiation of drug release.

All currently approved or development-stage, long-acting injections of antipsychotic drugs are administered intramuscularly, which is associated with the disadvantages of injection site pain and, for this class of drug, the more significant potential safety issue of inadvertent vascular contact resulting in systemic exposure of toxic levels of drug. This issue was most recently manifested during the development of Zyprexa® (olanzapine) long-acting-injection in which excessive sedation and even incidences of coma have been observed post injection. In contrast, dosage forms that have the potential for subcutaneous (SC) administration mitigate this potential safety issue.

As noted above, intramuscular dosing is in general painful, and requires a very large needle. For example, paliperidone palmitate (tradename Invega Sustenna) requires a needle that is 1" long for patients <90 kg, and 1.5" long for patient more than 90 kg. This can cause distress, especially in a psychotic patient, and can lead to difficulty in dosing and lack of compliance. Therefore, subcutaneous dosing is preferred.

Some long-acting therapies require a loading dose when the therapy is initiated to achieve a good release profile. A loading dose is an extra dose that is given early in a treatment regimen to compensate for inadequate control over plasma level before a sustained release formulation achieves steady state. Loading doses may be delivered orally or by injection. Loading doses are undesirable, especially in psychotic patients, as they may lead to additional anxiety, agitation, or lack of compliance with therapy. An example of a therapy requiring a loading dose is paliperidone palmitate (tradename Invega Sustenna). For paliperidone palmitate, one week after an initial injection, the patient is often given a further injection before transitioning to once a month dosing.

There remains, however, a need for compositions and methods that provide reproducible, controlled delivery of pharmaceutical active agents with low toxicity. Accordingly, there also remains a need for methods of making these compositions that provide reproducible, controlled delivery of pharmaceutical active agents with low toxicity.

SUMMARY OF THE INVENTION

Certain non-limiting aspects of the disclosure are provided below:

1. A composition comprising:
   25 wt % to 80 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere;
   a lactic-acid based polymer that is poly(lactic acid)(glycolic acid) comprising an alkoxy end group, the poly(lactic acid)(glycolic acid) having a lactic acid to glycolic acid molar ratio greater than 65:35; and
   an organic solvent.
2. The composition of aspect 1, wherein the lactic-acid based polymer has a weight average molecular weight ranging from 1000 Daltons to 30,000 Daltons.
3. The composition of any one of aspects 1 and 2, wherein the lactic-acid based polymer has a weight average molecular weight ranging from 4000 Daltons to 15,000 Daltons.
4. The composition of any one of aspects 1 to 3, wherein the poly(lactic acid)(glycolic acid) has a lactic acid to glycolic acid molar ratio of at least 70:30.
5. A composition comprising:
   25 wt % to 80 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere;
   a lactic acid-based polymer comprising an alkoxy end group, wherein the lactic acid-based polymer has a weight average molecular weight ranging from 5000 Daltons to 30,000 Daltons, 6000 Daltons to 30,000 Daltons, or 7000 Daltons to 30,000 Daltons; and
   an organic solvent.
6. The composition of aspect 5, wherein the lactic acid-based polymer has a weight average molecular weight ranging from 5000 Daltons to 15,000 Daltons, 6000 Daltons to 15,000 Daltons, or 7000 Daltons to 15,000 Daltons.
7. The composition of any one of aspects 1 to 6, wherein the composition further comprises a pharmaceutical active agent.

8. A composition comprising:
   a pharmaceutical active agent;
   25 wt % to 80 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere;
   a lactic acid-based polymer comprising an alkoxy end group; and
   an organic solvent.

9. A composition comprising:
   particles comprising pharmaceutical active agent, the particles having a median particle size, as measured by laser diffraction, ranging from 0.5 micrometers to 10 micrometers or from 0.2 micrometers to 10 micrometers;
   25 wt % to 80 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere;
   a lactic acid-based polymer; and
   an organic solvent.

10. A gamma-irradiated composition comprising:
    pharmaceutical active agent; and
    wherein the gamma-irradiated composition further comprises:
    25 wt % to 80 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere;
    a lactic acid-based polymer; and
    an organic solvent.

11. The composition of any one of aspects 8 to 10, wherein the lactic-acid based polymer has a weight average molecular weight ranging from 1000 Daltons to 30,000 Daltons.

12. The composition of any one of aspects 8 to 11, wherein the lactic-acid based polymer has a weight average molecular weight ranging from 4000 Daltons to 15,000 Daltons.

13. The composition of any one of aspects 7 to 12, wherein the pharmaceutical active agent has a solubility in the composition at 25° C. of less than about 10 mg/ml.

14. The composition of any one of aspects 7 to 13, wherein the pharmaceutical active agent comprises at least one member selected from peptide, protein, antibody, carbohydrate, small molecule, nucleic acid, and nucleoside.

15. The composition of any one of aspects 7 to 14, wherein the pharmaceutical active agent comprises an antipsychotic, exenatide, or GLP-1.

16. The composition of any one of aspects 7 to 15, wherein the pharmaceutical active agent comprises an atypical antipsychotic.

17. The composition of any one of aspects 7 to 16, wherein the pharmaceutical active agent comprises at least one member selected from chlorpromazine, fluphenazine, mesoridazine, perphenazine, prochlorperazine, promazine, thioridazine, sulforidazine, trifluoperazine, molindone, azaperone, benperidol, droperidol, haloperidol, flupentixol, chlorprothixene, thiothixene, zuclopenthixol, fluspirilene, penfluridol, pimozide, loxapine, melperone, sertindole, ziprasidone, sulpiride, remoxipride, amisulpride, clozapine, olanzapine, quetiapine, aripiprazole, risperidone, paliperidone, zotepine, amisulpride, asenapine, iloperidone, lurasidone, cannabidiol, tetraenazine, and L-theanine, or pharmaceutically acceptable salt thereof, or pharmaceutically acceptable ester thereof.

18. The composition of any one of aspects 7 to 17, wherein the pharmaceutical active agent comprises risperidone or pharmaceutically acceptable salt thereof or pharmaceutically acceptable ester thereof.

19. A composition comprising:
    a pharmaceutical active agent that is risperidone or pharmaceutically acceptable salt thereof;
    a non-polymeric, non-water soluble high viscosity liquid carrier material (HVLCM) having a viscosity of at least 5000 cP at 37° C. that does not crystallize neat at 25° C. and 1 atmosphere, a lactic acid-based polymer comprising an alkoxy end group, and an organic solvent in a ratio sufficient to maintain a therapeutically effective plasma concentration of the risperidone or pharmaceutically acceptable salt thereof for a period of at least 7 days when the composition is administered subcutaneously as a single dose to a human patient.

20. The composition of aspect 19, wherein the period is at least 14 days.

21. The composition of aspect 19, wherein the period is at least 21 days.

22. The composition of aspect 19, wherein the period is at least 28 days.

23. A composition comprising:
    a pharmaceutical active agent that is risperidone or pharmaceutically acceptable salt thereof;
    a non-polymeric, non-water soluble high viscosity liquid carrier material (HVLCM) having a viscosity of at least 5000 cP at 37° C. that does not crystallize neat at 25° C. and 1 atmosphere, a lactic acid-based polymer comprising an alkoxy end group, and an organic solvent in a ratio such that when the composition is administered subcutaneously as a single dose to a human patient, an amount of pharmaceutical active agent released from the composition provides an AUC (0 to 1 day) that is less than 10%, such as less than 5%, of AUC (0 to 28 days).

24. The composition of any one of aspects 19 to 23, wherein the lactic-acid based polymer has a weight average molecular weight ranging from 1000 Daltons to 30,000 Daltons.

25. The composition of any one of aspects 19 to 24, wherein the lactic-acid based polymer has a weight average molecular weight ranging from 4000 Daltons to 15,000 Daltons.

26. The composition of any one of aspects 7 to 25, wherein the pharmaceutical active agent comprises particles having a median particle size, as measured by laser diffraction, ranging from 0.1 micrometer to 100 micrometers.

27. The composition of any one of aspects 7 to 26, wherein the pharmaceutical active agent comprises particles having a median particle size, as measured by laser diffraction, ranging from 0.5 micrometer to 10 micrometers.

28. The composition of any one of aspects 7 to 27, wherein the pharmaceutical active agent comprises particles having a median particle size, as measured by laser diffraction, ranging from 0.5 micrometer to 7 micrometers.

29. The composition of any one of aspects 7 to 28, wherein the pharmaceutical active agent is present in an amount ranging from 1 wt % to 50 wt %, based on total weight of the composition.
30. The composition of any one of aspects 1 to 29, wherein the HVLCM is present in an amount ranging from 30 wt % to 60 wt %, based on total weight of the composition.
31. The composition of any one of aspects 1 to 30, wherein the HVLCM comprises at least one member selected from sucrose acetate isobutyrate, a stearate ester, propylene glycol, glyceryl, diethylaminoethyl, glycol, a stearate amide, a long-chain fatty acid amide, N,N'-ethylene distearamide, stearamide monoethanolamine (MEA), stearamide diethanolamine (DEA), ethylene bistearamide, cocoamine oxide, a long-chain fatty alcohol, cetyl alcohol, stearyl alcohol, long-chain ester, myristyl myristate, beheny erucate, a glyceryl phosphate, and acetylated sucrose distearate.
32. The composition of any one of aspects 1 to 31, wherein the HVLCM comprises sucrose acetate isobutyrate.
33. The composition of any one of aspects 1 to 32, wherein the lactic acid-based polymer is present in an amount ranging from 1 wt % to 50 wt %, based on total weight of the composition.
34. The composition of any one of aspects 1 to 33, wherein the lactic acid-based polymer is present in an amount ranging from 5 wt % to 30 wt %, based on total weight of the composition.
35. The composition of any one of aspects 1 to 34, wherein the solvent comprises a hydrophilic solvent.
36. The composition of any one of aspects 1 to 35, wherein the solvent has a solvent capacity of greater than 20%.
37. The composition of any one of aspects 1 to 36, wherein the solvent comprises at least one member selected from N-methyl-pyrrolidone (NMP), dimethylsulfoxide (DMSO), propylene carbonate (PC), benzyl alcohol (BA), benzyl benzoate (BB), dimethylacetamide, caprylic/capric triglyceride, polyoxyethylene ester of 12-hydroxystearic acid, ethanol, ethyl lactate, glycofurol, propylene glycol, acetone, methyl acetate, ethyl acetate, methyl ethyl ketone, triacetin, dimethylformamide, tetrahydrofuran, caprolactam, decylmethylsulfoxide, oleic acid, tocopherol, linoleic acid, oleic acid, ricinoleic acid, pyrrolidone, diethyl phthalate, isopropylidene glycerol, and 1-dodecylazacycloheptan-2-one.
38. The composition of any one of aspects 1 to 37, wherein the solvent comprises at least one member selected from N-methyl-pyrrolidone (NMP), dimethylsulfoxide (DMSO), propylene carbonate (PC), benzyl benzoate (BB), dimethylacetamide, caprylic/capric triglyceride, polyoxyethylene ester of 12-hydroxystearic acid, ethanol, ethyl lactate, glycofurol, propylene glycol, acetone, methyl acetate, ethyl acetate, methyl ethyl ketone, triacetin, dimethylformamide, tetrahydrofuran, caprolactam, decylmethylsulfoxide, oleic acid, tocopherol, linoleic acid, oleic acid, ricinoleic acid, pyrrolidone, diethyl phthalate, isopropylidene glycerol, and 1-dodecylazacycloheptan-2-one.
39. The composition of any one of aspects 1 to 38, wherein the solvent comprises N-methyl-pyrrolidone.
40. The composition of any one of aspects 1 to 39, wherein the solvent comprises DMSO.
41. The composition of any one of aspects 1 to 40, wherein the solvent comprises propylene carbonate.
42. The composition of any one of aspects 1 to 41, wherein the solvent is present in an amount ranging from 10 wt % to 60 wt %, based on total weight of the composition.
43. The composition of any one of aspects 1 to 42, wherein the solvent is present in an amount ranging from 10 wt % to 40 wt %, based on total weight of the composition.
44. The composition of any one of aspects 4 to 43, wherein the lactic acid-based polymer comprises a homopolymer.
45. The composition of any one of aspects 4 to 44, wherein the lactic acid-based polymer comprises a copolymer.
46. The composition of any one of aspects 4 to 45, wherein the lactic acid-based polymer comprises poly (lactic acid)(glycolic acid).
47. The composition of aspect 46, wherein the poly(lactic acid)(glycolic acid) has a lactic acid to glycolic acid molar ratio ranging from 100:0 to 40:60.
48. The composition of aspect 46, wherein the poly(lactic acid)(glycolic acid) has a lactic acid to glycolic acid molar ratio ranging from 95:5 to 60:40.
49. A composition comprising:
    5 wt % to 20 wt %, based on total weight of the composition, of particles comprising pharmaceutical active agent that is risperidone or pharmaceutically acceptable salt thereof, the particles having a median particle size, as measured by laser diffraction, ranging from 0.5 micrometer to 7 micrometers;
    30 wt % to 60 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere, wherein the HVLCM is sucrose acetate isobutyrate;
    5 wt % to 30 wt %, based on total weight of the composition, of a lactic acid based-polymer that is poly(lactic acid)(glycolic acid) comprising an alkoxy end group, the poly(lactic acid)(glycolic acid) having a lactic acid to glycolic acid molar ratio ranging from 95:5 to 60:40, the poly(lactic acid)(glycolic acid) having a weight average molecular weight ranging from 4000 Daltons to 15,000 Daltons; and
    10 wt % to 50 wt % or 10 wt % to 40 wt %, based on total weight of the composition, of a solvent that is at least one member selected from N-methyl-pyrrolidone, propylene carbonate, and dimethylsulfoxide.
50. The composition of any one of aspects 1 to 49, which is a gamma-irradiated composition.
51. The composition of aspect 50, wherein after storage for 150 days at 37° C., the weight average molecular weight of the lactic acid-based polymer of the gamma-irradiated composition is at least 90% of the weight average molecular weight of the lactic acid-based polymer of an otherwise identical composition that is not gamma-irradiated before being stored for 150 days at 37° C.
52. The composition of aspect 50, wherein the weight average molecular weight of the lactic acid-based polymer of the composition after storage for 150 days at 37° C. is at least 50% of the weight average molecular weight of the lactic acid-based polymer immediately before gamma radiation.

53. The composition of any one of aspects 1 to 52, wherein a weight ratio of the HVLCM to the lactic acid-based polymer to the solvent ranges from 1:0.25-0.5:0.4-0.8.
54. The composition of any one of aspects 1 to 53, wherein the HVLCM, the lactic acid-based polymer, and the solvent are monophasic when stored at 25° C. for 7 days.
55. The composition of any one of aspects 1 to 54, wherein the HVLCM, the lactic acid-based polymer, and the solvent are monophasic when stored at 25° C. for 1 month.
56. The composition of any one of aspects 1 to 55, wherein the composition has a viscosity of less than 5000 cP at a shear rate of 50 $s^{-1}$ at 25° C.
57. The composition of any one of aspects 1 to 56, wherein the composition has a viscosity of less than 3000 cP at a shear rate of 100 $s^{-1}$ at 25° C.
58. The composition of any one of aspects 1 to 57, wherein the composition has a viscosity ranging from 50 cP to 2000 cP at a shear rate of 150 $s^{-1}$ at 25° C.
59. The composition of any one of aspects 1 to 58, wherein the composition has a viscosity ranging from 500 cP to 1500 cP at a shear rate of 200 $s^{-1}$ at 25° C.
60. The composition of any one of aspects 1 to 59, wherein the composition further comprises at least one member selected from viscosity enhancers, antioxidants, preservatives, and particle stabilizers.
61. The composition of any one of aspects 1 to 60, wherein the composition further comprises at least one member selected from ricinoleic acid and polyoxyethylene-polyoxypropylene block copolymer.
62. The composition of any one of aspects 1 to 61, wherein the composition comprises a pharmaceutical active agent and wherein when 2 mL of the composition is placed in an upright 2 mL vial for 10 months at 5° C., a difference between top concentration and bottom concentration divided by initial concentration is less than 35%,
    wherein the top concentration is concentration of pharmaceutical active agent of the top 10% of the composition within the upright 2 mL vial after the 10 months storage,
    wherein the bottom concentration is concentration of pharmaceutical active agent of the bottom 10% of the composition within the upright 2 mL vial after the 10 months storage, and
    wherein the initial concentration is concentration of pharmaceutical active agent of the composition before the 10 months storage.
63. The composition of aspect 62, wherein the difference between top concentration and bottom concentration divided by initial concentration is less than 15%.
64. The composition of aspect 62, wherein the difference between top concentration and bottom concentration divided by initial concentration is less than 10%.
65. The composition of any one of aspects 1 to 64, wherein the composition comprises a pharmaceutical active agent and wherein when the composition is administered subcutaneously as a single dose, a median amount of pharmaceutical active agent released from the composition at 4 weeks of administration to a human patient ranges from 20% to 100% or 20% to 75% of a total amount of the pharmaceutical active agent in the composition when administered.
66. The composition of any one of aspects 1 to 65, wherein the composition comprises a pharmaceutical active agent and wherein when the composition is placed in phosphate buffered saline at 37° C., an amount of pharmaceutical active agent released from the composition at 4 weeks of placement in the phosphate buffered saline ranges from 20% to 100% of a total amount of the pharmaceutical active agent in the composition.
67. The composition of any one of aspects 1 to 66, wherein the composition comprises a pharmaceutical active agent and wherein when the composition is administered subcutaneously as a single dose to a human patient, a median amount of pharmaceutical active agent released from the composition provides an AUC (0 to 1 day) that is less than 20% of AUC (0 to 28 days).
68. The composition of aspect 67, wherein when the composition is administered subcutaneously as a single dose to a human patient, a median amount of pharmaceutical active agent released from the composition provides an AUC (0 to 1 day) that is less than 10% of AUC (0 to 28 days).
69. The composition of any one of aspects 1 to 68, wherein the composition comprises a pharmaceutical active agent and wherein when the composition is administered subcutaneously as a single dose to a human patient, a median amount of pharmaceutical active agent released from the composition provides an AUC (0 to 1 day) that is less than 10% of AUCinf.
70. The composition of any one of aspects 1 to 69, wherein the composition comprises a pharmaceutical active agent and wherein when the composition is placed in phosphate buffered saline at 37° C., an amount of pharmaceutical active agent released from the composition at 24 hours after placement in the phosphate buffered saline is less than 10% of an amount released at 28 days.
71. The composition of aspect 70, wherein the amount of pharmaceutical active agent released at 28 days after placement in the phosphate buffered saline at 37° C. is greater than 30% or greater than 50% of a total amount of pharmaceutical active agent in the composition.
72. The composition of any one of aspects 1 to 71, wherein the lactic acid-based polymer comprises an alkoxy end group that consists of 8 to 24 carbons.
73. The composition of aspect 72, wherein the alkoxy end group consists of 12 carbons.
74. The composition of any one of aspects 9 and 10, wherein the lactic acid-based polymer is initiated with a member selected from fatty alcohol and diol.
75. The composition of any one of aspects 9 and 10, wherein the lactic-acid based polymer is initiated with 1,6-hexanediol.
76. The composition of any one of aspects 9 and 10, wherein the lactic-acid based polymer is initiated with dodecanol.
77. A composition comprising:
    a pharmaceutical active agent that is risperidone or pharmaceutically acceptable salt thereof;
    means for extending a release profile of the pharmaceutical active agent when the composition is administered to a patient in need thereof.
78. A composition comprising:
    a pharmaceutical active agent that is risperidone or pharmaceutically acceptable salt thereof;
    means for reducing settling of the pharmaceutical active agent within the composition.

79. A unit dosage form comprising the composition of any one of aspects 1 to 78, wherein the composition comprises a pharmaceutical active agent and wherein the unit dosage form comprises from 10 mg to 500 mg of the pharmaceutical active agent.
80. The unit dosage form of aspect 79, wherein the composition is contained within a vial.
81. The unit dosage form of aspect 79, wherein the composition is contained within a syringe.
82. The unit dosage form of aspect 79, wherein the composition is contained within a needle-free injector.
83. A receptacle containing the composition of any one of aspects 1 to 78, wherein the composition comprises a pharmaceutical active agent.
84. A needle-free injector comprising the composition of any of aspects 1 to 78, wherein the composition comprises a pharmaceutical active agent.
85. The needle-free injector of aspect 84 wherein the needle-free injector further comprises a drug capsule.
86. The needle-free injector of aspect 85, wherein the drug capsule is transparent.
87. The needle-free injector of any one of aspects 85 and 86, wherein the drug capsule is closed at one end by a piston.
88. The needle-free injector of aspect 87, wherein the piston comprises a polymer.
89. The needle-free injector of aspect 87, wherein the piston comprises polytetrafluoroethylene.
90. The needle-free injector of any one of aspects 85 and 87 to 89, wherein the drug capsule is at least partly transparent.
91. The needle-free injector of any one of aspects 85 to 90, wherein the drug capsule comprises glass.
92. The needle-free injector of any one of aspects 85 to 88, wherein the drug capsule comprises a clear polymer.
93. The needle-free injector of any one of aspects 88 to 92, wherein the transparent portion of the drug capsule does not change color when gamma-irradiated.
94. The needle-free injector of aspect 91, wherein the glass comprises borosilicate glass.
95. The needle-free injector of aspect 91, wherein the glass has undergone ion exchange strengthening.
96. The needle-free injector of any one of aspects 85 to 95, wherein the drug capsule is prefilled.
97. The needle-free injector of any one of aspects 84 to 96, wherein the needle-free injector is single use and disposable.
98. The needle-free injector of any one of aspects 84 to 97, wherein the drug capsule comprises at least one injection orifice.
99. The needle-free injector of aspect 98, wherein the at least one injection orifice is closed during storage by a sealing element.
100. The needle-free injector of aspect 99, wherein the sealing element is held rigidly to the injection orifice by a seal carrier.
101. The needle-free injector of aspect 100, wherein the seal carrier must be removed prior to use.
102. The needle-free injector of aspect 101, wherein the seal carrier is connected to the drug capsule by at least one element selected from:
    a frangible connection,
    a screw connection,
    a bayonet connection, and
    a luer connection.
103. The needle-free injector of any one of aspects 84 to 102, further comprising a triggering mechanism.
104. The needle-free injector of aspect 103, wherein the triggering mechanism is activated by pressing the at least one injection orifice against the target injection surface.
105. The needle-free injector of any one of aspects 84 to 104, further comprising a safety mechanism that ensures that the device cannot be actuated prematurely.
106. The needle-free injector of aspect 105, wherein the safety mechanism ensures that the device cannot be actuated until after removal of the seal carrier.
107. The needle-free injector of any one of aspects 84 to 106, further comprising a self-contained energy source.
108. The needle-free injector of aspect 107, wherein the self-contained energy source comprises at least one member selected from:
    a compressed mechanical spring,
    a compressed gas,
    a pyrotechnic charge, and
    a battery.
109. The needle-free injector of any one of aspects 107 and 108, further comprising a ram which upon activation of the triggering mechanism, under the urging of the energy source, traverses a gap and subsequently strikes the piston, creating a pressure spike in the composition.
110. The needle-free injector of aspect 109, wherein the urging of the energy source, the mass of the ram, the length of the gap, the mechanical properties of the piston, and the size of the orifice are selected such that in use, more than 90% of injections inject more than 90% of the composition subcutaneously.
111. A method of reducing phase separation, comprising combining:
    a pharmaceutical active agent,
    a non-polymeric, non-water soluble high viscosity liquid carrier material (HVLCM) having a viscosity of at least 5000 cP at 37° C. that does not crystallize neat at 25° C. and 1 atmosphere;
    a lactic acid-based polymer; and
    an organic solvent;
    thereby providing a composition as defined in any one of aspects 1 to 78 and that contains a pharmaceutical active agent.
112. A method of reducing phase separation, comprising combining:
    a pharmaceutical active agent with a means for achieving the reduction of phase separation.
113. The method of aspect 112, wherein the pharmaceutical active agent comprises risperidone or a pharmaceutically acceptable salt thereof.
114. The method of any one of aspects 112 and 113, wherein the pharmaceutical active agent comprises particles having a median particle size, as measured by laser diffraction, ranging from 0.2 micrometer or 7 micrometers or 0.5 micrometer to 7 micrometers.
115. A method of improving reproducibility of a release profile, comprising combining:
    a pharmaceutical active agent,
    a non-polymeric, non-water soluble high viscosity liquid carrier material (HVLCM) having a viscosity of at least 5000 cP at 37° C. that does not crystallize neat at 25° C. and 1 atmosphere;
    a lactic acid-based polymer; and
    an organic solvent;
    thereby providing a composition as defined in any one of aspects 1 to 78 and that contains a pharmaceutical active agent.

116. A method of administering a pharmaceutical active agent comprising:
administering an effective amount of a composition as defined in any one of aspects 1 to 78 and that contains a pharmaceutical active agent to a patient in need thereof.

117. The method of aspect 116, wherein the composition comprises from 0.1 mg to 500 mg of the pharmaceutical active agent.

118. The method of any one of aspects 116 and 117, wherein the composition is administered in an amount ranging from 0.05 mL to 10 mL.

119. The method of any one of aspects 116 to 118, wherein the pharmaceutical active agent and any metabolites thereof have a plasma level in the patient is at least 5 ng/mL at 28 days after administration.

120. The method of any one of aspects 116 to 119, wherein the Cmax of the pharmaceutical active agent ranges from 5 ng/mL to 300 ng/mL.

121. The method of any one of aspects 116 to 120, wherein the Cmax to Cmin ratio of the pharmaceutical active agent, as measured over 28 days after administration, ranges from 2 to 40.

122. The method of any one of aspects 116 to 121, wherein the Cmax to Cmin ratio of the pharmaceutical active agent, as measured over 21 days after administration, ranges from 2 to 40.

123. The method of any one of aspects 116 to 122, wherein the Cmax to Cmin ratio of the pharmaceutical active agent, as measured over 14 days after administration, ranges from 2 to 40.

124. The method of any one of aspects 116 to 123, wherein an amount of pharmaceutical active agent delivered into plasma at 24 hours of subcutaneous administration ranges from 0.5% to 15% of a total amount of the pharmaceutical active agent administered.

125. The method of any one of aspects 116 to 124, wherein an amount of pharmaceutical active agent delivered into plasma at 4 weeks of subcutaneous administration ranges from 20% to 100% or 20% to 75% of a total amount of the pharmaceutical active agent administered.

126. The method of any one of aspects 116 to 125, wherein an amount of pharmaceutical active agent delivered into plasma at 24 hours of subcutaneous administration divided by an amount of pharmaceutical active agent delivered at 4 weeks of administration ranges from 0.05 to 0.15.

127. The method of any one of aspects 116 to 126, wherein the administering comprises administering the composition subcutaneously.

128. The method of any one of aspects 116 to 127 wherein the pharmaceutical active agent is an anti-schizophrenia agent and the method is a method of treating at least one of schizophrenia and bipolar disorder.

129. The method of aspect 128, wherein the anti-schizophrenia agent comprises risperidone or pharmaceutically acceptable salt thereof.

130. A process comprising:
wet milling a pharmaceutical active agent in an aqueous solution at less than 20° C. to form a milled pharmaceutical active agent;
maintaining the milled pharmaceutical active agent at less than 5° C.; and
lyophilizing the milled pharmaceutical active agent to form a lyophilized pharmaceutical active agent having a median particle size, as measured by laser diffraction, of less than 5 micrometers.

131. The process of aspect 130, wherein the median particle size is less than 3 micrometers.

132. The process of aspect 130, wherein the median particle size is less than 2 micrometers.

133. A suspension produced by:
wet milling a pharmaceutical active agent in an aqueous solution at less than 20° C. to form a milled pharmaceutical active agent;
maintaining the milled pharmaceutical active agent at less than 5° C.; and
lyophilizing the milled pharmaceutical active agent to form a lyophilized pharmaceutical active agent having a median particle size, as measured by laser diffraction, of less than 5 micrometers.

134. The suspension of aspect 133, wherein the median particle size is less than 3 micrometers.

135. The suspension of aspect 133, wherein the median particle size is less than 2 micrometers.

136. A monophasic composition, comprising:
25 wt % to 80 wt %, based on total weight of the composition, of sucrose acetate isobutyrate;
a poly(lactic acid)(glycolic acid) comprising an alkoxy end group wherein the alkoxy end group consists of 12 carbons, the poly(lactic acid)(glycolic acid) having a lactic acid to glycolic acid molar ratio of at least 70:30; and
an organic solvent that maintains the composition monophasic at 25° C. and 1 atmosphere.

137. A composition as defined in any one of aspects 1 to 78 and that contains a pharmaceutical active agent, for use as a medicament.

138. A composition as defined in any one of aspects 1 to 78 and that contains a pharmaceutical active agent that is an anti-schizophrenia agent, for use in a method of treating at least one of schizophrenia and bipolar disorder.

139. The composition for use of aspect 138, wherein the anti-schizophrenia agent comprises risperidone or a pharmaceutically acceptable salt thereof.

140. Use of a composition as defined in any one of aspects 1 to 78 for the manufacture of a medicament for treating at least one of schizophrenia and bipolar disorder, wherein said composition contains a pharmaceutical active agent that is an anti-schizophrenia agent.

141. Use according to aspect 140, wherein the anti-schizophrenia agent comprises risperidone or a pharmaceutically acceptable salt thereof.

142. A process of sterilizing a composition, which process comprises gamma-irradiating a composition as defined in any one of aspects 1 to 78.

143. A monophasic composition, comprising:
25 wt % to 80 wt %, based on total weight of the composition, of sucrose acetate isobutyrate;
a poly(lactic acid)(glycolic acid) comprising an alkoxy end group wherein the alkoxy end group consists of 12 carbons, the poly(lactic acid)(glycolic acid) having a lactic acid to glycolic acid molar ratio of at least 70:30; and an organic solvent that maintains the composition monophasic at 25° C. and 1 atmosphere.

144. The composition of aspect 143, further comprising a pharmaceutical active agent.

145. The composition of aspect 144, wherein the pharmaceutical active agent is an anti-schizophrenia agent.

146. The composition of aspect 145, wherein the anti-schizophrenia agent comprises risperidone or a pharmaceutically acceptable salt thereof.

147. A method of treatment, comprising:
administering to a subject by injection a formulation comprised of: 25 wt % to 80 wt %, based on total weight of the composition, of sucrose acetate isobutyrate;
a poly(lactic acid)(glycolic acid) comprising an alkoxy end group wherein the alkoxy end group consists of 12 carbons, the poly(lactic acid)(glycolic acid) having a lactic acid to glycolic acid molar ratio of at least 70:30;
an organic solvent that maintains the composition monophasic at 25° C. and 1 atmosphere;
and a pharmaceutical active agent.

148. The method of aspect 147, wherein the pharmaceutical active agent is an anti-schizophrenia agent.

149. The method of aspect 148, wherein the anti-schizophrenia agent comprises risperidone or a pharmaceutically acceptable salt thereof.

150. The method of aspect 147, wherein:
the formulation is administered as a single dose subcutaneously to a human patient, and further wherein:
less than 10% of a total amount of the pharmaceutical active agent is released into the subject's circulation within 8 hours following injection,
10% to 80% of the total amount of the pharmaceutical active agent is released into the subject's circulation within 6 days following injection, and
20% to 100% of the total amount of the pharmaceutical active agent is released into the subject's circulation within 28 days following injection.

151. The method of aspect 150, wherein the pharmaceutical active agent is an anti-schizophrenia agent.

152. The method of aspect 151, wherein the anti-schizophrenia agent comprises risperidone or a pharmaceutically acceptable salt thereof.

153. A composition comprising:
a pharmaceutical active agent; and
a carrier vehicle,
wherein when 1 mL of the composition is administered as a single dose subcutaneously to a human patient:
median AUC (0 to 5 hours) of pharmaceutically active moiety is less than 10% of median AUC (0 to 28 days),
median AUC (5 hours to 7 days) of pharmaceutically active moiety ranges from 10% to 80% of median AUC (0 to 28 days), and
median AUC (7 days to 28 days) of pharmaceutically active moiety ranges from 10% to 90% or 10% to 80% of median AUC (0 to 28 days).

154. The composition of aspect 153, wherein the pharmaceutically active moiety consists of risperidone and 9-hydroxyrisperidone.

155. A composition comprising:
a pharmaceutical active agent; and
a carrier vehicle,
wherein when 1 mL of the composition is administered as a single dose subcutaneously to a human patient:
median AUC (0 to 5 hours) of pharmaceutical active agent is less than 10% of median AUC (0 to 28 days),
median AUC (5 hours to 7 days) of pharmaceutical active agent ranges from 10% to 80% of median AUC (0 to 28 days), and
median AUC (7 days to 28 days) of pharmaceutical active agent ranges from 10% to 80% of median AUC (0 to 28 days).

156. A composition comprising:
a pharmaceutical active agent; and
a carrier vehicle,
wherein when 1 mL of the composition is administered as a single dose subcutaneously to a human patient:
the median plasma concentration of pharmaceutically active moiety increases,
after the median plasma concentration of pharmaceutically active moiety increases, the median plasma concentration of pharmaceutically active moiety remains steady for a steady phase such that the median plasma concentration of pharmaceutically active moiety fluctuates less than ±30% for a period of at least 4 days, and
after the median plasma concentration of pharmaceutically active moiety remains steady, the median plasma concentration of pharmaceutically active moiety increases, relative to an end of the steady phase, by an amount ranging from about 0% to about 40% before decreasing.

157. The composition of aspect 156, wherein the median plasma concentration of pharmaceutically active moiety increases, relative to an end of the steady phase, by an amount ranging from about 5% to about 35% before decreasing.

158. The composition of any one of aspects 156 and 157, wherein the pharmaceutically active moiety consists of risperidone and 9-hydroxyrisperidone.

159. A composition comprising:
a pharmaceutical active agent; and
a carrier vehicle,
wherein when 1 mL of the composition is administered as a single dose subcutaneously to a human patient:
the median plasma concentration of pharmaceutical active agent increases,
after the median plasma concentration of pharmaceutical active agent increases, the median plasma concentration of pharmaceutical active agent remains steady for a steady phase such that the median plasma concentration of pharmaceutical active agent fluctuates less than ±30% for a period of at least 4 days, and
after the median plasma concentration of pharmaceutical active agent remains steady, the median plasma concentration of pharmaceutical active agent increases, relative to an end of the steady phase, by an amount ranging from about 5% to about 40% before decreasing.

160. The composition of aspect 159, wherein the median plasma concentration of pharmaceutically active agent increases, relative to an end of the steady phase, by an amount ranging from about 5% to about 35% before decreasing.

161. The composition of any one of aspects 153 to 160, wherein a median PK profile is described by 3 absorption phases:
a first absorption phase occurs immediately after administration, with a first order rate constant ranging from $0.1$ $hr^{-1}$ to $0.4$ $hr^{-1}$;
a second absorption phase occurs after a time delay ranging from 2.5 hours to 8.5 hours after administration, with a first order rate constant ranging from $0.0005$ $hr^{-1}$ to $0.005$ $hr^{-1}$; and a third absorption phase occurs after a time delay ranging from 5 days to 10 days after administration, with a first order rate constant ranging from 0.0005 hr$^{-1}$ to 0.005 hr$^{-1}$.

162. The composition of any one of aspects 153 to 160, wherein a median PK profile is described by 3 absorption phases:
a first absorption phase occurs immediately after administration, with a first order rate constant ranging from 0.2 hr$^{-1}$ to 0.3 hr$^{-1}$;
a second absorption phase occurs after a time delay ranging from 4.5 hours to 6.5 hours after administration, with a first order rate constant of ranging from 0.001 hr$^{-1}$ to 0.003 hr$^{-1}$; and
a third absorption phase occurs after a time delay ranging from 6 days to 9 days after administration, with a first order rate constant ranging from 0.001 hr$^{-1}$ to 0.003 hr$^{-1}$.

163. A composition comprising:
a pharmaceutical active agent; and
a carrier vehicle,
wherein when 1 mL of the composition is administered as a single dose subcutaneously to a human patient, the composition provides a median maximum blood plasma concentration (Cmax) of pharmaceutically active moiety ranging from about 70% to about 140% of 25 ng/mL, per 100 mg of pharmaceutical active agent administered, and a median AUC (0 to 28 days) of pharmaceutically active moiety ranging from about 70% to about 140% of 14,200 ng·hr/mL, per 100 mg of pharmaceutical active agent administered.

164. The composition of aspect 163, wherein the composition provides a median maximum blood plasma concentration (Cmax) of pharmaceutically active moiety ranging from about 80% to about 125% of 25 ng/mL, per 100 mg of pharmaceutical active agent administered, and a median AUC (0 to 28 days) of pharmaceutically active moiety ranging from about 80% to about 125% of 14,200 ng·hr/mL, per 100 mg of pharmaceutical active agent administered.

165. The composition of any one of aspects 163 and 164, wherein the pharmaceutically active moiety consists of risperidone and 9-hydroxyrisperidone.

166. A composition comprising:
a pharmaceutical active agent; and
a carrier vehicle,
wherein when 1 mL of the composition is administered as a single dose subcutaneously to a human patient, the composition provides a median maximum blood plasma concentration (Cmax) of pharmaceutical active agent ranging from about 70% to about 140% of 11 ng/mL, per 100 mg of pharmaceutical active agent administered, and a median AUC (0 to 28 days) of pharmaceutical active agent ranging from about 70% to about 140% of 3670 ng·hr/mL, per 100 mg of pharmaceutical active agent administered.

167. The composition of aspect 166, wherein the composition provides a median maximum blood plasma concentration (Cmax) of pharmaceutical active agent ranging from about 80% to about 125% of 11 ng/mL, per 100 mg of pharmaceutical active agent administered, and a median AUC (0 to 28 days) of pharmaceutical active agent ranging from about 80% to about 125% of 3670 ng·hr/mL, per 100 mg of pharmaceutical active agent administered.

168. A composition comprising:
a pharmaceutical active agent; and
a carrier vehicle,
wherein when the composition is administered as a single dose subcutaneously to a human patient, the composition provides a median pharmacokinetic profile of pharmaceutically active moiety within ±20% of the 100 mg dose profile of FIG. 30, per 100 mg of pharmaceutical active agent administered.

169. A composition comprising:
a pharmaceutical active agent; and
a carrier vehicle,
wherein when 1 mL of the composition is administered as a single dose subcutaneously to a human patient, the composition provides a pharmaceutically active moiety pharmacokinetic profile comprising:
a median first peak during a first period ranging from 2 hours after the administration to 4 days after the administration,
a median second peak during a second period ranging from 4 days after the administration to 14 days after the administration, and a median trough between the median first peak and the median second peak, wherein the median plasma concentration of pharmaceutically active moiety at the trough ranges from 40% to 90% of the median plasma concentration of pharmaceutically active moiety at the median second peak.

170. The composition of aspect 169, wherein the median first peak ranges from about 15 ng/mL to about 25 ng/mL, per 100 mg of pharmaceutical active agent administered.

171. The composition of aspect 169, wherein the median second peak ranges from about 20 ng/mL to about 30 ng/mL, per 100 mg of pharmaceutical active agent administered.

172. The composition of any one of aspects 169 to 171, wherein the pharmaceutically active moiety consists of risperidone and 9-hydroxyrisperidone.

173. A composition comprising:
a pharmaceutical active agent; and
a carrier vehicle,
wherein when 1 mL of the composition is administered as a single dose subcutaneously to a human patient, the composition provides a pharmaceutical active agent pharmacokinetic profile comprising:
a median first peak during a first period ranging from 2 hours after the administration to 4 days after the administration,
a median second peak during a second period ranging from 4 days after the administration to 14 days after the administration, and a median trough between the median first peak and the median second peak, wherein the median plasma concentration of pharmaceutical active agent at the trough ranges from 30% to 90% of the median plasma concentration of pharmaceutical active agent at the median second peak.

174. The composition of aspect 173, wherein the median first peak ranges from about 8 ng/mL to about 14 ng/mL, per 100 mg of pharmaceutical active agent administered.

175. The composition of aspect 173, wherein the second median peak ranges from about 4 ng/mL to about 10 ng/mL, per 100 mg of pharmaceutical active agent administered.

176. A composition comprising:
a pharmaceutical active agent; and
a carrier vehicle,
wherein when 1 mL of the composition is administered as a single dose subcutaneously to a human patient, the composition provides a pharmaceutically active moiety pharmacokinetic profile comprising three phases:
an increasing phase in which the median plasma concentration of pharmaceutically active moiety increases from about 0 ng/mL before administration to at least 5 ng/mL, per 100 mg of pharmaceutical active agent administered, at 24 hours after administration,
a steady phase ranging from 24 hours after administration to about 6 days after administration in which the median plasma concentration of pharmaceutically active moiety ranges from about 5 ng/mL to about 35 ng/mL, per 100 mg of pharmaceutical active agent administered, and
a final phase starting at about 6 days after administration in which the median plasma concentration of pharmaceutically active moiety increases before decreasing through at least about 28 days after administration.

177. The composition of aspect 176, wherein the pharmaceutically active moiety consists of risperidone and 9-hydroxyrisperidone.

178. A composition comprising:
a pharmaceutical active agent; and
a carrier vehicle,
wherein when 1 mL of the composition is administered as a single dose subcutaneously to a human patient, the composition provides a pharmaceutical active agent pharmacokinetic profile comprising three phases:
an increasing phase in which the median plasma concentration of pharmaceutical active agent increases from about 0 ng/mL before administration to at least 2 ng/mL, per 100 mg of pharmaceutical active agent administered, at about 24 hours after administration,
a steady phase ranging from about 24 hours after administration to about 6 days after administration in which the median plasma concentration of pharmaceutical active agent ranges from about 2 ng/mL to 15 ng/mL, per 100 mg of pharmaceutical active agent administered, and
a final phase starting at about 6 days after administration in which the plasma concentration of pharmaceutical active agent increases before decreasing through at least about 28 days after administration.

179. The composition of any one of aspects 153 to 178, wherein the pharmaceutical active agent comprises a small molecule antipsychotic.

180. The composition of any one of aspects 153 to 179, wherein the pharmaceutical active agent comprises risperidone.

181. The composition of any one of aspects 153 to 180, wherein the carrier vehicle comprises a non-polymeric, non-water soluble high viscosity liquid carrier material (HVLCM) having a viscosity of at least 5000 cP at 37° C. that does not crystallize neat at 25° C. and 1 atmosphere.

182. The composition of any one of aspects 153 to 181, wherein the carrier vehicle comprises a biodegradable polymer.

183. The composition of any one of aspects 153 to 182, wherein the carrier vehicle comprises a lactic-acid based polymer.

184. The composition of any one of aspects 153 to 183, wherein the carrier vehicle comprises poly(lactic acid) (glycolic acid).

185. The composition of any one of aspects 153 to 184, wherein the carrier vehicle comprises poly(lactic acid) (glycolic acid) comprising an alkoxy end group.

186. The composition of any one of aspects 153 to 185, wherein the carrier vehicle comprises poly(lactic acid) (glycolic acid) comprising a dodeoxy end group.

187. The composition of any one of aspects 153 to 186, wherein the carrier vehicle comprises an organic solvent.

188. A method comprising:
administering to a patient a composition comprising a pharmaceutical active agent and a carrier vehicle,
wherein:
AUC (0 to 5 hours) of pharmaceutically active moiety is less than 10% of AUC (0 to 28 days),
AUC (5 hours to 7 days) of pharmaceutically active moiety ranges from 10% to 80% of AUC (0 to 28 days), and
AUC (7 days to 28 days) of pharmaceutically active moiety ranges from 10% to 80% of AUC (0 to 28 days).

189. The method of aspect 188, wherein the pharmaceutically active moiety consists of risperidone and 9-hydroxyrisperidone.

190. A method comprising:
administering to a patient a composition comprising a pharmaceutical active agent and a carrier vehicle,
wherein:
AUC (0 to 5 hours) of pharmaceutical active agent is less than 10% of AUC (0 to 28 days),
AUC (5 hours to 7 days) of pharmaceutical active agent ranges from 10% to 80% of AUC (0 to 28 days), and
AUC (7 days to 28 days) of pharmaceutical active agent ranges from 10% to 80% of AUC (0 to 28 days).

191. A method comprising:
administering to a patient a composition comprising a pharmaceutical active agent and a carrier vehicle,
wherein:
the plasma concentration of pharmaceutically active moiety increases,
after the plasma concentration of pharmaceutically active moiety increases, the plasma concentration of pharmaceutically active moiety remains steady for a steady phase such that the plasma concentration of pharmaceutically active moiety fluctuates less than ±30% for a period of at least 4 days, and
after the plasma concentration of pharmaceutically active moiety remains steady, the plasma concentration of pharmaceutically active moiety increases, relative to an end of the steady phase, by an amount ranging from about 0% to about 40% before decreasing.

192. The method of aspect 191, wherein the plasma concentration of pharmaceutically active moiety increases, relative to an end of the steady phase, by an amount ranging from about 5% to about 35% before decreasing.

193. The method of any one of aspects 190 and 191, wherein the pharmaceutically active moiety consists of risperidone and 9-hydroxyrisperidone.

194. A method comprising:
administering to a patient a composition comprising a pharmaceutical active agent and a carrier vehicle, wherein:
the plasma concentration of pharmaceutical active agent increases,
after the plasma concentration of pharmaceutical active agent increases, the plasma concentration of pharmaceutical active agent remains steady for a steady phase such that the plasma concentration of pharmaceutical active agent fluctuates less than ±30% for a period of at least 4 days, and
after the plasma concentration of pharmaceutical active agent remains steady, the plasma concentration of pharmaceutical active agent increases, relative to an end of the steady phase, by an amount ranging from about 0% to about 40% before decreasing.

195. The method of aspect 194, wherein the plasma concentration of pharmaceutically active agent increases, relative to an end of the steady phase, by an amount ranging from about 5% to about 35% before decreasing.

196. The method of any one of aspects 188 to 195, wherein a PK profile is described by 3 absorption phases:
a first absorption phase occurs immediately after administration, with a first order rate constant ranging from $0.1\ hr^{-1}$ to $0.4\ hr^{-1}$;
a second absorption phase occurs after a time delay ranging from 2.5 hours to 8.5 hours after administration, with a first order rate constant ranging from $0.0005\ hr^{-1}$ to $0.005\ hr^{-1}$; and
a third absorption phase occurs after a time delay ranging from 5 days to 10 days after administration, with a first order rate constant ranging from $0.0005\ hr^{-1}$ to $0.005\ hr^{-1}$.

197. The method of any one of aspects 188 through 195, wherein a PK profile is described by 3 absorption phases:
a first absorption phase occurs immediately after administration, with a first order rate constant ranging from $0.2\ hr^{-1}$ to $0.3\ hr^{-1}$;
a second absorption phase occurs after a time delay ranging from 4.5 hours to 6.5 hours after administration, with a first order rate constant of ranging from $0.001\ hr^{-1}$ to $0.003\ hr^{-1}$; and a third absorption phase occurs after a time delay ranging from 6 days to 9 days after administration, with a first order rate constant ranging from $0.001\ hr^{-1}$ to $0.003\ hr^{-1}$.

198. A method comprising:
administering to a patient a composition comprising a pharmaceutical active agent and a carrier vehicle,
wherein a maximum blood plasma concentration (Cmax) of pharmaceutically active moiety ranges from about 70% to about 140% of 25 ng/mL, per 100 mg of pharmaceutical active agent administered, and an AUC (0 to 28 days) of pharmaceutically active moiety ranges from about 70% to about 140% of 14,200 ng·hr/mL, per 100 mg of pharmaceutical active agent administered.

199. The method of aspect 198, wherein the maximum blood plasma concentration (Cmax) of pharmaceutically active moiety ranges from about 80% to about 125% of 25 ng/mL, per 100 mg of pharmaceutical active agent administered, and the AUC (0 to 28 days) of pharmaceutically active moiety ranges from about 80% to about 125% of 14,200 ng·hr/mL, per 100 mg of pharmaceutical active agent administered.

200. The method of any one of aspects 198 and 199, wherein the pharmaceutically active moiety consists of risperidone and 9-hydroxyrisperidone.

201. A method comprising:
administering to a patient a composition comprising a pharmaceutical active agent and a carrier vehicle,
wherein a maximum blood plasma concentration (Cmax) of pharmaceutical active agent ranges from about 70% to about 140% of 11 ng/mL, per 100 mg of pharmaceutical active agent administered, and an AUC (0 to 28 days) of pharmaceutical active agent ranges from about 70% to about 140% of 3670 ng·hr/mL, per 100 mg of pharmaceutical active agent administered.

202. The method of aspect 201, wherein the maximum blood plasma concentration (Cmax) of pharmaceutical active agent ranges from about 80% to about 125% of 11 ng/mL, per 100 mg of pharmaceutical active agent administered, and the AUC (0 to 28 days) of pharmaceutical active agent ranges from about 80% to about 125% of 3670 ng·hr/mL, per 100 mg of pharmaceutical active agent administered.

203. A method comprising:
administering to a patient a composition comprising a pharmaceutical active agent and a carrier vehicle,
wherein a pharmacokinetic profile of pharmaceutically active moiety is within ±20% of the 100 mg dose profile of FIG. 30, per 100 mg of pharmaceutical active agent administered.

204. A method comprising:
administering to a patient a composition comprising a pharmaceutical active agent and a carrier vehicle,
wherein a pharmaceutically active moiety pharmacokinetic profile comprises:
a first peak during a first period ranging from 2 hours after the administration to 4 days after the administration,
a second peak during a second period ranging from 4 days after the administration to 14 days after the administration, and a trough between the first peak and the second peak, wherein the plasma concentration of pharmaceutically active moiety at the trough ranges from 40% to 90% of the plasma concentration of pharmaceutically active moiety at the second peak.

205. The method of aspect 204, wherein the first peak ranges from about 15 ng/mL to about 25 ng/mL, per 100 mg of pharmaceutical active agent administered.

206. The method of aspect 204, wherein the second peak ranges from about 20 ng/mL to about 30 ng/mL, per 100 mg of pharmaceutical active agent administered.

207. The method of any one of aspects 204 to 206, wherein the pharmaceutically active moiety consists of risperidone and 9-hydroxyrisperidone.

208. A method comprising:
administering to a patient a composition comprising a pharmaceutical active agent and a carrier vehicle,
wherein a pharmaceutical active agent pharmacokinetic profile comprises:
a first peak during a first period ranging from 2 hours after the administration to 4 days after the administration, a second peak during a second period ranging from 4 days after the administration to 14 days after the administration, and
a trough between the first peak and the second peak, wherein the plasma concentration of pharmaceutical active agent at the trough ranges from 30% to 90% of the plasma concentration of pharmaceutical active agent at the second peak.
209. The method of aspect 208, wherein the first peak ranges from about 8 ng/mL to about 14 ng/mL, per 100 mg of pharmaceutical active agent administered.
210. The method of aspect 208, wherein the second peak ranges from about 4 ng/mL to about 10 ng/mL, per 100 mg of pharmaceutical active agent administered.
211. A method comprising:
administering to a patient a composition comprising a pharmaceutical active agent and a carrier vehicle, wherein a pharmaceutically active moiety pharmacokinetic profile comprises three phases:
an increasing phase in which the plasma concentration of pharmaceutically active moiety increases from about 0 ng/mL before administration to at least 5 ng/mL, per 100 mg of pharmaceutical active agent administered, at 24 hours after administration,
a steady phase ranging from 24 hours after administration to about 6 days after administration in which the plasma concentration of pharmaceutically active moiety ranges from about 5 ng/mL to about 35 ng/mL, per 100 mg of pharmaceutical active agent administered, and
a final phase starting at about 6 days after administration in which the plasma concentration of pharmaceutically active moiety increases before decreasing through at least about 28 days after administration.
212. The method of aspect 211, wherein the pharmaceutically active moiety consists of risperidone and 9-hydroxyrisperidone.
213. A method comprising:
administering to a patient a composition comprising a pharmaceutical active agent and a carrier vehicle, wherein a pharmaceutical active agent pharmacokinetic profile comprises three phases:
an increasing phase in which the plasma concentration of pharmaceutical active agent increases from about 0 ng/mL before administration to at least 2 ng/mL, per 100 mg of pharmaceutical active agent administered, at about 24 hours after administration,
a steady phase ranging from about 24 hours after administration to about 6 days after administration in which the plasma concentration of pharmaceutical active agent ranges from about 2 ng/mL to 15 ng/mL, per 100 mg of pharmaceutical active agent administered, and
a final phase starting at about 6 days after administration in which the plasma concentration of pharmaceutical active agent increases before decreasing through at least about 28 days after administration.
214. The method of any one of aspects 188 to 213, wherein the pharmaceutical active agent comprises a small molecule antipsychotic.
215. The method of any one of aspects 188 to 214, wherein the pharmaceutical active agent comprises risperidone.
216. The method of any one of aspects 188 to 215, wherein the carrier vehicle comprises a non-polymeric, non-water soluble high viscosity liquid carrier material (HVLCM) having a viscosity of at least 5000 cP at 37° C. that does not crystallize neat at 25° C. and 1 atmosphere.
217. The method of any one of aspects 188 to 216, wherein the carrier vehicle comprises a biodegradable polymer.
218. The method of any one of aspects 188 to 217, wherein the carrier vehicle comprises a lactic-acid based polymer.
219. The method of any one of aspects 188 to 218, wherein the carrier vehicle comprises poly(lactic acid) (glycolic acid).
220. The method of any one of aspects 188 to 219, wherein the carrier vehicle comprises poly(lactic acid) (glycolic acid) comprising an alkoxy end group.
221. The method of any one of aspects 188 to 220, wherein the carrier vehicle comprises poly(lactic acid) (glycolic acid) comprising a dodeoxy end group.
222. The method of any one of aspects 188 to 221, wherein the carrier vehicle comprises an organic solvent.
223. The method of any one of aspects 188 to 222, wherein the method comprises treating at least one of schizophrenia and bipolar disorder.
224. The method of any one of aspects 188 to 223, wherein the administering comprises parenteral administration.
225. The method of any one of aspects 188 to 224, wherein the administering comprises subcutaneous administration.
226. The method of any one of aspects 116 to 129 and 188 to 225, wherein the composition is self-administered.
227. The method of any one of aspects 116 to 129 and 188 to 226, wherein the composition is administered by a non-health care professional.
228. The method of any one of aspects 116 to 129 and 188 to 227, wherein the composition is administered with a needle and syringe.
229. The method of aspect 228, wherein the needle has a length of less than or equal to 1 inch.
230. The method of aspect 228, wherein the needle has a length of less than or equal to ⅝ inch.
231. The method of aspect 228, wherein the needle has a length of less than or equal to 0.5 inch.
232. The method of any one of aspects 116 to 129 and 188 to 227, wherein the composition is administered with a pre-filled syringe or an auto-injector.
233. The method of any one of aspects 116 to 129 and 188 to 232, wherein the composition is administered once a month.
234. The method of any one of aspects 116 to 129 and 188 to 233, wherein the method does not comprise a separate loading dose administered at a different frequency.
235. The method of any one of aspects 116 to 129 and 188 to 234, wherein a plasma concentration of pharmaceutically active moiety ranges from about 5 ng/mL to about 45 ng/mL, per 100 mg of pharmaceutical active agent administered, during 1 day following single administration to 28 days following single administration.
236. The method of any one of aspects 116 to 129 and 188 to 235, wherein a plasma concentration of pharmaceutically active moiety ranges from about 10 ng/mL to about 35 ng/mL, per 100 mg of pharmaceutical active agent administered, during 1 day following single administration to 28 days following single administration.

237. The method of any one of aspects 116 to 129 and 188 to 236, wherein a plasma concentration of pharmaceutically active moiety ranges from about 10 ng/mL to about 30 ng/mL, per 100 mg of pharmaceutical active agent administered, during 1 day following single administration to 28 days following single administration.

238. The method of any one of aspects 116 to 129 and 188 to 237, wherein a plasma concentration of pharmaceutical active agent ranges from about 2 ng/mL to about 20 ng/mL, per 100 mg of pharmaceutical active agent administered, during 1 day following single administration to 28 days following single administration.

239. The method of any one of aspects 116 to 129 and 188 to 238, wherein a plasma concentration of pharmaceutical active agent ranges from about 2 ng/mL to about 15 ng/mL, per 100 mg of pharmaceutical active agent administered, during 1 day following single administration to 28 days following single administration.

240. A composition comprising:
a pharmaceutical active agent that is a peptide, small molecule, or pharmaceutically acceptable salt thereof;
a non-polymeric, non-water soluble high viscosity liquid carrier material (HVLCM) having a viscosity of at least 5000 cP at 37° C. that does not crystallize neat at 25° C. and 1 atmosphere, a lactic acid-based polymer comprising an alkoxy end group, and an organic solvent in a ratio sufficient to maintain a therapeutically effective plasma concentration of the pharmaceutical active agent for a period of at least 7 days when the composition is administered subcutaneously as a single dose to a human patient.

BRIEF DESCRIPTION OF THE DRAWINGS

The present disclosure is further described in the description that follows, in reference to the noted plurality of non-limiting drawings, wherein:

FIG. 32 shows the estimated parameters for a base structural model developed using the oral (PO) data only.

FIG. 33 shows the estimated parameters for a base structural model developed using both PO and SC data.

Figure 1:
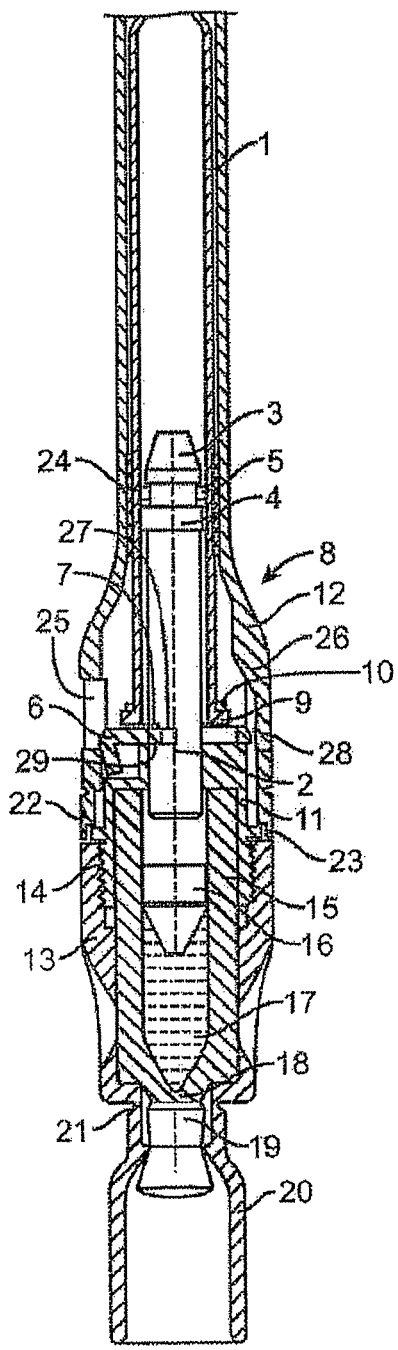
FIG. 1 presents a longitudinal cross-section through a needle-free injector.

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Before further discussion, a definition of the following terms will aid in the understanding of the present disclosure.

"Administering" or "administration" means providing a drug to a subject in a manner that is pharmacologically useful.

"Pharmaceutically active moiety" means a molecule or ion, excluding those appended portions of the molecule that cause the drug to be an ester, salt (including a salt with hydrogen or coordination bonds), or other noncovalent derivative (such as a complex, chelate, or clathrate) of the molecule, responsible for the physiological or pharmacological action of the drug substance. For risperidone and paliperidone, the active moiety in general is the sum of free risperidone and risperidone in the form of 9-hydroxyrisperidone.

"Polymer" means a naturally occurring or synthetic compound made up of a linked series of repeat units. Polymer(s) include, but are not limited to, thermoplastic polymers and thermoset polymers. Polymer(s) may comprise linear polymers and/or branched polymers. Polymers may be synthesized from a single species of monomers, or may be copolymers that may be synthesized from more than one species of monomers.

"Copolymer" includes terpolymers, etc.

"Linear" means a polymer in which the molecules form long chains substantially without branches or cross-linked structures.

"Weight average molecular weight" or "Mw" means the weighted average molecular weight of polymers of interest. It can be expressed at the first moment of a plot of the weight of polymer in each molecular weight range against molecular weight. In certain embodiments, weight-average molecular weight, Number-average molecular weight (Mn), and the molecular weight distribution (MWD=Mw/Mn) may be measured by gel permeation chromatography (GPC). GPC is a column fractionation method wherein polymer molecules in solutions are separated based on their sizes. The separated polymer molecules are observed by a detector to generate the GPC chromatogram, which is a plot of elution volume or time (related to molecular size) versus abundance. The GPC chromatogram may be integrated to determine Mw, Mn, and MWD.

GPC samples of polymer(s) of interest, approximately 50 mg in 10 mL solvent, are filtered through a 0.2 μm Teflon filter before injection into the instrument. Injections of 50-200 μL are made to generate chromatograms. Chromatograms may be generated using various systems. In an embodiment, a system comprises an Agilent LC 1100 using Chemstation software. In another embodiment, a system comprises a Waters 510 pump, a Shimadzu CTO-10A column oven, and a Waters 410 differential refractometer. Data may be recorded directly to a PC via a Polymer Labs data capture unit using Caliber® software. A calibration curve may be generated using polystyrene standards. Mw, Mn, and MWD relative to polystyrene are calculated. Representative solvents for use in GPC comprise: chloroform, dichlormethane (methylene chloride), and tetrahydrofuran (THF). Representative column sets comprise: (1) two Polymer Labs Mixed C columns in series, (2) two Polymer Labs Mixed D columns in series, or (3) two Polymer Labs Mesopore columns in series. Representative polystyrene calibrants comprise: Polymer Labs Easical PS1 kit, Polymer Labs Easical PS2 kit, Polymer Labs S-L-10 kit.

"Solvent" means material that is capable of dissolving other materials.

"Hydrophilic solvent" means substantially water-miscible solvents, preferably those when mixed with water in a ratio from 1:9 to 9:1 form a single-phase solution.

"Solvent capacity" means amount(s) of the one or more solvents that dissolves the HVLCM and polymer in the composition to the same extent as would a hypothetical amount of N-methylpyrrolidone in the composition. Solvent capacity is expressed as that hypothetical weight percent of N-methylpyrrolidone in the composition, based on the total weight of the hypothetical composition that would contain the N-methylpyrrolidone.

Thus, for example, a composition having a solvent capacity of about 20% would have sufficient amounts of one or more solvents to dissolve the HVLCM and linear polymer to the same extent as if about 20% by weight of NMP were added to the composition instead of the one or more solvents. If NMP were present as the one or more solvents in this embodiment, it would be present in an amount of about 20% by weight, based on the total weight of the composition. If the one or more solvents were poorer solvents for the HVLCM and linear polymer, then the one or more solvents would be present in an amount greater than about 20% by weight, based on the total weight of the composition.

As used herein, the term "viscosity" means viscosity as determined by a skilled artisan using a plate and cone viscometer (e.g., Brookfield Model DV-III) at a temperature of interest.

"Subject" is used interchangeably with "individual" and means any human or animal with which it is desired to practice the present disclosure. The term "subject" does not denote a particular age, and the present systems are thus suited for use with subjects of any age, such as infant, adolescent, adult and senior aged subjects In certain embodiments, a subject may comprise a patient.

As used herein, "median," when used to describe pharmacokinetic results, means the median from at least eight randomly selected subjects or patients, unless otherwise noted.

"Cmax" is the maximum concentration of the pharmaceutical active agent—or pharmaceutically active moiety—in a person's blood plasma. AUC (0 to 28) days represents the area under the blood plasma concentration curve over 28 days.

"Steady state" is the PK profile over one dosing interval that is achieved after several doses and any loading doses are given. In modeling, steady state is the PK profile achieved after a theoretical infinite number of doses are given.

"Triphasic absorption" is a sustained release profile characterized by three distinct release phases. Each phase in general is characterized by a distinct absorption rate constant and time delay, although the time delay for the first phase can be zero. Triphasic absorption is advantageous in that it allows more adjustable parameters and better control over plasma levels, and enable less frequent dosing, for example, once every 28 days.

In one aspect, the present composition comprises 25 wt % to 80 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere; a lactic-acid based polymer that is poly(lactic acid)(glycolic acid) comprising an alkoxy end group, the poly(lactic acid)(glycolic acid) having a lactic acid to glycolic acid molar ratio greater than 65:35; and an organic solvent.

In another aspect, the present composition comprises 25 wt % to 80 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere; a lactic acid-based polymer comprising an alkoxy end group, wherein the lactic acid-based polymer has a weight average molecular weight ranging from 5000 Daltons to 30,000 Daltons, 6000 Daltons to 30,000 Daltons, or 7000 Daltons to 30,000 Daltons; and an organic solvent.

In yet another aspect, the present composition comprises a pharmaceutical active agent; 25 wt % to 80 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere; a lactic acid-based polymer comprising an alkoxy end group; and an organic solvent.

In still another aspect, the present composition comprises particles comprising pharmaceutical active agent, the particles having a median particle size, as measured by laser diffraction, ranging from 0.5 micrometers to 10 micrometers; 25 wt % to 80 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere; a lactic acid-based polymer; and an organic solvent.

In a further aspect, a gamma-irradiated composition comprises pharmaceutical active agent; and wherein the gamma-irradiated composition further comprises 25 wt % to 80 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere; a lactic acid-based polymer; and an organic solvent.

In another aspect, the present composition comprises a pharmaceutical active agent that is risperidone or pharmaceutically acceptable salt thereof; a non-polymeric, non-water soluble high viscosity liquid carrier material (HVLCM) having a viscosity of at least 5000 cP at 37° C. that does not crystallize neat at 25° C. and 1 atmosphere, a lactic acid-based polymer comprising an alkoxy end group, and an organic solvent in a ratio sufficient to maintain a therapeutically effective plasma concentration of the risperidone or pharmaceutically acceptable salt thereof for a period of at least 7 days when the composition is administered subcutaneously as a single dose to a human patient.

In still another aspect, the present composition comprises a pharmaceutical active agent that is risperidone or pharmaceutically acceptable salt thereof; a non-polymeric, non-water soluble high viscosity liquid carrier material (HVLCM) having a viscosity of at least 5000 cP at 37° C. that does not crystallize neat at 25° C. and 1 atmosphere, a lactic acid-based polymer comprising an alkoxy end group, and an organic solvent in a ratio such that when the composition is administered subcutaneously as a single dose to a human patient, a median amount of pharmaceutical active agent released from the composition provides an AUC (0 to 1 day) that is less than 10%, such as less than 5%, of AUC (0 to 28 days).

In a further aspect, the present composition comprises 5 wt % to 20 wt %, based on total weight of the composition, of particles comprising pharmaceutical active agent that is risperidone or pharmaceutically acceptable salt thereof, the particles having a median particle size, as measured by laser diffraction, ranging from 0.5 micrometer to 7 micrometers; 30 wt % to 60 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere, wherein the HVLCM is sucrose acetate isobutyrate; 5 wt % to 30 wt %, based on total weight of the composition, of a lactic acid based-polymer that is poly(lactic acid)(glycolic acid) comprising an alkoxy end group, the poly(lactic acid)(glycolic acid) having a lactic acid to glycolic acid molar ratio ranging from 95:5 to 60:40, the poly(lactic acid)(glycolic acid) having a weight average molecular weight ranging from 4000 Daltons to 15,000 Daltons; and 10 wt % to 50 wt % or 10 wt % to 40 wt %, based on total weight of the composition, of a solvent that is at least one member selected from N-methyl-pyrrolidone, propylene carbonate, and dimethylsulfoxide.

In another aspect, the present composition comprises a pharmaceutical active agent that is risperidone or pharmaceutically acceptable salt thereof; means for extending a release profile of the pharmaceutical active agent when the composition is administered to a patient in need thereof.

In a still further aspect, the present composition comprises a pharmaceutical active agent that is risperidone or pharmaceutically acceptable salt thereof; means for reducing settling of the pharmaceutical active agent within the composition.

In one aspect, the present composition comprises a pharmaceutical active agent; and a carrier vehicle, wherein when 1 mL of the composition is administered as a single dose subcutaneously to a human patient: median AUC (0 to 5 hours) of pharmaceutically active moiety is less than 10% of median AUC (0 to 28 days), median AUC (5 hours to 7 days) of pharmaceutically active moiety ranges from 10% to 80% of median AUC (0 to 28 days), and median AUC (7 days to 28 days) of pharmaceutically active moiety ranges from 10% to 80% of median AUC (0 to 28 days).

In another aspect, the present composition comprises a pharmaceutical active agent; and a carrier vehicle, wherein when 1 mL of the composition is administered as a single dose subcutaneously to a human patient: median AUC (0 to 5 hours) of pharmaceutical active agent is less than 10% of median AUC (0 to 28 days), median AUC (5 hours to 7 days) of pharmaceutical active agent ranges from 10% to 80% of median AUC (0 to 28 days), and median AUC (7 days to 28 days) of pharmaceutical active agent ranges from 10% to 80% of median AUC (0 to 28 days).

In still another aspect, the present composition comprises a pharmaceutical active agent; and a carrier vehicle, wherein when 1 mL of the composition is administered as a single dose subcutaneously to a human patient: the median plasma concentration of pharmaceutically active moiety increases, after the median plasma concentration of pharmaceutically active moiety increases, the median plasma concentration of pharmaceutically active moiety remains steady for a steady phase such that the median plasma concentration of pharmaceutically active moiety fluctuates less than ±30% for a period of at least 4 days, and after the median plasma concentration of pharmaceutically active moiety remains steady, the median plasma concentration of pharmaceutically active moiety increases, relative to an end of the steady phase, by an amount ranging from about 0% to about 40% before decreasing.

In yet another aspect, the present composition comprises a pharmaceutical active agent; and a carrier vehicle, wherein when 1 mL of the composition is administered as a single dose subcutaneously to a human patient: the median plasma concentration of pharmaceutical active agent increases, after the median plasma concentration of pharmaceutical active agent increases, the median plasma concentration of pharmaceutical active agent remains steady for a steady phase such that the median plasma concentration of pharmaceutical active agent fluctuates less than ±30% for a period of at least 4 days, and after the median plasma concentration of pharmaceutical active agent remains steady, the median plasma concentration of pharmaceutical active agent increases, relative to an end of the steady phase, by an amount ranging from about 5% to about 40% before decreasing.

In a further aspect, the present composition comprises a pharmaceutical active agent; and a carrier vehicle, wherein when 1 mL of the composition is administered as a single dose subcutaneously to a human patient, the composition provides a median maximum blood plasma concentration (Cmax) of pharmaceutically active moiety ranging from about 70% to about 140% of 25 ng/mL, per 100 mg of pharmaceutical active agent administered, and a median AUC (0 to 28 days) of pharmaceutically active moiety ranging from about 70% to about 140% of 14,200 ng·hr/mL, per 100 mg of pharmaceutical active agent administered.

In another aspect, the present composition comprises a pharmaceutical active agent; and a carrier vehicle, wherein when 1 mL of the composition is administered as a single dose subcutaneously to a human patient, the composition provides a median maximum blood plasma concentration (Cmax) of pharmaceutical active agent ranging from about 70% to about 140% of 11 ng/mL, per 100 mg of pharmaceutical active agent administered, and a median AUC (0 to 28 days) of pharmaceutical active agent ranging from about 70% to about 140% of 3670 ng·hr/mL, per 100 mg of pharmaceutical active agent administered.

Figure 30:
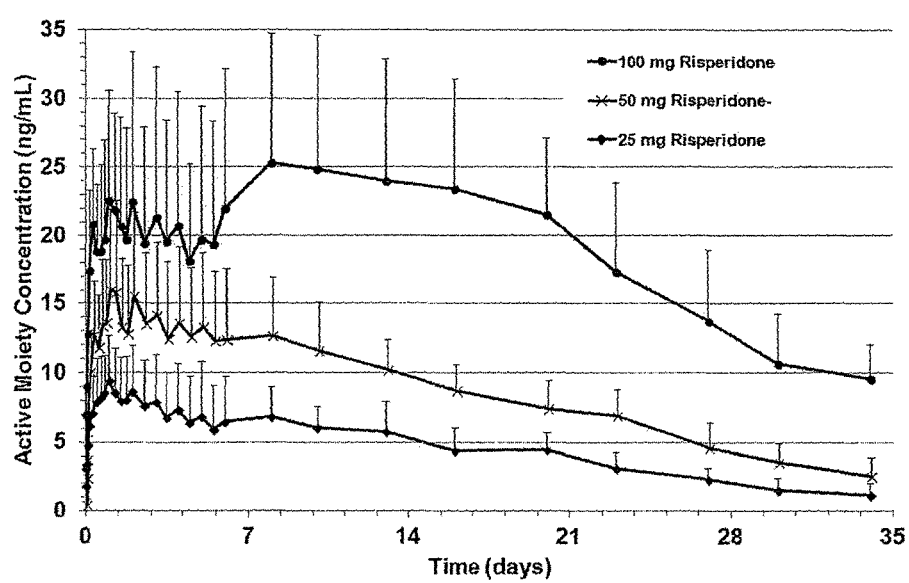
FIG. 30 shows the PK profiles when 25 mg, 50 mg, and 100 mg, respectively, of risperidone in a vehicle comprising sucrose acetate isobutyrate (SAIB) were administered as a SC injection of 0.25 mL, 0.50 mL, and 1.0 mL, respectively, (100 mg/mL concentration) in the abdominal region of humans.

In still another aspect, the present composition comprises a pharmaceutical active agent; and a carrier vehicle, wherein when the composition is administered as a single dose subcutaneously to a human patient, the composition provides a median pharmacokinetic profile of pharmaceutically active moiety within ±20% of the 100 mg dose profile of FIG. 30, per 100 mg of pharmaceutical active agent administered.

In another aspect, the present composition comprises a pharmaceutical active agent; and a carrier vehicle, wherein when 1 mL of the composition is administered as a single dose subcutaneously to a human patient, the composition provides a pharmaceutically active moiety pharmacokinetic profile comprising: a median first peak during a first period ranging from 2 hours after the administration to 4 days after the administration, a median second peak during a second period ranging from 4 days after the administration to 14 days after the administration, and a median trough between the median first peak and the median second peak, wherein the median plasma concentration of pharmaceutically active moiety at the trough ranges from 40% to 90% of the median plasma concentration of pharmaceutically active moiety at the median second peak.

In yet another aspect, a composition comprises a pharmaceutical active agent; and a carrier vehicle, wherein when 1 mL of the composition is administered as a single dose subcutaneously to a human patient, the composition provides a pharmaceutical active agent pharmacokinetic profile comprising: a median first peak during a first period ranging from 2 hours after the administration to 4 days after the administration, a median second peak during a second period ranging from 4 days after the administration to 14 days after the administration, and a median trough between the median first peak and the median second peak, wherein the median plasma concentration of pharmaceutical active agent at the trough ranges from 30% to 90% of the median plasma concentration of pharmaceutical active agent at the median second peak.

In another aspect, the present composition comprises a pharmaceutical active agent; and a carrier vehicle, wherein when 1 mL of the composition is administered as a single dose subcutaneously to a human patient, the composition provides a pharmaceutically active moiety pharmacokinetic profile comprising three phases: an increasing phase in which the median plasma concentration of pharmaceutically active moiety increases from about 0 ng/mL before administration to at least 5 ng/mL, per 100 mg of pharmaceutical active agent administered, at 24 hours after administration, a steady phase ranging from 24 hours after administration to about 6 days after administration in which the median plasma concentration of pharmaceutically active moiety ranges from about 5 ng/mL to about 35 ng/mL, per 100 mg of pharmaceutical active agent administered, and a final phase starting at about 6 days after administration in which the median plasma concentration of pharmaceutically active moiety increases before decreasing through at least about 28 days after administration.

In a further aspect, the present composition comprises a pharmaceutical active agent; and a carrier vehicle, wherein when 1 mL of the composition is administered as a single dose subcutaneously to a human patient, the composition provides a pharmaceutical active agent pharmacokinetic profile comprising three phases: an increasing phase in which the median plasma concentration of pharmaceutical active agent increases from about 0 ng/mL before administration to at least 2 ng/mL, per 100 mg of pharmaceutical active agent administered, at about 24 hours after administration, a steady phase ranging from about 24 hours after administration to about 6 days after administration in which the median plasma concentration of pharmaceutical active agent ranges from about 2 ng/mL to 15 ng/mL, per 100 mg of pharmaceutical active agent administered, and a final phase starting at about 6 days after administration in which the plasma concentration of pharmaceutical active agent increases before decreasing through at least about 28 days after administration.

In one aspect, the present method comprises administering to a patient a composition comprising a pharmaceutical active agent and a carrier vehicle, wherein: AUC (0 to 5 hours) of pharmaceutically active moiety is less than 10% of AUC (0 to 28 days), AUC (5 hours to 7 days) of pharmaceutically active moiety ranges from 10% to 80% of AUC (0 to 28 days), and AUC (7 days to 28 days) of pharmaceutically active moiety ranges from 10% to 100% or 10% to 80% of AUC (0 to 28 days).

In yet another aspect, the present method comprises administering to a patient a composition comprising a pharmaceutical active agent and a carrier vehicle, wherein: AUC (0 to 5 hours) of pharmaceutical active agent is less than 10% of AUC (0 to 28 days), AUC (5 hours to 7 days) of pharmaceutical active agent ranges from 10% to 80% of AUC (0 to 28 days), and AUC (7 days to 28 days) of pharmaceutical active agent ranges from 10% to 80% of AUC (0 to 28 days).

In another aspect, the present method comprises administering to a patient a composition comprising a pharmaceutical active agent and a carrier vehicle, wherein: the plasma concentration of pharmaceutically active moiety increases, after the plasma concentration of pharmaceutically active moiety increases, the plasma concentration of pharmaceutically active moiety remains steady for a steady phase such that the plasma concentration of pharmaceutically active moiety fluctuates less than ±30% for a period of at least 4 days, and after the plasma concentration of pharmaceutically active moiety remains steady, the plasma concentration of pharmaceutically active moiety increases, relative to an end of the steady phase, by an amount ranging from about 0% to about 40% before decreasing.

In still another aspect, the present method comprises administering to a patient a composition comprising a pharmaceutical active agent and a carrier vehicle, wherein: the plasma concentration of pharmaceutical active agent increases, after the plasma concentration of pharmaceutical active agent increases, the plasma concentration of pharmaceutical active agent remains steady for a steady phase such that the plasma concentration of pharmaceutical active agent fluctuates less than ±30% for a period of at least 4 days, and after the plasma concentration of pharmaceutical active agent remains steady, the plasma concentration of pharmaceutical active agent increases, relative to an end of the steady phase, by an amount ranging from about 5% to about 40% before decreasing.

In yet another aspect, the present method comprises administering to a patient a composition comprising a pharmaceutical active agent and a carrier vehicle, wherein a maximum blood plasma concentration (Cmax) of pharmaceutically active moiety ranges from about 70% to about 140% of 25 ng/mL, per 100 mg of pharmaceutical active agent administered, and an AUC (0 to 28 days) of pharmaceutically active moiety ranges from about 70% to about 140% of 14,200 ng·hr/mL, per 100 mg of pharmaceutical active agent administered.

In a further aspect, the present method comprises administering to a patient a composition comprising a pharmaceutical active agent and a carrier vehicle, wherein a maximum blood plasma concentration (Cmax) of pharmaceutical active agent ranges from about 70% to about 140% of 11 ng/mL, per 100 mg of pharmaceutical active agent administered, and an AUC (0 to 28 days) of pharmaceutical active agent ranges from about 70% to about 140% of 3670 ng·hr/mL, per 100 mg of pharmaceutical active agent administered.

In another aspect, the present method comprises administering to a patient a composition comprising a pharmaceutical active agent and a carrier vehicle, wherein a pharmacokinetic profile of pharmaceutically active moiety is within ±20% of the 100 mg dose profile of FIG. 30, per 100 mg of pharmaceutical active agent administered.

In still another aspect, the present method comprises administering to a patient a composition comprising a pharmaceutical active agent and a carrier vehicle, wherein a pharmaceutically active moiety pharmacokinetic profile comprises: a first peak during a first period ranging from 2 hours after the administration to 4 days after the administration, a second peak during a second period ranging from 4 days after the administration to 14 days after the administration, and a trough between the first peak and the second peak, wherein the plasma concentration of pharmaceutically active moiety at the trough ranges from 40% to 90% of the plasma concentration of pharmaceutically active moiety at the second peak.

In yet another aspect, the present method comprises administering to a patient a composition comprising a pharmaceutical active agent and a carrier vehicle, wherein a pharmaceutical active agent pharmacokinetic profile comprises: a first peak during a first period ranging from 2 hours after the administration to 4 days after the administration, a second peak during a second period ranging from 4 days after the administration to 14 days after the administration, and a trough between the first peak and the second peak, wherein the plasma concentration of pharmaceutical active agent at the trough ranges from 30% to 90% of the plasma concentration of pharmaceutical active agent at the second peak.

In a further aspect, the present method comprises administering to a patient a composition comprising a pharmaceutical active agent and a carrier vehicle, wherein a pharmaceutically active moiety pharmacokinetic profile comprises three phases: an increasing phase in which the plasma concentration of pharmaceutically active moiety increases from about 0 ng/mL before administration to at least 5 ng/mL, per 100 mg of pharmaceutical active agent administered, at 24 hours after administration, a steady phase ranging from 24 hours after administration to about 6 days after administration in which the plasma concentration of pharmaceutically active moiety ranges from about 5 ng/mL to about 35 ng/mL, per 100 mg of pharmaceutical active agent administered, and a final phase starting at about 6 days after administration in which the plasma concentration of pharmaceutically active moiety increases before decreasing through at least about 28 days after administration.

In yet another aspect, the present method comprises administering to a patient a composition comprising a pharmaceutical active agent and a carrier vehicle, wherein a pharmaceutical active agent pharmacokinetic profile comprises three phases: an increasing phase in which the plasma concentration of pharmaceutical active agent increases from about 0 ng/mL before administration to at least 2 ng/mL, per 100 mg of pharmaceutical active agent administered, at about 24 hours after administration, a steady phase ranging from 24 hours after administration to about 6 days after administration in which the plasma concentration of pharmaceutical active agent ranges from about 2 ng/mL to 15 ng/mL, per 100 mg of pharmaceutical active agent administered, and a final phase starting at about 6 days after administration in which the plasma concentration of pharmaceutical active agent increases before decreasing through at least about 28 days after administration.

In another aspect, the present disclosure involves a method of reducing phase separation, comprising combining a pharmaceutical active agent with a means for achieving the reduction of phase separation.

In a further aspect, the present disclosure involves a process comprising: wet milling a pharmaceutical active agent in an aqueous solution at less than 20° C. to form a milled pharmaceutical active agent; maintaining the milled pharmaceutical active agent at less than 5° C.; and lyophilizing the milled pharmaceutical active agent to form a lyophilized pharmaceutical active agent having a median particle size, as measured by laser diffraction, of less than 5 micrometers.

In another aspect, a suspension is produced by wet milling a pharmaceutical active agent in an aqueous solution at less than 20° C. to form a milled pharmaceutical active agent; maintaining the milled pharmaceutical active agent at less than 5° C.; and lyophilizing the milled pharmaceutical active agent to form a lyophilized pharmaceutical active agent having a median particle size, as measured by laser diffraction, of less than 5 micrometers.

In another aspect, a monophasic composition, comprises 25 wt % to 80 wt %, based on total weight of the composition, of sucrose acetate isobutyrate; a poly(lactic acid) (glycolic acid) comprising an alkoxy end group wherein the alkoxy end group consists of 12 carbons, the poly(lactic acid)(glycolic acid) having a lactic acid to glycolic acid molar ratio of at least 70:30; and an organic solvent that maintains the composition monophasic at 25° C. and 1 atmosphere.

The pharmaceutical active agent may be dissolved or suspended in the composition. The particles comprising pharmaceutical active agent, which are used to make the disclosed compositions, typically have a median particle size, as measured by laser diffraction, ranging from 0.1 micrometer to 100 micrometers, such as 0.2 micrometer to 50 micrometers, 0.25 micrometer to 50 micrometers, 0.1 micrometer to 25 micrometers, 0.1 micrometer to 10 micrometer, 0.2 micrometer to 10 micrometers, 0.5 micrometers to 10 micrometers, 0.5 micrometer to 7 micrometers, or 1 micrometer to 5 micrometers.

When particles are relatively large, e.g., median particle size, as measured by laser diffraction, above 10 micrometers, the particles have a tendency to fall out of suspension in lower viscosity formulations. When particles are relatively small, the particle size may change due to recrystallization, which affects the storage time dependence of the release profile.

In the context of the present disclosure, the median particle size, as measured by laser diffraction, refers to the size of the particles before addition with the vehicle. Thus, the recited compositions are "made from" or "obtainable by combining" the particles comprising the pharmaceutical active agent and the one or more further specified components.

In some cases, the pharmaceutical active agent has a solubility in the composition at 25° C. of less than about 100 mg/mL, such as less than about 50 mg/mL, less than about 10 mg/mL, less than about 5 mg/mL, less than about 1 mg/mL, or less than about 0.1 mg/mL.

In one aspect, the pharmaceutical active agent comprises at least one member selected from peptide, protein, antibody, carbohydrate, small molecule, nucleic acid, and nucleoside.

Representative pharmaceutical active agents include drug, peptide, protein, carbohydrate (including monosaccharides, oligosaccharides, and polysaccharides), nucleoprotein, mucoprotein, lipoprotein, synthetic polypeptide or protein, or a small molecule linked to a protein, antibody, glycoprotein, steroid, nucleic acid (any form of DNA, including cDNA, or RNA, or a fragment thereof), nucleotide, nucleoside, oligonucleotides (including antisense oligonucleotides), gene, lipid, hormone, mineral supplement, vitamin including vitamin C and vitamin E, or combinations of any of the above, that cause(s) a biological effect when administered in vivo to an animal, including but not limited to birds and mammals, including humans.

Drug means any substance used internally or externally as a medicine for the treatment, cure, or prevention of a disease or disorder, and includes but is not limited to immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, antipsychotics, and radiation absorbers, including UV-absorbers.

In one embodiment disclosed herein, the pharmaceutical active agent is a vaccine and the substance to be delivered is an antigen. The antigen can be derived from a cell, bacteria, or virus particle, or portion thereof. As defined herein, antigen may be a protein, peptide, polysaccharide, glycoprotein, glycolipid, nucleic acid, or combination thereof, which elicits an immunogenic response in an animal, for example, a mammal, bird, or fish. As defined herein, the immunogenic response can be humoral or cell-mediated. In the event the material to which the immunogenic response is to be directed is poorly antigenic, it may be conjugated to a carrier such as albumin or to a hapten, using standard covalent binding techniques, for example, with one of the several commercially available reagent kits.

Examples of antigens include viral proteins such as influenza proteins, human immunodeficiency virus (HIV) proteins, and hepatitis A, B, or C proteins, and bacterial proteins, lipopolysaccharides such as gram negative bacterial cell walls and *Neisseria* gonorrhea proteins, and parvovirus.

Non-limiting examples of pharmaceutical active agents include anti-infectives such as nitrofurazone, sodium propionate, antibiotics, including penicillin, tetracycline, oxytetracycline, chlorotetracycline, bacitracin, nystatin, streptomycin, neomycin, polymyxin, gramicidin, chloramphenicol, erythromycin, and azithromycin; sulfonamides, including sulfacetamide, sulfamethizole, sulfamethazine, sulfadiazine, sulfamerazine, and sulfisoxazole, and anti-virals including idoxuridine; antiallergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; vaccines such as smallpox, yellow fever, distemper, hog cholera, chicken pox, antivenom, scarlet fever, dyptheria toxoid, tetanus toxoid, pigeon pox, whooping cough, *influenzae*, rabies, mumps, measles, poliomyelitic, and Newcastle disease; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl) urea, carbromal; psychic energizers such as 3-(2-aminopropyl) indole acetate and 3-(2-aminobutyl) indole acetate; tranquilizers such as reserpine, chlorpromayline, and thiopropazate; androgenic steroids such as methyltestosterone and fluorymesterone; estrogens such as estrone, 17-.beta.-estradiol, ethinyl estradiol, and diethyl stilbestrol; progestational agents such as progesterone, megestrol, melengestrol, chlormadinone, ethisterone, norethynodrel, 19-norprogesterone, norethindrone, medroxyprogesterone and 17-.beta.-hydroxy-progesterone; humoral agents such as the prostaglandins, for example PGE.sub.1, PGE.sub.2 and PGF.sub.2; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine, antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; antipsychotics including typical and atypical antipsychotics, wherein the atypical antipsychotics comprise risperidone, paliperidone, or olanzapine; nutritional agents such as vitamins, natural and synthetic bioactive peptides and proteins, including growth factors, cell adhesion factors, cytokines, and biological response modifiers; together with pharmaceutically acceptable salts of the above.

The pharmaceutical active agent is typically included in the composition in an amount sufficient to deliver to the host animal or plant an effective amount to achieve a desired effect. The amount of pharmaceutical active agent incorporated into the composition depends upon the desired release profile, the concentration of pharmaceutical active agent required for a biological effect, and the desired period of release of the pharmaceutical active agent.

The concentration of pharmaceutical active agent in the composition will also depend on absorption, inactivation, and excretion rates of the pharmaceutical active agent as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the disclosed compositions, and that the concentration ranges set forth herein are exemplary only and are not intended to limit the scope or practice of the present disclosure. The compositions may be administered in one dosage, or may be divided into a number of smaller doses to be administered at varying intervals of time.

In some cases, the pharmaceutical active agent comprises an antipsychotic, such as an atypical antipsychotic. Examples of anti-psychotic drugs include, but are not limited to metabotropic glutamate receptor 2 agonists, glycine transporter 1 inhibitors, partial agonists of dopamine receptors, chlorpromazine, fluphenazine, mesoridazine, perphenazine, prochlorperazine, promazine, thioridazine/sulforidazine, trifluoperazine, butyrophenones (azaperone, benperidol, droperidol, haloperidol), thioxanthenes (flupentixol, chlorprothixene, thiothixene, zuclopenthixol), diphenylbutylpiperidines (fluspirilene, penfluridol, pimozide, loxapine), butyrophenones (melperone), indoles (sertindole, ziprasidone, molidone), benzamides (sulpiride, remoxipride, amisulpride), diazepines/oxazepines/thiazepines (clozapine, olanzapine, quetiapine), aripiprazole, risperidone, paliperidone, zotepine), amisulpride, asenapine, iloperidone, lurasidone, cannabidiol, tetraenazine, and L-theanine, including pharmaceutically acceptable salts, solvates, bases, and ester forms thereof. Combinations of two or more of these compounds, or combinations with other compounds are included in the scope of the disclosure.

For instance, the pharmaceutical active agent may comprise at least one member selected from chlorpromazine, fluphenazine, mesoridazine, perphenazine, prochlorperazine, promazine, thioridazine, sulforidazine, trifluoperazine, molindone, azaperone, benperidol, droperidol, haloperidol, flupentixol, chlorprothixene, thiothixene, zuclopenthixol, fluspirilene, penfluridol, pimozide, loxapine, melperone, sertindole, ziprasidone, sulpiride, remoxipride, amisulpride, clozapine, olanzapine, quetiapine, aripiprazole, risperidone, paliperidone, zotepine, amisulpride, asenapine, iloperidone, lurasidone, cannabidiol, tetraenazine, and L-theanine, or pharmaceutically acceptable salt thereof. In some cases, the pharmaceutical active agent comprises risperidone or pharmaceutically acceptable salt thereof or pharmaceutically acceptable ester thereof.

Exemplary salts include hydrochloride, phosphate, citrate, maleate, mesylate, pamoate, and naphthaline-2-sulfonate monohydrate. For instance, representative salts include risperidone pamoate, and risperidone naphthaline-2-sulfonate. In some cases, the salt is lipophilic. An exemplary ester is paliperidone palmitate.

The pharmaceutical active agent is typically present in the compositions in the range from 0.5 wt % to 50 wt %, such as 0.5 wt % to 30 wt %, 1 wt % to 25 wt %, 1 wt % to 20 wt %, 2 wt % to 20 wt %, 5 wt % to 20 wt %, 5 wt % to 25 wt %, 8 wt % to 20 wt %, 10 wt % to 20 wt %, or 15 wt % to 20 wt %, based on total weight of the composition. For potent pharmaceutical active agents, such as growth factors, typical ranges include less than 1 wt %, and further even less than 0.0001 wt %.

The compositions can include one or more non-polymeric, non-water soluble high viscosity liquid carrier material (HVLCM) having a viscosity of at least 5000 cP at 37° C. that does not crystallize neat at 25° C. and 1 atmosphere. For instance, the HVLCM may have a viscosity of at least at least 10,000 cP, at least 15,000 cP, at least 20,000 cP, at least 25,000 cP, or at least 50,000 cP, at 37° C. The term non-water soluble refers to a material that is soluble in water to a degree of less than one percent by weight under ambient conditions.

In some cases, the HVLCM significantly decreases in viscosity when mixed with a solvent to form a low viscosity liquid carrier material ("LVLCM") that can be mixed with a substrate for controlled delivery. The LVLCM/substrate composition is typically easier to place in the body than a HVLCM/substrate composition, because it flows more easily into and out of syringes or other implantation means, and can easily be formulated as an emulsion. The LVLCM can have any desired viscosity. It has been found that a viscosity range for the LVLCM of less than approximately 2000 cP, such as less than 1000 cP, at a shear rate 200 $s^{-1}$ at 25° C., is typically useful for in vivo applications.

In one embodiment, sucrose acetate isobutyrate ("SAIB"), a sucrose molecule nominally esterified preferably with two acetic acid and six isobutyric acid moieties, is used as the HVLCM.

SAIB is orally non-toxic and is currently used as to stabilize emulsions in the food industry. It is a very viscous liquid and has an unusual property that there is a dramatic change in viscosity with small additions of heat or with the addition of solvents. It is soluble in a large number of biocompatible solvents. When in solution or in an emulsion, SAIB can be applied via injection or an aerosol spray. SAIB is compatible with cellulose esters and other polymers that can affect the rate of delivery of the substance.

In some embodiments of the disclosure, the HVLCM can be stearate esters such as those of propylene glycol, glyceryl, diethylaminoethyl, and glycol, stearate amides and other long-chain fatty acid amides, such as N,N'-ethylene distearamide, stearamide MEA and DEA, ethylene bistearamide, cocoamine oxide, long-chain fatty alcohols, such as cetyl alcohol and stearyl alcohol, long-chain esters such as myristyl myristate, beheny erucate, and glyceryl phosphates. In a particular embodiment, the HVLCM is acetylated sucrose distearate (Crodesta A-10). Additional materials suitable for use as the HVLCM are disclosed in US Patent Application Publication US 2004/0101557 by Gibson et al.

The amount of HVLCM in a composition will depend on the desired properties of a composition and the solvent capacity of the chosen solvent. If the chosen solvent has poor solvent capacity performance, then the actual amount of solvent may be large, with a corresponding reduction in the amount of HVLCM in the composition. The HVLCM is typically present in controlled delivery compositions in an amount ranging from about 10 wt % to about 99.5 wt %, such as from 25 wt % to 95 wt %, from 25 wt % to 85 wt %, from 30 wt % to 60 wt %, and from 45 wt % to 55 wt %, relative to the total weight of the composition.

The compositions can include one or more polymer, such as a lactic-acid based polymer. The lactic-acid based polymer is typically biodegradable and biocompatible.

The lactic-acid based polymer can be used to alter the release profile of the pharmaceutical active agent to be delivered, to add integrity to the composition, or to otherwise modify the properties of the composition.

An exemplary property of the composition is the miscibility or solubility of the polymer in the composition with the HVLCM. In situations where the polymer is not miscible or soluble in the composition with the HVLCM, phase separation of the polymer and the HVLCM may occur. Once this occurs, it may be very difficult to remix the polymer and the HVLCM, especially at the point of use. Should improper remixing of the composition occur, it might not release drug in a desired manner. Additionally, the compositions might be difficult to administer. Accordingly, compositions that have high miscibility or solubility of the polymer in the composition with the HVLCM are desirable.

The lactic-acid based polymer may be linear or branched. The lactic acid-based polymer may be unsaturated or saturated.

The lactic-acid based polymer may comprise a homopolymer, i.e., poly(lactic acid), which includes polylactide for purposes of the present disclosure.

Alternatively, the lactic acid-based polymer may comprise a copolymer. In addition to lactic acid, the polymer may also comprise repeat units of other suitable materials, including but not limited to glycolic acid repeat units, glycolide repeat units, polyethylene glycol repeat units, caprolactone repeat units, valerolactone repeat units, and the like.

For instance, the lactic acid-based polymer may comprise poly(lactic acid)(glycolic acid), which includes poly(lactide) (glycolide) for purposes of the present disclosure.

The poly(lactic acid)(glycolic acid) typically has a lactic acid to glycolic acid molar ratio ranging from 100:0 to 40:60, such as from 95:5 to 60:40, 65:35 to 90:10, or 75:25 to 85:15. In some cases, the poly(lactic acid)(glycolic acid) has a lactic acid to glycolic acid molar ratio greater than 65:35, such as greater than 70:30, or greater than 75:25. Polymers with higher L:G ratio tend to be more compatible with sucrose acetate isobutyrate and tend to provide longer release profiles.

The lactic acid-based polymer typically has a weight average molecular weight ranging from 1000 Daltons to 30,000 Daltons, such as from 4000 Daltons to 15,000 Daltons, further such as from 5000 Daltons to 30,000 Daltons, 6000 Daltons to 30,000 Daltons, or 7000 Daltons to 30,000 Daltons, even further such as 5000 Daltons to 15,000 Daltons, 6000 Daltons to 15,000 Daltons, or 7000 Daltons to 15,000 Daltons, and as an even further example, from 5000 Daltons to 10,000 Daltons. The weight average molecular weight may be less than or equal to about 15,000 Daltons, such as less than or equal to about 12,500 Daltons, or less than or equal to about 10,000 Daltons. Polymers with lower molecular weight tend to be more miscible with sucrose acetate isobutyrate and tend to provide shorter release profiles.

The lactic acid-based polymer may have an alkoxy end group. For instance, the lactic acid-based polymer may comprise an alkoxy end group that consists of 8 to 24 carbons, such as 12 carbons.

Initiators for the polymers include but are not limited to diol initiators including 1,6-hexanediol, 1,2-propanediol, 1,3-propanediol, 1,4-butanediol and the like; diol initiators including difunctional poly(ethylene glycol)s (PEGs); monofunctional alcohol initiators including 1-dodecanol, methyl lactate, ethyl lactate and the like; monofunctional PEGs including methoxy(polyethylene glycol) (mPEG); and other initiators including water, glycolic acid, lactic acid, citric acid, and the like. In some cases, the lactic acid-based polymer is initiated with a member selected from fatty alcohol and diol. For instance, the lactic-acid based polymer may be initiated with 1,6-hexanediol or with dodecanol.

Compositions including polymers initiated dodecanol tend to provide a larger region of solubility than compositions including the polymer initiated with 1-hexanediol. As a result, compositions including polymer initiated with dodecanol, which results in a polymer having an alkoxy end group (which consists of 12 carbons), can require less solvent and/or can tend to be more resistant to phase separation.

Surprisingly, compositions comprising polymers comprising alkoxy end group and made from small drug particles, e.g., median particle size, as measured by laser diffraction, of 10 μm or less, can have lower drug burst in vivo relative to compositions using other polymers. For example, compositions comprising dodecanol-initiated PLGA and made from risperidone in the form of small particles were shown to have a lower drug burst than compositions based on hexanediol-initiated PLGA. The lactic acid-based polymer is typically present in an amount ranging from 1 wt % to 50 wt %, such as from 1 wt % to 45 wt %, from 5 wt % to 35 wt %, from 5 wt % to 30 wt %, from 5 wt % to 25 wt %, from 10 wt % to 25 wt %, from 15 wt % to 45 wt %, or such as from 15 wt % to about 35 wt %, based on total weight of the composition.

The polymers of the present invention may be made using techniques that are generally known in the art. For instance, a polylactide initiated with a monoalcohol may be synthesized according to the following:

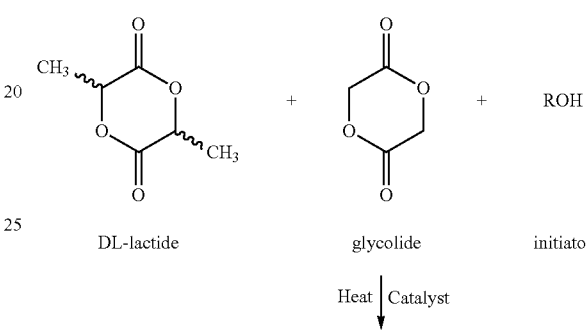

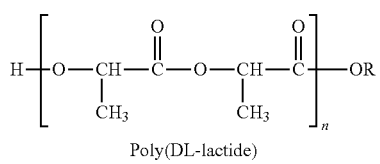

Poly(DL-lactide)

R = alkyl

A poly(lactide)(glycolide) initiated with a monoalcohol may be synthesized according to the following:

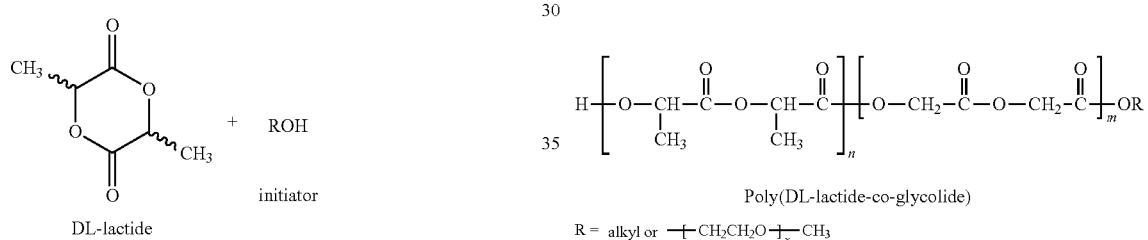

Poly(DL-lactide-co-glycolide)

R = alkyl or —(CH$_2$CH$_2$O)$_x$—CH$_3$

A polylactide initiated with a diol may be synthesized according to the following:

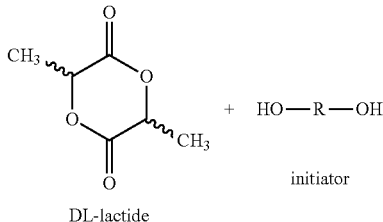

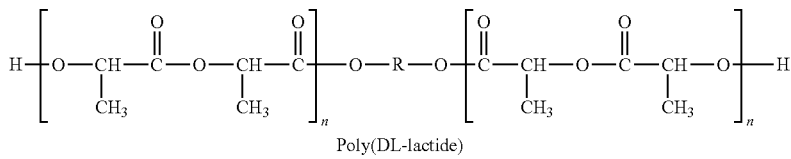

Poly(DL-lactide)

R = alkyl

A polylactide initiated with water or an acid may be synthesized according to the following:

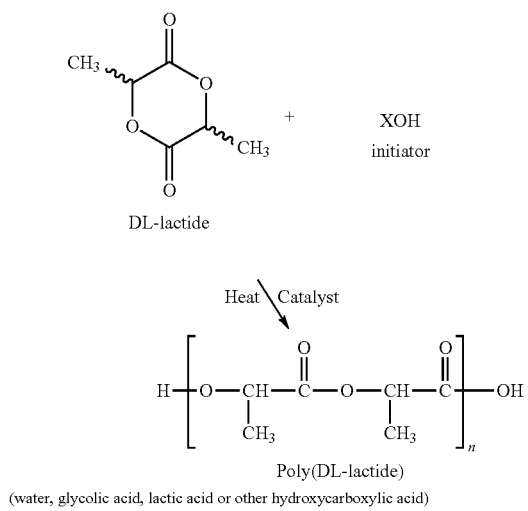

Poly(DL-lactide)
(water, glycolic acid, lactic acid or other hydroxycarboxylic acid)

The compositions can include one or more organic solvents. Solvents used in the practice of the present disclosure are typically biocompatible, polar, non-polar, hydrophilic, water miscible, water soluble, and/or non-toxic. In some embodiments, the pharmaceutical active agent is soluble in the solvent. The solvents used to inject the disclosed compositions into animals should not cause significant tissue irritation or necrosis at the site of implantation, unless irritation or necrosis is the desired effect.

The solvent is typically water miscible and/or water soluble, so that it will diffuse into bodily fluids or other aqueous environment, causing the composition to assume a more viscous form. Certain solvents that are not water miscible and/or not water soluble may also be used in the practice of the disclosure.

The one or more solvents should be biocompatible, which may eliminate some solvents from use in the disclosed compositions. In an embodiment, the one or more solvents should be good solvents for both the polymer and HVLCM.

The solvent may comprise at least one member selected from N-methyl-pyrrolidone (NMP), dimethylsulfoxide (DMSO), propylene carbonate (PC), benzyl alcohol (BA), benzyl benzoate (BB), dimethylacetamide, caprylic/capric triglyceride, polyoxyethylene ester of 12-hydroxystearic acid, ethanol, ethyl lactate, glycofurol, propylene glycol, acetone, methyl acetate, ethyl acetate, methyl ethyl ketone, triacetin, dimethylformamide, tetrahydrofuran, caprolactam, decylmethylsulfoxide, oleic acid, tocopherol, linoleic acid, oleic acid, ricinoleic acid, pyrrolidone, diethyl phthalate, isopropylidene glycerol, and 1-dodecylazacycloheptan-2-one. In some cases, the solvent comprises at least one member selected from N-methyl-pyrrolidone (NMP), dimethylsulfoxide (DMSO), propylene carbonate (PC), benzyl benzoate (BB), di methylacetamide, caprylic/capric triglyceride, polyoxyethylene ester of 12-hydroxystearic acid, ethanol, ethyl lactate, glycofurol, propylene glycol, acetone, methyl acetate, ethyl acetate, methyl ethyl ketone, triacetin, dimethylformamide, tetrahydrofuran, caprolactam, decylmethylsulfoxide, oleic acid, tocopherol, linoleic acid, oleic acid, ricinoleic acid, pyrrolidone, diethyl phthalate, isopropylidene glycerol, and 1-dodecylazacycloheptan-2-one. In some cases, the solvent comprises N-methyl-pyrrolidone. In other cases, the solvent comprises DMSO.

In still other cases, the solvent comprises propylene carbonate. Propylene carbonate improves the settling and allows longer shelf life and storage at refrigerated conditions of 2-8° C.

When SAIB is used as the HVLCM, the typical solvents include ethanol, dimethylsulfoxide, ethyl lactate, ethyl acetate, benzyl alcohol, triacetin, N-methylpyrrolidone, propylene carbonate, and glycofurol. Particularly preferred solvents include ethanol, dimethylsulfoxide, ethyl lactate, ethyl acetate, triacetin, N-methylpyrrolidone, propylene carbonate, and glycofurol. SAIB is not miscible with glycerol, corn oil, peanut oil, 1,2-propanediol, polyethylene glycol (PEG200), super refined sesame oil, and super refined peanut oil. Accordingly, the latter group of solvents is not preferred for use with SAIB.

In certain cases, the solvent is not an alcohol. For instance, in some cases, the solvent is not ethanol. In other cases, the solvent is not benzyl alcohol. Thus, the composition may be free of alcohol, ethanol, and/or benzyl alcohol.

The solvent typically has a solvent capacity of greater than or equal to 25%, such as greater than or equal to 20%, greater than or equal to about 15%, or greater than or equal to about 10%.

The solvent is typically present in an amount ranging from 1 wt % to 60 wt %, such as from 1 wt % to 50 wt %, 1 wt % to 40 wt %, 5 wt % to 35 wt %, 5 wt % to 30 wt %, 10 wt % to 50 wt %, or 20 wt % to 40 wt %, based on total weight of the composition. Minimizing total solvent content of the compositions is generally biologically desirable. Increasing solvent content, however, can move a HVLCM/linear polymer/solvent composition from phase separation to single phase behavior.

In some embodiments, a weight ratio of the HVLCM to the lactic acid-based polymer to the solvent ranges from 1:0.066-1.3:0.3-1.7, such as 1:0.25-0.5:0.4-0.8.

In one embodiment of the disclosure, a composition comprises 5 wt % to 20 wt %, based on total weight of the composition, of particles comprising a pharmaceutical active agent that is risperidone or a pharmaceutically acceptable salt thereof, the particles having a median particle size, as measured by laser diffraction, ranging from 0.5 micrometer to 7 micrometers; and the composition further comprises from 30 wt % to 60 wt %, based on total weight of the composition, of sucrose acetate isobutyrate; from 5 wt % to 30 wt %, based on total weight of the composition, of a lactic acid based-polymer that is poly(lactic acid)(glycolic acid) comprising an alkoxy end group, the poly(lactic acid)(glycolic acid) having a lactic acid to glycolic acid molar ratio ranging from 95:5 to 60:40, the poly(lactic acid)(glycolic acid) having a weight average molecular weight ranging from 4000 Daltons to 15,000 Daltons; and 10 wt % to 40 wt %, based on total weight of the composition, of a solvent that is at least one member selected from N-methyl-pyrrolidone, propylene carbonate, and dimethylsulfoxide.

A variety of additives can optionally be included in the compositions to modify the properties of the compositions as desired. The additives can be present in any amount that is sufficient to impart the desired properties to the compositions. The amount of additive used will in general be a function of the nature of the additive and the effect to be achieved, and can be easily determined by one of skill in the art.

When present, additive(s) are typically present in the compositions in an amount in the range from about 0.1 percent to about 20 percent by weight, relative to the total weight of the composition, and more typically, is present in the composition in an amount in the range from about 1, 2, or 5 percent to about 10 percent by weight, relative to the total weight of the composition. Certain additives, such as buffers, may be present only in small amounts in the relative to the total weight of the composition.

Another additive for use with the present compositions are non-biodegradable polymers. Non-limiting examples of non-erodible polymers which can be used as additives include: polyacrylates, ethylene-vinyl acetate polymers, cellulose and cellulose derivatives, acyl substituted cellulose acetates and derivatives thereof, non-erodible polyurethanes, polystyrenes, polyvinyl chloride, polyvinyl fluoride, poly(vinyl imidazole), chlorosulphonated polyolefins, and polyethylene oxide.

Exemplary non-biodegradable polymers include polyethylene, polyvinyl pyrrolidone, ethylene vinylacetate, polyethylene glycol, cellulose acetate butyrate ("CAB") and cellulose acetate propionate ("CAP").

A further class of additives which can be used in the disclosed compositions are natural and synthetic oils and fats. Oils derived from animals or from plant seeds of nuts typically include glycerides of the fatty acids, chiefly oleic, palmitic, stearic, and linolenic. As a rule the more hydrogen the molecule contains, the thicker the oil becomes.

Non-limiting examples of suitable natural and synthetic oils include vegetable oil, peanut oil, medium chain triglycerides, soybean oil, almond oil, olive oil, sesame oil, peanut oil, fennel oil, *camellia* oil, corn oil, castor oil, cotton seed oil, and soybean oil, either crude or refined, and medium chain fatty acid triglycerides.

Fats are typically glyceryl esters of higher fatty acids such as stearic and palmitic. Such esters and their mixtures are solids at room temperatures and exhibit crystalline structure. Lard and tallow are examples. In general oils and fats increase the hydrophobicity of the composition, slowing degradation and water uptake.

Another class of additives which can be used in the disclosed compositions comprise carbohydrates and carbohydrate derivatives. Non-limiting examples of these compounds include monosaccarides (simple sugars such as fructose and its isomer glucose (dextrose); disaccharides such as sucrose, maltose, cellobiose, and lactose; and polysaccarides.

Other additives, such as preservatives, stabilizers, antioxidants, coloring agents, isotonic agents, humectants, sequesterants, vitamins and vitamin precursors, surfactants and the like, may be added as needed. Examples of preservatives include paraben derivatives, such as methyl paraben and propyl paraben. Examples of anti-oxidants include butyl hydroxyanisole, butyl hydroxytoluene, propyl gallate, vitamin E acetate, and purified hydroquinone. Humectants include sorbitol. Sequesterants include citric acid.

In some aspects, the composition may further comprise at least one member selected from viscosity enhancers, antioxidants, preservatives, and particle stabilizers. For instance, the composition may comprise at least one member selected from ricinoleic acid, polyoxyethylene-polyoxypropylene block copolymer, polyvinylpyrrolidone, polyethyeleneglycol (e.g., PEG4000), and Cremophor EL® ethoxylated castor oil which includes polyethylene glycol ether.

As noted above, an aspect of the compositions according to the present disclosure is the miscibility or solubility of the polymer in the composition with the HVLCM. In situations where the polymer is not miscible or soluble in the composition with the HVLCM, phase separation of the polymer and the HVLCM in the composition may occur. Once this occurs, it may be very difficult to remix the polymer and the HVLCM, especially at the point of use. Should improper or no remixing occur, undesirably wide variations in release performance might result. Accordingly, compositions that have high miscibility or solubility of the polymer in the composition with the HVLCM are desirable.

The present compositions typically possess high miscibility or solubility of the polymer in the composition with the HVLCM. In one aspect of the disclosure, the composition may comprise the HVLCM, the polymer, one or more good solvents for the polymer, and one or more good solvents for the HVLCM, with the resultant composition being a single phase.

Solubility and phase separation of various HVLVM/linear polymer/solvent composition may be investigated by visual techniques well known to those skilled in the art. For compositions with significant instability or tendency to phase-separate, the linear polymer may absorb solvent but remain as a separated, very viscous layer or phase in the composition. Other compositions might be rendered into a uniform clear solution by sufficient heating and mixing. However, when cooled to room temperature, two clear liquid phases may form. Sometimes, the two clear layers may not be easy to detect, thus requiring strong light and a thorough inspection of the composition to discern the boundary between the two phases. In a number of cases, compositions may appear clear and uniform on initial cooling to room temperature, but when left quiescent at room temperature for a period of several days or greater, the compositions may separate into two phases. For compositions that are at the border of phase separation, the composition may turn cloudy and sometimes slowly separate into two phases.

The HVLCM, the lactic acid-based polymer, and the solvent are typically monophasic when stored at 25° C. for a period of time, such as 7 days, for 1 month, for 24 months, or longer.

In one embodiment, the composition is monophasic and comprises: from 25 wt % to 80 wt %, based on total weight of the composition, of sucrose acetate isobutyrate; a poly (lactic acid)(glycolic acid) comprising an alkoxy end group wherein the alkoxy end group consists of 12 carbons, the poly(lactic acid)(glycolic acid) having a lactic acid to glycolic acid molar ratio of at least 70:30; and an organic solvent that maintains the composition monophasic at 25° C. and 1 atmosphere.

In another aspect of the disclosure, a method of reducing phase separation comprises combining: a pharmaceutical active agent, a non-polymeric, non-water soluble high viscosity liquid carrier material (HVLCM) having a viscosity of at least 5000 cP at 37° C. that does not crystallize neat at 25° C. and 1 atmosphere; a lactic acid-based polymer; and an organic solvent.

In another aspect of the disclosure, a method of reducing phase separation, comprises combining: a pharmaceutical active agent with a means for achieving the reduction of phase separation.

The composition typically has a viscosity of less than 5000 cP at a shear rate of 50 $s^{-1}$ at 25° C., less than 3000 cP at a shear rate of 100 $s^{-1}$ at 25° C., or less than 3000 cP at a shear rate of 200 $s^{-1}$ at 25° C. For instance, the viscosity may range from 50 cP to 2000 cP at a shear rate of 150 $s^{-1}$ at 25° C., 50 cP to 2000 cP at a shear rate of 200 $s^{-1}$ at 25° C., 200 cP to 1800 cP at a shear rate of 500 $s^{-1}$ at 25° C., 300 cP to 1700 cP at a shear rate of 500 $s^{-1}$ at 25° C. or 500 cP to 1500 cP at a shear rate of 200 $s^{-1}$ at 25° C.

In one aspect, the composition comprises a pharmaceutical active agent that is risperidone or a pharmaceutically acceptable salt thereof; and means for extending a release profile of the pharmaceutical active agent when the composition is administered to a patient in need thereof.

In another aspect of the disclosure, the composition comprises a pharmaceutical active agent that is risperidone or a pharmaceutically acceptable salt thereof; and a non-polymeric, non-water soluble high viscosity liquid carrier material (HVLCM) having a viscosity of at least 5000 cP at 37° C. that does not crystallize neat at 25° C. and 1 atmosphere, a lactic acid-based polymer comprising an alkoxy end group, and an organic solvent in a ratio sufficient to maintain a therapeutically effective plasma concentration of the risperidone or pharmaceutically acceptable salt thereof for a period of at least 7 days when the composition is administered subcutaneously as a single dose to a human patient. The period may be at least 14 days, such as at least 21 days, at least 28 days, or at least 84 days.

In another aspect, the composition comprises risperidone or pharmaceutically acceptable salt thereof; and a non-polymeric, non-water soluble high viscosity liquid carrier material (HVLCM) having a viscosity of at least 5000 cP at 37° C. that does not crystallize neat at 25° C. and 1 atmosphere, a lactic acid-based polymer comprising an alkoxy end group, and an organic solvent in a ratio such that when the composition is administered subcutaneously as a single dose to a human patient, a median amount of pharmaceutical active agent released from the composition provides an AUC (0 to 1 day) that is less than 20%, such as less than 15%, less than 10%, or less than 5%, of AUC (0 to 28 days).

In yet another aspect, the composition comprises a pharmaceutical active agent, wherein when the composition is administered subcutaneously as a single dose, a median amount of pharmaceutical active agent released from the composition at 4 weeks of administration to a human patient ranges from 20% to 100%, such as 20% to 75%, 30% to 60%, or 40% to 50%, of a total amount of the pharmaceutical active agent in the composition.

In one aspect of the disclosure, the composition comprises a pharmaceutical active agent, wherein when the composition is placed in phosphate buffered saline at 37° C., an amount of pharmaceutical active agent released from the composition at 4 weeks of placement in the phosphate buffered saline ranges from 20% to 100%, such as 30% to 90%, 40% to 80%, or 50% to 70%, of a total amount of the pharmaceutical active agent in the composition.

In yet another aspect of the disclosure, the composition comprises a pharmaceutical active agent, wherein when the composition is placed in phosphate buffered saline at 37° C., an amount of pharmaceutical active agent released from the composition at 24 hours after placement in the phosphate buffered saline is less than 20%, such as less than 15%, less than 10%, or less than 5%, of an amount released at 28 days. Further, the amount of pharmaceutical active agent released at 28 days after placement in the phosphate buffered saline at 37° C. may be greater than 50%, such as greater than 60%, or greater than 70%, of a total amount of pharmaceutical active agent in the composition.

In another aspect of the disclosure, the composition comprises a pharmaceutical active agent, wherein when the composition is administered subcutaneously as a single dose to a human patient, a median amount of pharmaceutical active agent released from the composition provides an AUC (0 to 1 day) that is less than 20%, such as less than 15%, less than 10%, or less than 5%, of AUC (0 to 28 days).

In still another aspect, the composition comprises a pharmaceutical active agent, wherein when the composition is administered subcutaneously as a single dose to a human patient, a median amount of pharmaceutical active agent released from the composition provides an AUC (0 to 1 day) that is less than 20%, such as less than 10%, or less than 5%, of AUCinf.

In another aspect, the composition comprises a pharmaceutical active agent; and a carrier vehicle, wherein when 1 mL of the composition is administered as a single dose subcutaneously to a human patient: median AUC (0 to 5 hours) of pharmaceutically active moiety is less than 10%, such as less than 8% or less than 5%, of median AUC (0 to 28 days), median AUC (5 hours to 7 days) of pharmaceutically active moiety ranges from 10% to 80%, such as 15% to 75% or 20% to 70%, of median AUC (0 to 28 days), and median AUC (7 days to 28 days) of pharmaceutically active moiety ranges from 10% to 80%, such as 15% to 75% or 20% to 70%, of median AUC (0 to 28 days). In some cases, the pharmaceutically active moiety consists of risperidone and 9-hydroxyrisperidone. Although the compositions are typically in the form of a liquid, they may be in the form of a solid. Thus, administration of 1 mL of the composition may refer to the volume of a solid, wherein the volume of the solid excludes pores.

In another aspect, the composition comprises a pharmaceutical active agent; and a carrier vehicle, wherein when 1 mL of the composition is administered as a single dose subcutaneously to a human patient: median AUC (0 to 5 hours) of pharmaceutical active agent is less than 10%, such as less than 8% or less than 5%, of median AUC (0 to 28 days), median AUC (5 hours to 7 days) of pharmaceutical active agent ranges from 10% to 80%, such as 15% to 75% or 20% to 70%, of median AUC (0 to 28 days), and median AUC (7 days to 28 days) of pharmaceutical active agent ranges from 10% to 80%, such as 15% to 75% or 20% to 70%, of median AUC (0 to 28 days).

In yet another aspect, the composition comprises a pharmaceutical active agent; and a carrier vehicle, wherein when 1 mL of the composition is administered as a single dose subcutaneously to a human patient: the median plasma concentration of pharmaceutically active moiety increases, after the median plasma concentration of pharmaceutically active moiety increases, the median plasma concentration of pharmaceutically active moiety remains steady for a steady phase such that the median plasma concentration of pharmaceutically active moiety fluctuates less than ±30%, such as less than ±25%, for a period of at least 4 days, such as 4 days to 6 days, and after the median plasma concentration of pharmaceutically active moiety remains steady, the median plasma concentration of pharmaceutically active moiety increases, relative to an end of the steady phase, by an amount ranging from about 0% to about 40%, such as about 5% to about 35%, about 10% to about 30%, or 15% to 25%, before decreasing. In some cases, the pharmaceutically active moiety consists of risperidone and 9-hydroxyrisperidone.

In another aspect, the composition comprises a pharmaceutical active agent; and a carrier vehicle, wherein when 1 mL of the composition is administered as a single dose subcutaneously to a human patient: the median plasma concentration of pharmaceutical active agent increases, after the median plasma concentration of pharmaceutical active agent increases, the median plasma concentration of pharmaceutical active agent remains steady for a steady phase such that the median plasma concentration of pharmaceutical active agent fluctuates less than ±30%, such as less than ±25%, for a period of at least 4 days, such as 4 days to 6 days, and after the median plasma concentration of pharmaceutical active agent remains steady, the median plasma concentration of pharmaceutical active agent increases, relative to an end of the steady phase, by an amount ranging from about 5% to about 40%, such as about 5% to about 35%, about 10% to about 30%, or 15% to 25%, before decreasing.

In one aspect, the composition comprises a pharmaceutical active agent; and a carrier vehicle, wherein when 1 mL of the composition is administered as a single dose subcutaneously to a human patient: a median PK profile is described by 3 absorption phases: (1) a first absorption phase occurs immediately after administration, with a first order rate constant ranging from 0.1 $hr^{-1}$ to 0.4 $hr^{-1}$, such as 0.2 to 0.3 $hr^{-1}$; (2) a second absorption phase occurs after a time delay ranging from 2.5 hours to 8.5 hours, such as 4.5 hours to 6.5 hours, after administration, with a first order rate constant ranging from 0.0005 $hr^{-1}$ to 0.005 $hr^{-1}$, such 0.001 $hr^{-1}$ to 0.003 $hr^{-1}$; and (3) a third absorption phase occurs after a time delay ranging from 5 days to 10 days, such as 6 days to 9 days, after administration, with a first order rate constant ranging from 0.0005 $hr^{-1}$ to 0.005 $hr^{-1}$, such as 0.001 $hr^{-1}$ to 0.003 $hr^{-1}$.

In a further aspect, the composition comprises a pharmaceutical active agent; and a carrier vehicle, wherein when 1 mL of the composition is administered as a single dose subcutaneously to a human patient, the composition provides a median maximum blood plasma concentration (Cmax) of pharmaceutically active moiety ranging from about 70% to about 140%, such as 80% to 125% or 90% to 115%, of 25 ng/mL, per 100 mg of pharmaceutical active agent administered, and a median AUC (0 to 28 days) of pharmaceutically active moiety ranging from about 70% to about 140%, such as 80% to 125% or 90% to 115%, of 14,200 ng·hr/mL, per 100 mg of pharmaceutical active agent administered. In some cases, the pharmaceutically active moiety consists of risperidone and 9-hydroxyrisperidone.

In other aspects, the composition comprises a pharmaceutical active agent; and a carrier vehicle, wherein when 1 mL of the composition is administered as a single dose subcutaneously to a human patient, the composition provides a median maximum blood plasma concentration (Cmax) of pharmaceutical active agent ranging from about 70% to about 140%, such as 80% to 125% or 90% to 115%, of 11 ng/mL, per 100 mg of pharmaceutical active agent administered, and a median AUC (0 to 28 days) of pharmaceutical active agent ranging from about 70% to about 140%, such as 80% to 125% or 90% to 115%, of 3670 ng·hr/mL, per 100 mg of pharmaceutical active agent administered.

In one aspect, the composition comprises a pharmaceutical active agent; and a carrier vehicle, wherein when the composition is administered as a single dose subcutaneously to a human patient, the composition provides a median pharmacokinetic profile of pharmaceutically active moiety within ±20%, such as within ±15%, of the 100 mg dose profile of FIG. 30, per 100 mg of pharmaceutical active agent administered.

In another aspect, the composition comprises a pharmaceutical active agent; and a carrier vehicle, wherein when 1 mL of the composition is administered as a single dose subcutaneously to a human patient, the composition provides a pharmaceutically active moiety pharmacokinetic profile comprising: a median first peak during a first period ranging from 2 hours after the administration to 4 days after the administration, such as from 4 hours to 3 days after the administration, a median second peak during a second period ranging from 4 days after the administration to 14 days after the administration, such as from 5 days to 12 days after the administration, and a median trough between the median first peak and the median second peak, wherein the median plasma concentration of pharmaceutically active moiety at the trough ranges from 40% to 90%, such as 50% to 80%, of the median plasma concentration of pharmaceutically active moiety at the median second peak. In some cases, the median first peak ranges from about 15 ng/mL to about 25 ng/mL, such as from about 17 ng/mL to about 23 ng/mL, per 100 mg of pharmaceutical active agent administered. In some cases, the median second peak ranges from about 20 ng/mL to about 30 ng/mL, such as from about 22 ng/mL to about 28 ng/mL, per 100 mg of pharmaceutical active agent administered. In some cases, the pharmaceutically active moiety consists of risperidone and 9-hydroxyrisperidone.

In still another aspect, the composition comprises a pharmaceutical active agent; and a carrier vehicle, wherein when 1 mL of the composition is administered as a single dose subcutaneously to a human patient, the composition provides a pharmaceutical active agent pharmacokinetic profile comprising: a median first peak during a first period ranging from 2 hours after the administration to 4 days after the administration, such as from 4 hours to 3 days after the administration, a median second peak during a second period ranging from 4 days after the administration to 14 days after the administration, such as from 5 days to 12 days after the administration, and a median trough between the median first peak and the median second peak, wherein the median plasma concentration of pharmaceutical active agent at the trough ranges from 30% to 90%, such as 40% to 80% or 50% to 70%, of the median plasma concentration of pharmaceutical active agent at the median second peak. In some cases, the median first peak ranges from about 8 ng/mL to about 14 ng/mL, such as from about 9 ng/mL to about 13 ng/mL, per 100 mg of pharmaceutical active agent administered. In some cases, the second median peak ranges from about 4 ng/mL to about 10 ng/mL, such as from 5 ng/mL to about 9 ng/mL, per 100 mg of pharmaceutical active agent administered.

In one aspect, the composition comprises a pharmaceutical active agent; and a carrier vehicle, wherein when 1 mL of the composition is administered as a single dose subcutaneously to a human patient, the composition provides a pharmaceutically active moiety pharmacokinetic profile comprising three phases: an increasing phase in which the median plasma concentration of pharmaceutically active moiety increases from about 0 ng/mL before administration to at least 5 ng/mL, such as at least 10 ng/mL, per 100 mg of pharmaceutical active agent administered, at 24 hours after administration, a steady phase ranging from 24 hours after administration to about 6 days after administration in which the median plasma concentration of pharmaceutically active moiety ranges from about 5 ng/mL to about 35 ng/mL, such as from 10 ng/mL to about 30 ng/mL, per 100 mg of pharmaceutical active agent administered, and a final phase starting at about 6 days after administration in which the median plasma concentration of pharmaceutically active moiety increases before decreasing through at least about 28 days after administration. In some cases, the pharmaceutically active moiety consists of risperidone and 9-hydroxyrisperidone.

In some aspects, the composition comprises a pharmaceutical active agent; and a carrier vehicle, wherein when 1 mL of the composition is administered as a single dose subcutaneously to a human patient, the composition provides a pharmaceutical active agent pharmacokinetic profile comprising three phases: an increasing phase in which the median plasma concentration of pharmaceutical active agent increases from about 0 ng/mL before administration to at least 2 ng/mL, such as at least 5 ng/mL, per 100 mg of pharmaceutical active agent administered, at about 24 hours after administration, a steady phase ranging from about 24 hours after administration to about 6 days after administration in which the median plasma concentration of pharmaceutical active agent ranges from about 2 ng/mL to 15 ng/mL, such as about 5 ng/mL to 10 ng/mL, per 100 mg of pharmaceutical active agent administered, and a final phase starting at about 6 days after administration in which the plasma concentration of pharmaceutical active agent increases before decreasing through at least about 28 days after administration.

In one embodiment of the disclosure, a method of improving reproducibility of a release profile, comprises combining: a pharmaceutical active agent, a non-polymeric, non-water soluble high viscosity liquid carrier material (HVLCM) having a viscosity of at least 5000 cP at 37° C. that does not crystallize neat at 25° C. and 1 atmosphere; a lactic acid-based polymer; and an organic solvent.

In one aspect, the composition comprises a pharmaceutical active agent that is risperidone or a pharmaceutically acceptable salt thereof; and means for reducing settling of the pharmaceutical active agent within the composition.

In another aspect, the composition comprises a pharmaceutical active agent, wherein when 2 mL of the composition is placed in an upright 2 mL vial for 10 months at 5° C., a difference between top concentration and bottom concentration divided by initial concentration is less than 35%, such as less than 15% or less than 10%. The top concentration is concentration of pharmaceutical active agent of the top 10% of the composition within the upright 2 mL vial after the 10 months storage. The bottom concentration is concentration of pharmaceutical active agent of the bottom 10% of the composition within the upright 2 mL vial after the 10 months storage. The initial concentration is concentration of pharmaceutical active agent of the composition before the 10 months storage.

In one aspect, the composition is a unit dosage form comprising from 0.01 mg to 500 mg, such as 1 mg to 250 mg or 10 mg to 100 mg of the pharmaceutical active agent. The composition may be contained within a vial, a syringe, a pre-filled syringe, an autoinjector, a needle-free injector.

The composition may be contained within a receptacle.

The compositions of the present disclosure may be made by any of the various methods and techniques known and available to those skilled in the art in view of the directions supplied in this specification.

For instance, polymer (DD, PLGA) may be dissolved in propylene carbonate. SAIB may be added to the mixture and allowed to dissolve and mix to make the vehicle (SAIB/PC/PLGA). Risperidone powder (e.g., produced by agitator bead milling and lyophilization) may then be added to the vehicle, and the suspension may be mixed using a homogenizer (or other suitable mixer).

In certain embodiments, first combine room temperature solvent(s), room temperature polymer and HVLCM heated to 80° C. Next, mix at 60-80° C. for a period of several hours to overnight (8-16 hours) until the composition is well-mixed. In other embodiments, dissolve the linear polymer in all of the solvent(s). Add hot HVLCM (heated at up to 80° C.). Then, mix at temperature of room temperature to 80° C. for 1 hour to overnight (8-16 hours) until the composition is well-mixed. In yet other embodiments, dissolve the linear polymer in some of the solvent(s). Mix the remainder of the solvent(s) with the HVLCM. Add hot HVLCM/solvent mixture (heated at up to 80° C.) to the linear polymer/solvent(s) mixture. Then, mix at temperatures that may range from room temperature to 80° C. for 1 hour to overnight (8-16 hours), until the composition is well-mixed.

The compositions are typically prepared at temperatures above room temperature. Once mixed, the compositions may be cooled back to room temperature and initially observed for cloudiness (indication of incipient phase separation), the presence of two liquid layers (usually of low to moderate viscosity) or the presence of a viscous layer underneath a less viscous layer. The compositions may then be left at room temperature for a significant period (usually one week or greater) and observed again for cloudiness, separation into two layers of moderate viscosity or the presence of a viscous layer.

A surprising result of the present disclosure is the ability to obtain small particles comprising pharmaceutical active agent, e.g., risperidone, via wet milling. In one aspect, a process comprises wet milling a pharmaceutical active agent in an aqueous solution at less than 20° C. to form a milled pharmaceutical active agent; maintaining the milled pharmaceutical active agent at less than 5° C.; and lyophilizing the milled pharmaceutical active agent to form a lyophilized pharmaceutical active agent having a median particle size, as measured by laser diffraction, of less than 10 micrometers, such as less than 5 micrometers, less than 3 micrometers, or less than 2 micrometers.

In another aspect, a suspension is produced by wet milling a pharmaceutical active agent in an aqueous solution at less than 20° C. to form a milled pharmaceutical active agent; maintaining the milled pharmaceutical active agent at less than 5° C.; and lyophilizing the milled pharmaceutical active agent to form a lyophilized pharmaceutical active agent having a median particle size, as measured by laser diffraction, of less than 10 micrometers, such as less than 5 micrometers, less than 3 micrometers, or less than 2 micrometers.

The composition may be gamma-irradiated to sterilize the composition. After storage for 150 days at 37° C., the weight average molecular weight of the lactic acid-based polymer of the gamma-irradiated composition is at least 90%, such as at least 95%, of the weight average molecular weight of the lactic acid-based polymer of an otherwise identical composition that is not gamma-irradiated before being stored for 150 days at 37° C. The weight average molecular weight of the lactic acid-based polymer of the composition after storage for 150 days at 37° C. is typically at least 50%, such as at least 60%, of the weight average molecular weight of the lactic acid-based polymer immediately before gamma radiation. Thus, in one aspect of the present disclosure a process of sterilizing a composition is provided, which process comprises gamma-irradiating a composition as defined elsewhere herein.

In some cases, the composition is stored at room temperature (e.g., 25° C.). In other cases, the composition is stored at 5° C. In still other cases, the composition is stored at −20° C.

Propylene carbonate improves the settling performance of compositions and allows longer shelf life and storage at refrigerated conditions of 2-8° C. when compared with compositions incorporating only NMP as the solvent. The results achieved with propylene carbonate are unexpected as the improvement is greater than would have been predicted from density considerations, as discussed in more detail below.

Propylene carbonate suspensions typically exhibit improved, acceptable settling performance, partially because PC has higher density than NMP. The higher density vehicle is closer to the density of risperidone; therefore the property helps to prevent the drug from settling. Another reason is that risperidone has higher solubility in NMP than in PC. Recrystallization and crystal growth may occur faster in NMP containing compositions which results in increasing particle size and settling rate with time.

Settling at low concentration of a spherical particle in a Newtonian fluid is described by the Stokes settling equation:

$$v = \frac{2r^2(\rho_1 - \rho_2)g}{9\eta}$$

where:
v=settling velocity
r=particle radius
$\rho_1$ and $\rho_2$=density of particle and fluid, respectively
g=acceleration due to gravity
$\eta$=viscosity of fluid For samples in a centrifuge, the acceleration due to gravity is replaced by the centripetal acceleration in the centrifuge:

$$v = \frac{2r^2(\rho_1 - \rho_2)\omega^2 R}{9\eta}$$

where:
$\omega$=angular velocity
R=centrifuge radius

The conditions for these equations are not strictly obeyed in the experiments described in this disclosure, but the equations can serve as a guide to expected behavior:
- Larger particles (larger r) are expected to settle more quickly.
- The larger the density difference between the particle and the fluid, the larger the expected settling velocity. Differences in settling velocity are expected to be proportional to overall differences in density.
- The lower the viscosity of the fluid, the more quickly the particles are expected to settle.

The magnitude of the improvement in settling performance of propylene carbonate compositions was unexpectedly greater than would have been expected from theory.

While not being bound by hypotheses, this unexpected result may reflect a slower rate of particle size growth during storage for the PC compositions. This does not appear to be due to the actual solubility of risperidone in the placebo vehicles, but might reflect the risperidone solubility in the respective solvents.

The disclosed compositions may be administered to subjects using conventional routes of administration, such as injection. Effective amounts of biologically active substances may be incorporated into the disclosed compositions so as to achieve a desired pharmacological effect.

In one aspect of the disclosure, a method of administering a pharmaceutical active agent such as, but not limited to, risperidone, paliperidone, or a combination thereof, comprises administering an effective amount of the composition. The composition typically comprises from 0.1 mg to 500 mg, such as 1 mg to 250 mg, 5 mg to 150 mg, or 25 mg to 150 mg, of the pharmaceutical active agent, such as risperidone or a pharmaceutically acceptable salt thereof. The composition may be administered on a regular basis, e.g., twice weekly or once a month. The composition is typically administered in an amount ranging from 0.05 mL to 10 mL, such as 0.1 mL to 8 mL, or 1 mL to 5 mL.

In one aspect, the pharmaceutical active agent and any metabolites thereof have a plasma level in the patient of at least 1 ng/mL, such as at least 5 ng/mL, or at least 8 ng/mL, at 28 days after administration. For instance, 9-OH risperidone is an active metabolite of risperidone.

In another aspect, the Cmax of the pharmaceutical active agent ranges from 5 ng/mL to 300 ng/mL, such as 5 to 100 ng/mL, 10 ng/mL to 70 ng/mL, or even 100 ng/mL to 200 ng/mL. The Cmax to Cmin ratio of the pharmaceutical active agent, as measured over 28 days, 21 days, or 14 days after administration, typically ranges from 2 to 40, such as from 5 to 30, or 10 to 20.

An amount of pharmaceutical active agent delivered into plasma at 24 hours of subcutaneous administration typically ranges from 0.5% to 50%, such as 0.5% to 20%, 0.5% to 15%, 1% to 10%, 2% to 5%, or even 20% to 50%, of a total amount of the pharmaceutical active agent administered. An amount of pharmaceutical active agent delivered into plasma at 4 weeks of subcutaneous administration ranges from 20% to 100%, such as 20% to 75%, or 30% to 60%, of a total amount of the pharmaceutical active agent administered. An amount of pharmaceutical active agent delivered into plasma at 24 hours of subcutaneous administration divided by an amount of pharmaceutical active agent delivered at 4 weeks of administration ranges from 0.05 to 0.2, such as 0.05 to 0.15, or 0.08 to 0.12.

In one aspect, the method comprises administering to a patient a composition comprising a pharmaceutical active agent and a carrier vehicle, wherein: AUC (0 to 5 hours) of pharmaceutically active moiety is less than 10%, such as less than 8%, of AUC (0 to 28 days), AUC (5 hours to 7 days) of pharmaceutically active moiety ranges from 10% to 80%, such as 20% to 70%, of AUC (0 to 28 days), and AUC (7 days to 28 days) of pharmaceutically active moiety ranges from 10% to 80%, such as 20% to 70%, of AUC (0 to 28 days). In some cases, the pharmaceutically active moiety consists of risperidone and 9-hydroxyrisperidone.

In another aspect, the method comprises administering to a patient a composition comprising a pharmaceutical active agent and a carrier vehicle, wherein: AUC (0 to 5 hours) of pharmaceutical active agent is less than 10%, such as less than 8%, of AUC (0 to 28 days), AUC (5 hours to 7 days) of pharmaceutical active agent ranges from 10% to 80%, such as 20% to 70%, of AUC (0 to 28 days), and AUC (7 days to 28 days) of pharmaceutical active agent ranges from 10% to 80%, such as 20% to 70%, of AUC (0 to 28 days).

In another aspect, the method comprises administering to a patient a composition comprising a pharmaceutical active agent and a carrier vehicle, wherein: the plasma concentration of pharmaceutically active moiety increases, after the plasma concentration of pharmaceutically active moiety increases, the plasma concentration of pharmaceutically active moiety remains steady for a steady phase such that the plasma concentration of pharmaceutically active moiety fluctuates less than ±30%, such less than ±25%, for a period of at least 4 days, such as at least 5 days, and after the plasma concentration of pharmaceutically active moiety remains steady, the plasma concentration of pharmaceutically active moiety increases, relative to an end of the steady phase, by an amount ranging from about 0% to about 40%, such as about 5% to about 35%, before decreasing. In some cases, the pharmaceutically active moiety consists of risperidone and 9-hydroxyrisperidone.

In a further aspect, the method comprises administering to a patient a composition comprising a pharmaceutical active agent and a carrier vehicle, wherein: the plasma concentration of pharmaceutical active agent increases, after the plasma concentration of pharmaceutical active agent increases, the plasma concentration of pharmaceutical active agent remains steady for a steady phase such that the plasma concentration of pharmaceutical active agent fluctuates less than ±30%, such less than ±25%, for a period of at least 4 days, such as at least 5 days, and after the plasma concentration of pharmaceutical active agent remains steady, the plasma concentration of pharmaceutical active agent increases, relative to an end of the steady phase, by an amount ranging from about 0% to about 40%, such as about 5% to about 35%, before decreasing.

In still a further aspect, the method comprises administering to a patient a composition comprising a pharmaceutical active agent and a carrier vehicle, wherein a PK profile is described by 3 absorption phases: (1) a first absorption phase occurs immediately after administration, with a first order rate constant ranging from $0.1 \text{ hr}^{-1}$ to $0.4 \text{ hr}^{-1}$, such as $0.2 \text{ hr}^{-1}$ to $0.3 \text{ hr}^{-1}$; (2) a second absorption phase occurs after a time delay ranging from 2.5 hours to 8.5 hours, such as 4.5 hours to 6.5 hours, after administration, with a first order rate constant ranging from $0.0005 \text{ hr}^{-1}$ to $0.005 \text{ hr}^{-1}$; and (3) a third absorption phase occurs after a time delay ranging from 5 days to 10 days, such as 6 days to 9 days, after administration, with a first order rate constant ranging from $0.0005 \text{ hr}^{-1}$ to $0.005 \text{ hr}^{-1}$, such as $0.001 \text{ hr}^{-1}$ to $0.003 \text{ hr}^{-1}$.

In one aspect, the method comprises administering to a patient a composition comprising a pharmaceutical active agent and a carrier vehicle,
wherein a maximum blood plasma concentration (Cmax) of pharmaceutically active moiety ranges from about 70% to about 140%, such as 80% to 125% or 90% to 115%, of 25 ng/mL, per 100 mg of pharmaceutical active agent administered, and an AUC (0 to 28 days) of pharmaceutically active moiety ranges from about 70% to about 140%, such as 80% to 125% or 90% to 115%, of 14,200 ng·hr/mL, per 100 mg of pharmaceutical active agent administered. In some cases, the pharmaceutically active moiety consists of risperidone and 9-hydroxyrisperidone.

In a further aspect, the method comprises administering to a patient a composition comprising a pharmaceutical active agent and a carrier vehicle,
wherein a maximum blood plasma concentration (Cmax) of pharmaceutical active agent ranges from about 70% to about 140%, such as 80% to 125% or 90% to 115%, of 11 ng/mL, per 100 mg of pharmaceutical active agent administered, and an AUC (0 to 28 days) of pharmaceutical active agent ranges from about 70% to about 140%, such as 80% to 125% or 90% to 115%, of 3670 ng·hr/mL, per 100 mg of pharmaceutical active agent administered.

In another aspect, the method comprises administering to a patient a composition comprising a pharmaceutical active agent and a carrier vehicle, wherein a pharmacokinetic profile of pharmaceutically active moiety is within ±20%, such as within ±15%, of the 100 mg dose profile of FIG. 30, per 100 mg of pharmaceutical active agent administered.

In yet another aspect, the method comprises administering to a patient a composition comprising a pharmaceutical active agent and a carrier vehicle, wherein a pharmaceutically active moiety pharmacokinetic profile comprises: a first peak during a first period ranging from 2 hours after the administration to 4 days after the administration, such as 4 hours to 3 days, a second peak during a second period ranging from 4 days after the administration to 14 days after the administration, such as 5 days to 12 days, and a trough between the first peak and the second peak, wherein the plasma concentration of pharmaceutically active moiety at the trough ranges from 40% to 90%, such as 50% to 80%, of the plasma concentration of pharmaceutically active moiety at the second peak. In some cases, the first peak ranges from about 15 ng/mL to about 25 ng/mL, such as about 17 ng/mL to about 23 ng/mL, per 100 mg of pharmaceutical active agent administered. In some cases, the second peak ranges from about 20 ng/mL to about 30 ng/mL, such as about 22 ng/mL to 28 ng/mL, per 100 mg of pharmaceutical active agent administered. In some cases, the pharmaceutically active moiety consists of risperidone and 9-hydroxyrisperidone.

In still another aspect, the method comprises administering to a patient a composition comprising a pharmaceutical active agent and a carrier vehicle, wherein a pharmaceutical active agent pharmacokinetic profile comprises: a first peak during a first period ranging from 2 hours after the administration to 4 days after the administration, such as 4 hours to 3 days, a second peak during a second period ranging from 4 days after the administration to 14 days after the administration, such as 5 days to 12 days, and a trough between the first peak and the second peak, wherein the plasma concentration of pharmaceutical active agent at the trough ranges from 30% to 90%, such as 50% to 80%, of the plasma concentration of pharmaceutical active agent at the second peak. In some cases, the first peak ranges from about 8 ng/mL to about 14 ng/mL, such as about 9 ng/mL to 13 ng/mL, per 100 mg of pharmaceutical active agent administered. In some cases, the second peak ranges from about 4 ng/mL to about 10 ng/mL, such as about 5 ng/mL to 9 ng/mL, per 100 mg of pharmaceutical active agent administered.

In some aspects, the method comprises administering to a patient a composition comprising a pharmaceutical active agent and a carrier vehicle, wherein a pharmaceutically active moiety pharmacokinetic profile comprises three phases: an increasing phase in which the plasma concentration of pharmaceutically active moiety increases from about 0 ng/mL before administration to at least 5 ng/mL, such as at least 10 ng/mL, per 100 mg of pharmaceutical active agent administered, at 24 hours after administration, a steady phase ranging from 24 hours after administration to about 6 days after administration in which the plasma concentration of pharmaceutically active moiety ranges from about 5 ng/mL to about 35 ng/mL, such as about 10 ng/mL to about 30 ng/mL, per 100 mg of pharmaceutical active agent administered, and a final phase starting at about 6 days after administration in which the plasma concentration of pharmaceutically active moiety increases before decreasing through at least about 28 days after administration. In some cases, the pharmaceutically active moiety consists of risperidone and 9-hydroxyrisperidone.

In another aspect, the method comprises administering to a patient a composition comprising a pharmaceutical active agent and a carrier vehicle, wherein a pharmaceutical active agent pharmacokinetic profile comprises three phases: an increasing phase in which the plasma concentration of pharmaceutical active agent increases from about 0 ng/mL before administration to at least 2 ng/mL, such as at least 5 ng/mL, per 100 mg of pharmaceutical active agent administered, at about 24 hours after administration, a steady phase ranging from about 24 hours after administration to about 6 days after administration in which the plasma concentration of pharmaceutical active agent ranges from about 2 ng/mL to 15 ng/mL, such as about 5 ng/mL to about 10 ng/mL, per 100 mg of pharmaceutical active agent administered, and a final phase starting at about 6 days after administration in which the plasma concentration of pharmaceutical active agent increases before decreasing through at least about 28 days after administration.

In some embodiments, a plasma concentration of pharmaceutically active moiety ranges from about 5 ng/mL to about 45 ng/mL, such as about 10 ng/mL to about 35 ng/mL or about 10 ng/mL to about 30 ng/mL, per 100 mg of pharmaceutical active agent administered, during 1 day following single administration to 28 days following single administration. In a further aspect, a plasma concentration of pharmaceutical active agent ranges from about 2 ng/mL to about 20 ng/mL, such as about 2 ng/mL to about 15 ng/mL, per 100 mg of pharmaceutical active agent administered, during 1 day following single administration to 28 days following single administration.

The administering may be subcutaneous, intramuscular, parenteral, via a catheter, etc. The administration may be accomplished via a needle and syringe (e.g., a pre-filled syringe), pump, patch-pump, bolus injector, infusion, via an auto-injector, etc. When a needle is used, the needle may have a length of less than or equal to 1 inch, such as less than or equal to 5/8 inch or less than or equal to 0.5 inch.

In some cases, the composition is self-administered. The composition may be administered by a health care professional or a non-health care professional.

The composition may be administered once a month, twice a month, once a week, once a day, etc. In some cases, the method does not comprise a separate loading dose administered at a different frequency.

In one aspect of the disclosure, a method of treating at least one of schizophrenia and bipolar disorder comprises administering an effective amount of a composition that contains a pharmaceutical active agent that is an anti-schizophrenia agent to a patient in need thereof. For instance, the anti-schizophrenia agent may comprise at least one of risperidone and paliperidone, or a pharmaceutically acceptable salt thereof.

In one embodiment, the composition is contained in a needle-free injector. In one embodiment, the needle-free injector is Zogenix's DosePro® Needle-free injector. FIG. 1 presents a longitudinal section through the DosePro® needle-free injector internal drug storage and delivery componentry. In FIG. 1, the injection force is provided by a compressed gas spring, which comprises a cylinder 1 enclosed at one end, and containing a gas, typically nitrogen, typically at a pressure between 150 and 300 bar. Contained within the cylinder is a ram 2. The end of the ram has a frusto-conical, truncated cone—portion 3 and a flange 4. There is a double o-ring seal 5 situated between the truncated cone section 3 and the flange 4. Prior to triggering the device, the ram 2 is held in the position illustrated in FIG. 1 by a latch 6 which sits in a groove in the dispensing member. The upper surface of the groove forms a cam surface 7. Consequently, there is force urging the latch to move to the left. In the configuration shown in FIG. 1, the latch is restricted from moving by the outer ring 8.

At the lower end of the cylinder 1, there is an outwardly directed flange 9. The cylinder is held in place by crimping the flange 9 to another outwardly directed flange 10 on the upper end on a coupling 11. The sleeve 8 consists of an upper sleeve portion 12 within which the cylinder is situated, and a lower sleeve portion 13. The lower sleeve portion 13 is connected to the coupling 11 by inter-engaging screw threads 14 formed on the inner and outer walls of the lower sleeve portion 13 and the coupling respectively 11.

The injector has a cartridge 15 which contains the medicament. In the cartridge there is a piston 16, slidingly and sealingly located therein. The piston 16 may comprise a cylindrical portion containing two larger diameter ribs, and a frusto-conical portion. The piston 16 is in contact with the medicament 17 and at the other end of the cartridge 15 there is a discharge orifice 18. Adjacent to the orifice 18 there is an interface seal 19 contained within a seal carrier 20. The interface seal 19 is required for filling the needle-free device as described in PCT/GB9700889. A stopper 20a seals the medicament into the capsule. Seal 19, seal carrier 20, and stopper 20a, comprise the cap that must be removed prior to delivery.

To place the device in the ready to deliver state, the cap must be snapped off at the frangible joint 21. This removes the seal 19 and exposes the orifice 18. The trigger blocking mechanism 22, which prevents the medication cartridge from moving back toward the upper sleeve portion 22, thereby preventing delivery, is removed. Finally, latch 6 must be moved from the first (safe) position, to the second (ready to deliver) position.

The latch 6 is incorporated into a groove in the dispensing member 2—not only does the groove have a cam surface 7 but also a locking surface 27 which is perpendicular to the dispensing member axis and is located radially inward of the cam surface 7. Additionally, to access the latch 6 there is an opening 28 in the upper sleeve 12, which prior to triggering is aligned with the latch 6.

Figure 2A:
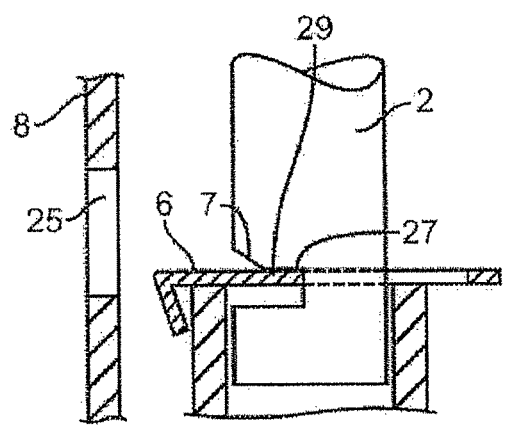
FIGS. 2*a, b* and *c* show the latch 6 and dispensing member 2 part of the needle-free injector from FIG. 1 in the three stages ending in triggering. In (a) the latch 6 is in the first, or safe position. In (b) the latch 6 is in the second position, the non-safety, ready to trigger position. In (c), the latch 6 is in the third position, following triggering.

FIGS. 2a, b and c illustrate the operation of the safety mechanism. When the latch and dispensing member are initially assembled, the latch occupies the first (safe) position, as shown in FIG. 2a. In this position, the dispensing member-engaging latch portion 29 is acted on by the locking surface 27. Frictional force ensures that the latch is held rigid by the locking surface—typically the dispensing member exerts a force of at least 100N.

Figure 2B:
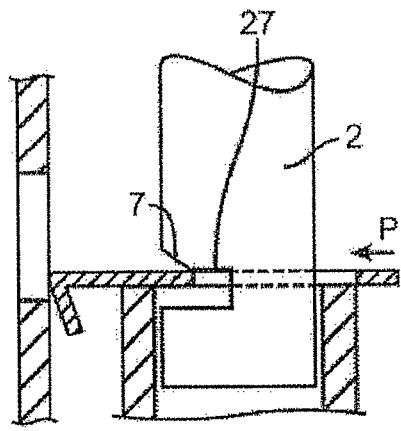

The latch is placed in the second (ready to deliver) position using a pin which fits through opening 28 to push the latch in the direction of the arrow P into the position shown in FIG. 2b, (and in FIG. 1). In this position the dispensing member engaging latch portion 29 is in contact with the radially inner end of the cam surface 7.

Figure 2C:
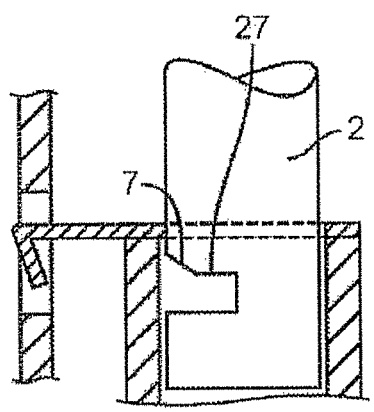

To cause delivery, the orifice 18 is then placed against the skin of the patient. Practically, this involves holding the device by the upper sleeve 12 portion. The upper sleeve 12 is then moved downwards with respect to the lower sleeve 13, bringing aperture 25 in the wall of the upper sleeve portion 8 into alignment with the latch 6. The latch then moves to the left into the aperture 25, under the force exerted on it by the cam surface 7 formed in the dispensing member 3 into the position shown in FIG. 2c. The injector then delivers.

Figure 3:
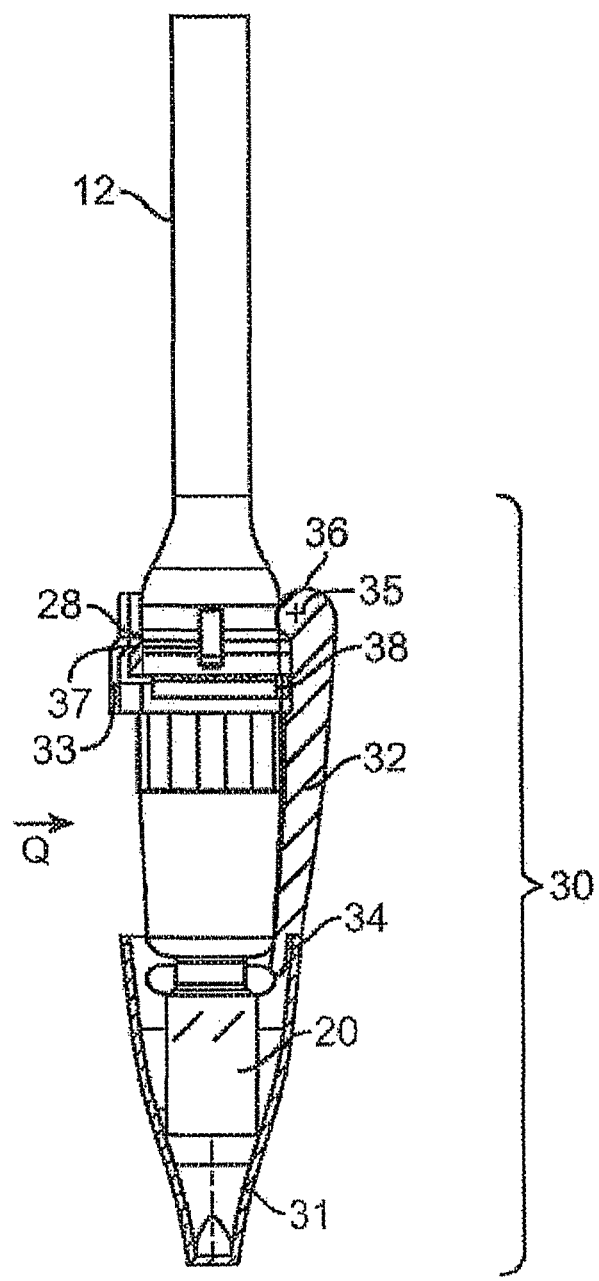
FIG. 3 illustrates a needle-free injector with one embodiment of the attachment for disengaging the safety mechanism.

It is advantageous to have a mechanism that places the device in the ready to deliver state in a simple motion or motions. FIG. 3 illustrates one embodiment of the combined needle-free injector plus means for disengaging the safety mechanism 30. In this Figure, the means for disengaging the safety mechanism consists of a cap 31 enclosing, and holding rigidly, the seal carrier 20, a lever 32 and a collar 33. The lever contains a lip 34 at the far end, over which the cap 31 is positioned. This ensures that the lever 32 cannot be moved before the outer cap 31 is removed, which in turn ensures that the user cannot move the latch or disengage the safety mechanism until the cap has been removed. The lever 32 is pivoted around the pivot axis 35, with the pivoted surface in contact with injector being a cam surface 36. The force required to pivot lever 32 is in the range from about 2N to about 30N. The collar 33 contains a pin 37 which extends into the device through the opening 28 in the upper sleeve 12 to impinge on the far side of the latch 6. The force required to move the latch is in the range from about 20N to about 120N. To stop the upper sleeve section 12 moving with respect to the lower sleeve section 13, there are block sections 38 between the upper and lower sleeves, which form part of the collar 33.

To deliver the device contents, the cap 31 is removed, exposing the injection orifice 18. With the outer cap 31 removed, the lip 34 is exposed, enabling the lever 32 to rotate about the pivot axis 35. Only when the outer cap 31 is removed can the lever 32 be rotated. As the lever 32 rotates, the cam surface 36 forces the collar 33 to move in the direction Q in FIG. 3, pushing the pin 37 against the latch 6. When the lever 32 has rotated through a complete cycle, approximately 180 degrees, the latch 6 moves to the second position, as shown in FIG. 2b. The blocks 38 no longer restrict the movement of the upper sleeve 12 with respect to the lower sleeve 13 and the device can trigger as described above. By integrating the cap 31 to the lever 32 with a flexible joint at the tip 34, the mechanism can also be configured to ensure that the user removes the stopper and sets the safety in a single action.

In one aspect, a needle-free injector comprises a composition comprising a pharmaceutical active agent. The needle-free injector may further comprise a drug capsule. The drug capsule may be transparent or partly transparent. The drug capsule may be closed at one end by a piston. The piston may comprise a polymer, such as a clear polymer and such as polytetrafluoroethylene. Alternatively, the drug capsule may comprise glass, such as borosilicate glass. The glass may have undergone ion exchange strengthening. In some cases, the transparent portion of the drug capsule does not change color when gamma-irradiated.

In some cases, the drug capsule is prefilled. The needle-free injector may be single use and disposable.

The drug capsule may comprise at least one injection orifice. The at least one injection orifice may be closed during storage by a sealing element. The sealing element may be held rigidly to the injection orifice by a seal carrier. In some cases, the seal carrier must be removed prior to use. The seal carrier may be connected to the drug capsule by at least one element selected from: a frangible connection, a screw connection, a bayonet connection, and a luer connection.

The needle-free injector may comprise a triggering mechanism. The triggering mechanism may be activated by pressing the at least one injection orifice against the target injection surface. The needle-free injector may further comprise a safety mechanism that ensures that the device cannot be actuated prematurely. The safety mechanism ensures that the device cannot be actuated until after removal of the seal carrier.

The needle-free injector may comprise a self-contained energy source. The energy source comprises at least one member selected from: a compressed mechanical spring, a compressed gas, a pyrotechnic charge, and a battery.

The needle-free injector may further comprise a ram which upon activation of the triggering mechanism, under the urging of the energy source traverses a gap and subsequently strikes the piston, creating a pressure spike in the composition. The urging of the energy source, the mass of the ram, the length of the gap, the mechanical properties of the piston, and the size of the orifice may be selected such that in use, more than 90% of injections inject more than 90% of the composition subcutaneously.

In one exemplary embodiment, the composition is delivered using a needle-free injector. Needle-free injectors are representative examples for the delivery of antipsychotic active pharmaceutical ingredients for a number of reasons. Psychotic patients may present for treatment in a highly agitated state, and the sight of a needle, or the puncture of the skin by a needle, may significantly increase this agitation. The psychotic state and agitation may increase the likelihood of the patient moving erratically during administration of the composition, increasing the risk of injury to the patient, and also increasing the risk of injury and exposure of the care giver to pathogens. Needle-free injectors remove the requirements of sharps disposal, further simplifying administration procedures and making them safer.

In one aspect, the present disclosure comprises a unit dosage form that may be prefilled, sterile, compatible with gamma sterilization, single use disposable, an auto-injector, may include a safety mechanism to prevent premature actuation, may include additional safety features to prevent or reduce the incidence to needle stick injury, including but not limited to needle shields, needle retraction and needle-free injection, may be portable and include a self contained power source, and may be disabled after use.

An exemplary embodiment of the needle-free injector is prefilled, and portable with a self contained energy source. This embodiment further simplifies the administration, and allows a skilled care giver to give more attention to the patient and spend less time preparing the injection. This embodiment, and the removal of the requirement for sharps disposal, may also enable administration in a home or residential or long term care facility setting by a skilled care giver, family member, or the self administration by the patient. For example, the preparation of and delivery from a needle-free injector would require less than 10 steps, such as less than 5 steps, and further such as 3 steps or fewer. For example, one embodiment requires only three steps: The removal of an orifice cap, actuation of a safety mechanism actuator to place the device in the ready to deliver state, and pressing the orifice against the desired injection site to trigger. It may also be possible to combine the actions of removal of an orifice cap and actuation of the safety mechanism, further simplifying delivery.

Needle-free injectors can be used, for example, for the delivery of elevated viscosity compositions, including those of the current disclosure. Delivery of high viscosity compositions by needle and syringe can be difficult due to high required hand strength and long delivery times. These problems often lead to the requirement for delivery via infusion or bolus injectors. The long delivery times via needle and syringe or infusion can be especially problematic for the treatment of psychotic patients, who may present in an agitated state. Needle-free injection can significantly reduce delivery time, as the ratio of delivery orifice length to lumen diameter, which is very small compared to needle systems such as syringes or infusion systems, generally reduces or avoids the development of viscous flow during delivery, allowing the delivery of viscous compositions in short times. This feature in combination with a self contained energy source removes the requirement of high hand strength. The advantages of needle-free injection for high viscosity compositions are described in U.S. Pat. No. 8,066,661.

The combination of a sufficiently powerful source of energy and low viscous losses in a needle-free injector leads to very short delivery times, in general less than 0.5 seconds, such as less than 0.2 seconds, and further such as about 0.1 seconds or less. These short delivery times are less than human reaction times, and significantly reduce the possibility of the patient moving during administration, further improving safety to the patient and caregiver.

Compliance with prescribed treatment is an issue with all treatment regimens, and can be particularly problematic in the treatment of psychotic patients. Combinations of features of a delivery system, and particularly needle-free injectors such as prefilled, single use, disposable, requiring a minimized number of steps for preparation and delivery, portability, a self contained power source, no requirement for sharps disposal, removal of risk of needle stick injury, short delivery times, low hand strength requirements, ability for administration in a home or care facility, ability for self administration, avoidance of premature actuation, and removal of fear and agitation caused by needles. Those features, alone or in combination, can work to increase compliance.

Needle-free injectors are available using many different types of energy, and the energy may be supplied by the user, for example where a spring is manually compressed and latched to temporarily store the energy until it is required to "fire" the injector. Alternatively, the injector may be supplied having the energy already stored—for instance by means of a precompressed spring (mechanical or gas), or pyrotechnic charge.

Some injectors are intended for disposal after a single use, whereas others have a re-loadable energy storage means and a disposable medicament cartridge, and there are many combinations to suit particular applications and markets. For the purposes of the present disclosure, the term "actuator" will be used to describe the energy storage and release mechanism, whether or not it is combined with the medicament cartridge. In all cases, it is necessary to arrange for sufficient force at the end of the piston stroke to deliver the entire medicament at the required pressure.

EP 0 063 341 and EP 0 063 342 disclose a needle-free injector which includes a piston pump for expelling the liquid to be injected, which is driven by a motor by means of a pressure agent. The liquid container is mounted laterally to the piston pump. The amount of liquid required for an injection is sucked into the pump chamber by way of an inlet passage and a flap check valve when the piston is retracted. As soon as the piston is moved in the direction of the nozzle body the liquid is urged through the outlet passage to the nozzle and expelled. The piston of the piston pump is a solid round piston.

EP 0 133 471 describes a needle-free vaccination unit which is operated with carbon dioxide under pressure, from a siphon cartridge by way of a special valve.

EP 0 347 190 discloses a vacuum compressed gas injector in which the depth of penetration of the injected drug can be adjusted by means of the gas pressure and the volume of the drug can be adjusted by way of the piston stroke.

EP 0 427 457 discloses a needle-free hypodermic syringe which is operated by means of compressed gas by way of a two-stage valve. The injection agent is disposed in an ampoule which is fitted into a protective casing secured to the injector housing. The ampoule is fitted on to the end of the piston rod. Disposed at the other end of the ampoule is the nozzle whose diameter decreases towards the end of the ampoule.

WO 89/08469 discloses a needle-free injector for one-off use. WO 92/08508 sets forth a needle-free injector which is designed for three injections. The ampoule containing the drug is screwed into one end of the drive unit, with the piston rod being fitted into the open end of the ampoule. At its one end, the ampoule contains the nozzle through which the drug is expelled. A displaceable closure plug is provided approximately at the center of the length of the ampoule. The dose to be injected can be adjusted by changing the depth of the ampoule. The piston rod which projects from the drive unit after actuation of the injector is pushed back by hand. Both units are operated with compressed gas.

WO 93/03779 discloses a needle-free injector with a two-part housing and a liquid container which is fitted laterally to the unit. The drive spring for the piston is stressed by means of a drive motor. The spring is released as soon as the two parts of the housing are displaced relative to each other by pressing the nozzle against the injection location. Respective valves are provided in the intake passage for the liquid and in the outlet of the metering chamber.

WO 95/03844 discloses a further needle-free injector. It includes a liquid-filled cartridge which at one end includes a nozzle through which the liquid is expelled. At the other end the cartridge is closed by a cap-type piston which can be pushed into the cartridge. A piston which is loaded by a pre-stressed spring, after release of the spring, displaces the cap-type piston into the cartridge by a predetermined distance, with the amount of liquid to be injected being expelled in that case. The spring is triggered as soon as the nozzle is pressed sufficiently firmly against the injection location. This injector is intended for one-off or repeated use. The cartridge is arranged in front of the spring-loaded piston and is a fixed component of the injector. The position of the piston of the injector which is intended for a plurality of uses is displaced after each use by a distance in a direction towards the nozzle. The piston and the drive spring cannot be reset. The pre stressing of the spring is initially sufficiently great to expel the entire amount of liquid in the cartridge all at once. The spring can only be stressed again if the injector is dismantled and the drive portion of the injector assembled with a fresh, completely filled cartridge.

U.S. Pat. No. 5,891,086 describes a needle-free injector, combining an actuator and a medicament cartridge. The cartridge is pre-filled with a liquid to be injected in a subject, and having a liquid outlet and a free piston in contact with the liquid, the actuator comprising an impact member urged by a spring and temporarily restrained by a latch means, the impact member being movable in a first direction under the force of the spring to first strike the free piston and then to continue to move the piston in the first direction to expel a dose of liquid through the liquid outlet, the spring providing a built-in energy store and being adapted to move from a higher energy state to a lower energy state, but not vice versa. The actuator may comprise trigger means to operate the said latch, and thus initiate the injection, only when a predetermined contact force is achieved between the liquid outlet of the said cartridge and the subject. Further examples and improvements to this needle-free injector are found in U.S. Pat. No. 6,620,135, U.S. Pat. No. 6,554,818, U.S. Pat. No. 6,415,631, U.S. Pat. No. 6,409,032, U.S. Pat. No. 6,280,410, U.S. Pat. No. 6,258,059, U.S. Pat. No. 6,251,091, U.S. Pat. No. 6,216,493, U.S. Pat. No. 6,179,583, U.S. Pat. No. 6,174,304, U.S. Pat. No. 6,149,625, U.S. Pat. No. 6,135,979, U.S. Pat. No. 5,957,886, U.S. Pat. No. 5,891,086, and U.S. Pat. No. 5,480,381.

U.S. Pat. No. 3,859,996, Mizzy, discloses a controlled leak method to ensure that the injector orifice is placed correctly at the required pressure on the subject's skin at the correct normal to the skin attitude. When placement conditions are met, controlled leak is sealed off by contact pressure on the subject's skin, the pressure within the injector control circuit rises until a pressure sensitive pilot valve opens to admit high pressure gas to drive the piston and inject the medicament.

WO Patent 82/02835, Cohen and Ep-A-347190, Finger, discloses a method to improve the seal between the orifice and the skin and prevent relative movement between each. This method is to employ a vacuum device to suck the epidermis directly and firmly onto the discharge orifice. The discharge orifice is positioned normal to the skin surface in order to suck the epidermis into the orifice. This method for injection of the medicament into the skin and the injector mechanism are different and do not apply to the present disclosure because of its unique ampule design.

U.S. Pat. No. 3,859,996, Mizzy, discloses a pressure sensitive sleeve on the injector which is placed on the subject, whereby operation of the injector is prevented from operating until the correct contact pressure between orifice and the skin is achieved. The basic aim is to stretch the epidermis over the discharge orifice and apply the pressurized medicament at a rate which is higher than the epidermis will deform away from the orifice.

U.S. Pat. No. 5,480,381, T. Weston, discloses a means of pressuring the medicament at a sufficiently high rate to pierce the epidermis before it has time to deform away from the orifice. In addition, the device directly senses that the pressure of the discharge orifice on the subject's epidermis is at a predetermined value to permit operation of the injector. The device is based on a cam and cam follower mechanism for mechanical sequencing, and contains a chamber provided with a liquid outlet for expelling the liquid, and an impact member, to dispell the liquid.

U.S. Pat. No. 5,891,086, T. Weston, describes a needle-free injector embodiment that contains a chamber that is pre-filled with a pressurized gas which exerts a constant force on an impact member in order to strike components of a cartridge and expulse a dose of medicament. This device contains an adjustment knob which sets the dose and the impact gap, and uses direct contact pressure sensing to initiate the injection. In an exemplary embodiment of the disclosure for the delivery of sustained release risperidone and other active pharmaceutical ingredients, the composition may be delivered using a needle-free injector which is single use, disposable, portable, and has a self contained energy source comprising compressed nitrogen gas. The composition is factory prefilled in a borosilicate glass capsule which is strengthened by ion exchange. The glass capsule is sealed at the proximal end by a piston which is comprised of polytetrafluoroethylene which has been modified to improve its sealing properties. The glass capsule comprises an injection orifice at the distal end which is sealed after filling and during storage by a seal which is held in a seal carrier. The glass capsule is contained in a clear plastic sleeve which is frangibly attached to the seal carrier. The injector comprises a ram which comprises a pair of o-rings that seal the compress gas chamber of the energy source. Before actuation the ram is held in place against the urging of the compressed gas by a latch. The latch has a safe position, a ready position and a triggered position. The latch is disposed in a slot in the ram which has a latch safe section which is perpendicular to the ram axis, and a latch ready section at a slope to the ram axis and functions as a cam. The ram is separated from the piston by a gap, across which upon triggering the ram flies under the urging of the compressed gas, striking the piston. The injector comprised a safety lever, which when rotated moves the latch from the safe to the ready position and removes an additional blocking element. The level and the seal carrier are configured to ensure that the seal carrier must be removed prior to actuating the latch. The injector is partially contained in a housing. The housing comprises an aperture into which the latch moves under the urging of the cam surface when the device is actuated. The housing, after removal of the blocking element, is slidable relative to the internal components. Disposed between the housing and the internal components is a damping grease which prevents recoil of the internal components when the injector is actuated. To deliver the contents of the injector, first the seal carrier and seal is removed. Then the lever is actuated. The orifice is pressed against the desired injector site. This pressing causes the housing to slide relative to the internal components, exposing the latch to the aperture. The latch moves into the aperture under the urging of the cam, freeing the ram and triggering the device. Upon striking the piston, the ram creates a pressure spike in the composition. This portion of the delivery is the puncture phase, whereby composition leaving the capsule through the orifice creates a hole in the skin down to the subcutaneous layer. The ram then causes piston, under the urging of the compressed gas, to move through the capsule, expelling the remainder of the composition in a reduced pressure delivery phase. This embodiment, improvements to this embodiment, methods of manufacture, and methods of treatment are described in U.S. Pat. Nos. 5,891,086; 5,957,886; 6,135,979; 7,776.007; 7,901,385; 8,267,903; 8,118,771; 8,241,243; 8,241,244; 8,287,489; 8,343,130; 7,150,297; 6,251,091; 6,174,304; 6,681,810; 6,280,410; 6,554,818; 6,620,135; 5,480,381; 7,231,945; 7,320,346; and 8,066,661; and PCT applications PCT/US2012/020654; PCT/US2011/051617, PCT/US2009/002533; and PCT/US2007/001403.

The current disclosure describes various viscous compositions that can be delivered using a needle-free injector including the injector of U.S. Pat. No. 5,891,086 to provide for subcutaneous (SC), intradermal (ID), intramuscular (IM) and other types of delivery.

In some cases, the compositions are phase stable and/or require relatively low amounts of solvent. While not wishing to be bound by theory, this result may achieved by one or more of relatively low molecular weight polymer, relatively high L:G ratio, and polymers having alkoxy end groups. Compositions with reduced solvent are typically beneficial as they are generally more biocompatible.

Studies conducted with the clinical composition described in Example 15 comprising risperidone, along with other compositions of similar chemical composition, indicate that the PK profile of SC risperidone-vehicle composition is consistently characterized by a sustained release of risperidone with low initial burst/no dose dump, a gradual decline in risperidone levels over time, and dose proportionality. Initial burst is a common phenomenon to most types of depot compositions and needs to be low enough such that the maximum observed concentration (Cmax) and the maximum exposure levels (i.e., area under the concentration-time curve [AUC] from time zero to 24 hours [AUC0-24 hr] and maximum observed concentration [Cmax]), do not exceed thresholds which result in adverse events.

The compositions may be administered SC as a once monthly administration and may lead to improved patient compliance over short-acting oral tablets or biweekly IM administration. Risperidone compositions may not require oral dose supplementation because drug release begins immediately upon injection, leading to a less complicated initiation of product dosing and improved patient compliance.

The present disclosure will be further illustrated by way of the following Examples. These examples are non-limiting and do not restrict the scope of the disclosure. Unless stated otherwise, all percentages, parts, etc. presented in the examples are by weight.

EXAMPLES

Example 1: Polymer Synthesis

This Example involves a representative polymer synthesis.

DL-lactide (147.22 grams), glycolide (39.52 grams), and 1-dodecanol (13.25 grams) were added to a 500-mL, 3-neck round bottom flask. The flask was sealed with a glass stopper, a gas joint with a stopcock, and a stirrer bearing with a glass shaft and Teflon® paddle. The ambient atmosphere was removed from the flask under vacuum and the flask was back-filled with nitrogen gas. The flask was placed in an oil batch at 155° C. and stirred under a positive pressure of nitrogen gas. When the monomer and initiator had melted, stannous 2-ethylhexanoate was added as a solution in dry toluene. The amount of catalyst added was approximately 0.016 wt %. The polymerization was allowed to proceed for 3 hours. Next, the solid polymer was subjected to vacuum to remove residual monomer for one hour. Then the contents of the flask were discharged from the flask onto a sheet of Teflon® film and allowed to cool. Once cooled, the product was crushed to granular powder in a stainless steel beaker and with a stainless steel pestle. The resulting polymer had a weight average molecular weight (Mw) (measured by GPC in tetrahydrofuran) of 7.7 kDa.

Example 2: Vehicle Formulations

This Example involves a representative method of making a formulation comprising sucrose acetate isobutyrate, polymer, and solvent.

Poly(lactic acid)(glycolic acid) (PLGA) was removed from cold storage and allowed to warm to room temperature. The polymer was weighed in a glass jar. Next, N-methyl-pyrrolidone (NMP) was dispensed into the glass jar. To dissolve the PLGA in the NMP, the mixture was placed in a rotator and rotated at 20 rpm at room temperature for about 12 hours.

Sucrose acetate isobutyrate (SAIB) was heated to 80° C. for approximately an hour. The heated SAIB was poured into the glass jar containing the PLGA and NMP. The mixture was rotated in an oven at 50° C. at 20 rpm for about 2 hours. The jar was removed from the oven and allowed to cool to room temperature.

Example 3: Effect of Polymer End Group

Phase compatibility studies were performed to generate a thermodynamic understanding of the formulation variables and to inform formulation design. One of the studies involved evaluation of the role of polymer end groups and their impact on phase stability.

Several formulations were made to evaluate the phase stability of formulations including various proportions of sucrose acetate isobutyrate, N-methyl-pyrrolidone, and poly (lactic acid)(glycolic acid). The poly(lactic acid)(glycolic acid) was either initiated with dodecanol to yield a polymer with a dodeoxy end group or initiated with 1-hexanediol to yield a polymer with alcohol end groups.

Figure 4:
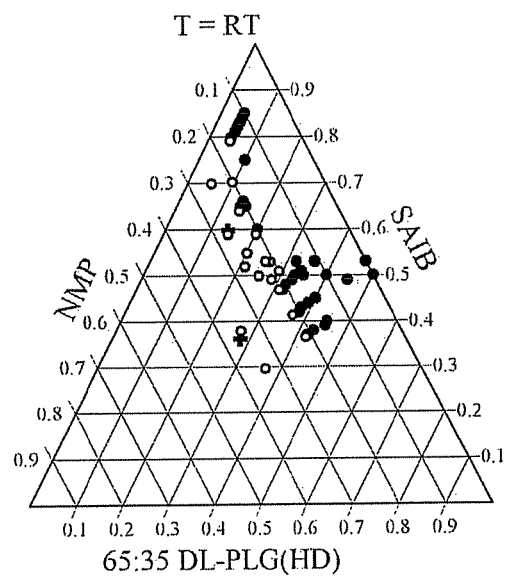
FIG. 4 is a phase diagram of compositions including 65:35 DL-PLGA initiated with 1-hexanediol, which polymer has a weight average molecular weight of 4.3 to 5.1 kDa.
Figure 5:
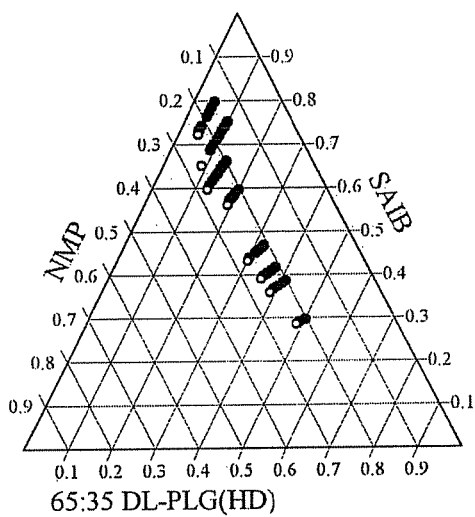
FIG. 5 is a phase diagram of compositions including 65:35 DL-PLGA initiated with 1-hexanediol, which polymer has a weight average molecular weight of 7.0 kDa.
Figure 6:
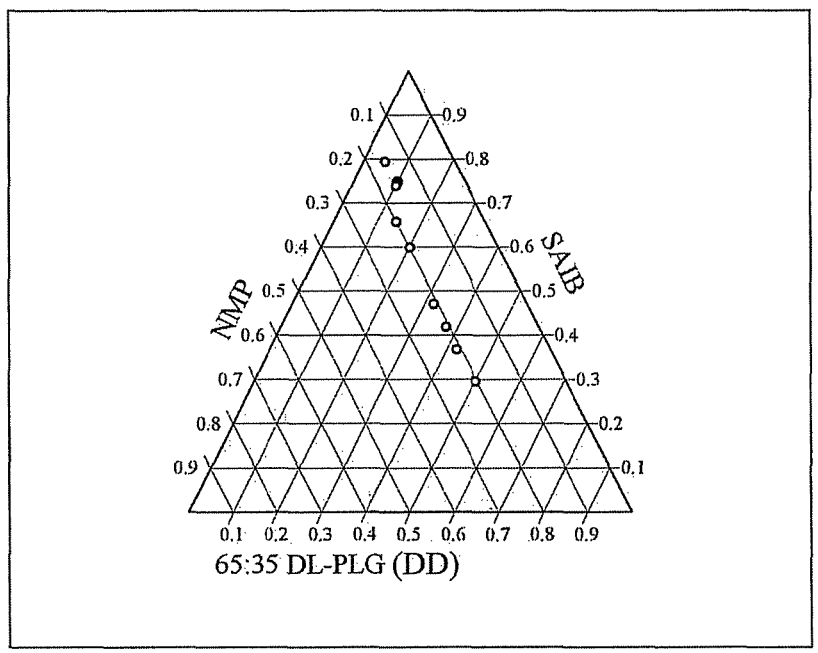
FIG. 6 is a phase diagram of compositions including 65:35 DL-PLGA initiated with dodecanol, which polymer has a weight average molecular weight of 6.6 kDa.

The solubilization of these formulations was observed visually. The results are summarized in the ternary phase diagrams depicted in FIGS. 4 to 6. FIGS. 4 and 5 are phase diagrams for formulations including the polymer initiated with 1-hexanediol. Specifically, open circles indicate formulations that were monophasic, whereas solid circles indicate formulations that phase separated. Information on the meaning of the crosses in FIG. 4 was not readily available. FIG. 6 is a phase diagram for formulations including the polymer initiated with dodecanol.

Comparing FIGS. 4 to 6 shows that the formulations including the polymer initiated dodecanol provided a larger region of solubility than formulations including the polymer initiated with 1-hexanediol. Thus, the polymer with a dodeoxy end group provided a broader region of thermodynamically stable, mono-phase compositions.

Example 4: Vehicle Formulations

Further vehicle examples were prepared. Information relating to these examples is set forth in Table 1. Vehicle Nos. 1-7 are taken from U.S. Published Application No. 2008/0287464. For purposes of clarity, not all examples from the '464 application are included in the below Table 1.

Table 1 includes the following abbreviations:
SAIB: sucrose acetate isobutyrate
NMP: N-methyl-pyrrolidone
DMSO: dimethylsulfoxide
CremophorEL: Cremophor EL
Pluronic L44: Pluronic L44
BB: benzyl benzoate
PC: propylene carbonate
DMA: dimethylacetamide
Solutol: Solutol® HS 15 polyoxyethylene esters of 12-hydroxystearic acid
PLGA: poly(lactic acid)(glycolic acid)
PLA: poly(lactic acid)
PLA R202H: Resomer 202H poly(lactic acid)
TerCGL: poly(caprolactone)(glycolic acid)(lactic acid)
H2O: water
HD: 1-hexanediol
DD: dodecanol
LA: lactic acid
L:G: molar ratio of lactic acid to glycolic acid
L:G:C: molar ratio of lactic acid to glycolic acid to caprolactone
C8: octanol
C16: 1-hexadecanol

TABLE 1

| Vehicle No. | Vehicle | PLGA or PLA or TerCGL | | | |
| --- | --- | --- | --- | --- | --- |
| | | Initiator | L:G or L:G:C | Mw (kDa) | Solubility Behavior |
| 1 | SAIB/NMP/PLGA (65/20/15) | HD | 65:35 | 5.3 | Not soluble |
| 2 | SAIB/NMP/PLGA (60/20/20) | HD | 65:35 | 5.3 | Not soluble |

TABLE 1-continued

| Vehicle No. | Vehicle | Initiator | PLGA or PLA or TerCGL L:G or L:G:C | Mw (kDa) | Solubility Behavior |
|---|---|---|---|---|---|
| 3 | SAIB/NMP/DMSO/PLGA (53.8/15.4/10.8/20.1) | HD | 65:35 | 5.3 | Separates long term |
| 4 | SAIB/NMP/DMSO/PLGA (54.9/15.0/9.8/20.1) | HD | 65:35 | 5.3 | Separates long term |
| 5 | SAIB/NMP/DMSO/PLGA (55/20/5/20) | HD | 65:35 | 5.3 | Separates long term |
| 6 | SAIB/NMP/BB/PLGA (55/20/5/20) | HD | 65:35 | 5.3 | Not soluble |
| 7 | SAIB/NMP/PLGA (70/25/5) | H₂O | 50:50 | 5.3 | Separates at RT & 37° C. |
| 8 | SAIB/NMP/PLGA (55/25/20) | DD | 65:35 | 6.3 | Monophasic |
| 9 | SAIB/NMP/PLGA (45/25/30) | DD | 65:35 | 6.5 | Monophasic |
| 10 | SAIB/NMP/PLGA (60/20/20) | DD | 65:35 | 6.5 | Monophasic |
| 11 | SAIB/NMP/PLGA (55/20/25) | DD | 65:35 | 6.5 | Monophasic |
| 12 | SAIB/NMP/DMSO/PLGA (55/20/5/20) | DD | 65:35 | 6.5 | Monophasic |
| 13 | SAIB/NMP/DMSO/PLGA (55/15/10/20) | DD | 65:35 | 6.5 | Monophasic |
| 14 | SAIB/NMP/DMSO/PLGA (55/10/10/25) | DD | 65:35 | 6.5 | Monophasic |
| 15 | SAIB/NMP/DMSO/PLGA (55/15/5/25) | DD | 65:35 | 6.5 | Monophasic |
| 16 | SAIB/NMP/PLGA (63.4/16.5/20) | DD | 65:35 | 6.5 | Hazy |
| 17 | SAIB/NMP/PLGA (62/18/20) | DD | 65:35 | 6.5 | Monophasic |
| 18 | SAIB/NMP/PLGA (64.2/15.8/20.0) | DD | 65:35 | 6.5 | Turbid |
| 19 | SAIB/NMP/CremophorEL/PLGA (52.4/20.6/10.3/16.7) | DD | 65:35 | 6.5 | Monophasic |
| 20 | SAIB/Ethyl acetate/PLGA (54.7/24.7/21.1) | DD | 65:35 | 6.5 | Monophasic (Hazy at 5° C.) |
| 21 | SAIB/NMP/PLGA/Pluronic L44 (46.1/16.7/16.7/20.4) | DD | 65:35 | 6.5 | Monophasic |
| 22 | SAIB/NMP/PLGA (55/25/20) | DD | 75:25 | 6.5 | Monophasic |
| 23 | SAIB/NMP/DMSO/PLGA (55/15/7/23) | DD | 65:35 | 6.5 | Monophasic |
|  | SAIB/BB/PLGA (55/25/20) | DD | 65:35 | 6.5 | Turbid |
| 24 | SAIB/BB/TerCGL (55/25/20) | DD | 23:25:52 | 17 | Monophasic |
| 25 | SAIB/BB/TerCGL (55/25/20) | DD | 20:31:49 | 30.9 | Turbid |
| 26 | SAIB/NMP/TerCGL (55/25/20) | DD | 23:25:52 | 17 | Monophasic |
| 27 | SAIB/NMP/TerCGL (55/25/20) | DD | 20:31:49 | 30.9 | Monophasic |
| 28 | SAIB/PC/PLGA (55/25/20) | DD | 65:35 | 6.5 | Monophasic |
| 29 | SAIB/NMP/BB/PLGA (45/15/20/20) | DD | 65:35 | 6.5 | Monophasic |
| 30 | SAIB/PC/PLGA (50/30/20) | DD | 65:35 | 6.5 | Monophasic |
| 31 | SAIB/NMP/PLGA (50/30/20) | DD | 65:35 | 6.5 | Monophasic |
| 32 | SAIB/NMP/PLGA (65/15/20) | DD | 65:35 | 6.5 | Turbid |
| 33 | SAIB/NMP/PLA R202H (55/25/20) | LA | 100:0 | 14 | Monophasic |
| 34 | SAIB/NMP/PLGA (30/30/40) | DD | 65:35 | 6.3 | Monophasic |
| 35 | SAIB/NMP/PLGA (55/25/20) | DD | 75:25 | 6.5 | Monophasic |
| 36 | SAIB/NMP/PLGA/PLA R202H (55/25/17.5/2.5) | DD LA | 75:25 100:0 | 6.5 14 | Monophasic |
| 37 | SAIB/NMP/PLGA (55/25/20) | DD | 75:25 | 14.2 | Monophasic |
| 38 | SAIB/NMP/PLGA (55/25/20) | DD | 85:15 | 7.7 | Monophasic |

TABLE 1-continued

| Vehicle No. | Vehicle | Initiator | PLGA or PLA or TerCGL L:G or L:G:C | Mw (kDa) | Solubility Behavior |
|---|---|---|---|---|---|
| 39 | SAIB/NMP/PLGA (55/25/20) | DD | 85:15 | 13.9 | Monophasic |
| 40 | SAIB/NMP/PLGA/PLA R202H (55/25/15/5) | DD LA | 75:25 100:0 | 6.5 14 | Monophasic |
| 41 | SAIB/NMP/PLGA/PLA R202H (55/25/10/10) | DD LA | 75:25 100:0 | 6.5 14 | Monophasic |
| 42 | SAIB/PC/PLGA (44.1/36.3/19.6) | DD | 65:35 | 6.5 | Monophasic |
| 43 | SAIB/NMP/PLGA (55/25/20) | DD | 75:25 | 6.9 | Monophasic |
| 44 | SAIB/NMP/PLGA (55/25/20) | DD | 90:10 | 6.6 | Monophasic |
| 45 | SAIB/NMP/PLGA/PLA R202H (55/25/17.5/2.5) | DD LA | 85:15 100:0 | 7.7 14 | Monophasic |
| 46 | SAIB/NMP/PLGA/PLA R202H (55/25/15/5.0) | DD LA | 85:15 100:0 | 7.7 14 | Monophasic |
| 47 | SAIB/NMP/PLGA (60/25/15) | DD | 75:25 | 6.9 | Monophasic |
| 48 | SAIB/NMP/PLGA (52.5/27.5/20) | DD | 75:25 | 6.9 | Monophasic |
| 49 | SAIB/NMP/DMSO/PLGA (50/20/10/20) | DD | 75:25 | 5.9 | Monophasic |
| 50 | SAIB/NMP/DMSO/PLGA (50/25/5/20) | DD | 75:25 | 5.9 | Monophasic |
| 51 | SAIB/NMP/DMSO/PLGA (52/19/9/20) | DD | 75:25 | 5.9 | Monophasic |
| 52 | SAIB/NMP/DMSO/PLGA (48/21/11/20) | DD | 75:25 | 5.9 | Monophasic |
| 53 | SAIB/BB/PLA (8/72/20) | LA | 100:0 | 15 | Monophasic |
| 54 | SAIB/NMP/PLGA (55/25/20) | DD | 75:25 | 8.6 | Monophasic |
| 55 | SAIB/NMP/PLGA (50/30/20) | DD | 75:25 | 6.9 | Monophasic |
| 56 | SAIB/NMP/PLGA (52/28/20) | DD | 75:25 | 6.9 | Monophasic |
| 57 | SAIB/NMP/PLGA (55/26/20) | DD | 75:25 | 6.9 | Monophasic |
| 58 | SAIB/NMP/PLGA (48/32/20) | DD | 75:25 | 6.9 | Monophasic |
| 59 | SAIB/NMP/PLGA (49/31/20) | DD | 75:25 | 6.9 | Monophasic |
| 60 | SAIB/NMP/PLGA (49.5/30.5/20) | DD | 75:25 | 6.9 | Monophasic |
| 61 | SAIB/NMP/PLGA (51/29/20) | DD | 75:25 | 6.9 | Monophasic |
| 62 | SAIB/NMP/PLGA (50.5/29.5/20) | DD | 75:25 | 6.9 | Monophasic |
| 63 | SAIB/NMP/DMSO/PLGA (50/25/5/20) | DD | 75:25 | 6.9 | Monophasic |
| 64 | SAIB/NMP/DMSO/PLGA (52/19/9/20) | DD | 75:25 | 6.9 | Monophasic |
| 65 | SAIB/NMP/DMSO/PLGA (50/20/10/20) | DD | 75:25 | 6.9 | Monophasic |
| 66 | SAIB/NMP/DMSO/PLGA (48/21/11/20) | DD | 75:25 | 6.9 | Monophasic |
| 67 | SAIB/NMP/PLGA (55/25/20) | DD | 75:25 | 7.0 | Monophasic |
| 68 | SAIB/NMP/PLGA (50/30/20) | DD | 75:25 | 7.0 | Monophasic |
| 69 | SAIB/NMP/PLGA (46/34/20) | DD | 75:25 | 6.9 | Monophasic |
| 70 | SAIB/NMP/DMSO/PLGA (46/22.5/11.5/20) | DD | 75:25 | 6.9 | Monophasic |
| 71 | SAIB/NMP/PLGA (46/34/20) | DD | 75:25 | 7.0 | Monophasic |
| 72 | SAIB/NMP/DMSO/PLGA (46/22.5/11.5/20) | DD | 75:25 | 7.0 | Monophasic |
| 73 | SAIB/NMP/DMSO/PLGA (48/21/11/20) | DD | 75:25 | 7.0 | Monophasic |
| 74 | SAIB/NMP/PLGA (51.5/30/18.5) | DD | 75:25 | 7.0 | Monophasic |
| 75 | SAIB/NMP/PLGA (52/29/19) | DD | 75:25 | 7.0 | Monophasic |

TABLE 1-continued

| Vehicle No. | Vehicle | Initiator | PLGA or PLA or TerCGL L:G or L:G:C | Mw (kDa) | Solubility Behavior |
|---|---|---|---|---|---|
| 76 | SAIB/NMP/PLGA (53.5/27/19.5) | DD | 75:25 | 7.0 | Monophasic |
| 77 | SAIB/NMP/DMSO/PLGA (50/20/10/20) | DD | 75:25 | 7.0 | Monophasic |
| 78 | SAIB/PC/PLGA (44/36.5/19.5) | DD | 75:25 | 7.0 | Monophasic |
| 79 | SAIB/NMP/PLGA (45/35/20) | DD | 75:25 | 7.0 | Monophasic |
| 80 | SAIB/NMP/PLGA (44/36/20) | DD | 75:25 | 7.0 | Monophasic |
| 81 | SAIB/NMP/PLGA (40/40/20) | DD | 75:25 | 7.0 | Monophasic |
| 82 | SAIB/NMP/PLGA (31/49/20) | DD | 75:25 | 7.0 | Monophasic |
| 83 | SAIB/NMP/PLGA (58/27/15) | DD | 75:25 | 7.0 | Monophasic |
| 84 | SAIB/NMP/PLGA (55/28/17) | DD | 75:25 | 7.0 | Monophasic |
| 85 | SAIB/PC/PLGA (44/37/19) | DD | 75:25 | 7.0 | Monophasic |
| 86 | SAIB/NMP/DMSO/PLGA (52/15/14/19) | DD | 75:25 | 7.0 | Monophasic |
| 87 | SAIB/DMSO/PLGA (45/35/20) | DD | 75:25 | 7.0 | Monophasic |
| 88 | SAIB/NMP/DMSO/PLGA (50/15.5/14.5/20) | DD | 75:25 | 7.0 | Monophasic |
| 89 | SAIB/NMP/DMSO/PLGA (49.5/10/20.5/20) | DD | 75:25 | 7.0 | Monophasic |
| 90 | SAIB/DMSO/PLGA (48/32/20) | DD | 75:25 | 7.0 | Monophasic |
| 91 | SAIB/PC/PLGA (38/42/20) | DD | 75:25 | 7.0 | Monophasic |
| 92 | SAIB/PC/PLGA (34/46/20) | DD | 75:25 | 7.0 | Monophasic |
| 93 | SAIB/PC/PLGA (28/52/20) | DD | 75:25 | 7.0 | Monophasic |
| 94 | SAIB/DMA/PLGA (50/30/20) | DD | 75:25 | 7.0 | Monophasic |
| 95 | SAIB/NMP/PC/PLGA (46/10/24/20) | DD | 75:25 | 7.0 | Monophasic |
| 96 | SAIB/NMP/PC/PLGA (48/20/12/20) | DD | 75:25 | 7.0 | Monophasic |
| 97 | SAIB/DMA/PLGA (56/24/20) | DD | 75:25 | 7.0 | Monophasic |
| 98 | SAIB/DMA/PLGA (55/25/20) | DD | 75:25 | 7.0 | Monophasic |
| 99 | SAIB/DMA/PLGA (54/26/20) | DD | 75:25 | 7.0 | Monophasic |
| 100 | SAIB/NMP/Miglyol/PLGA (49.5/29.5/1/20) | DD | 75:25 | 7.0 | Monophasic |
| 101 | SAIB/NMP/Miglyol/PLGA (47/28/5/20) | DD | 75:25 | 7.0 | Monophasic |
| 102 | SAIB/NMP/Miglyol/PLGA (44/26/10/20) | DD | 75:25 | 7.0 | Monophasic |
| 103 | SAIB/NMP/Solutol/PLGA (50/27/3/20) | DD | 75:25 | 7.0 | Monophasic |
| 104 | SAIB/NMP/Solutol/PLGA (50/24/6/20) | DD | 75:25 | 7.0 | Monophasic |
| 105 | SAIB/NMP/Solutol/PLGA (48/29/3/20) | DD | 75:25 | 7.0 | Monophasic |
| 106 | SAIB/NMP/Solutol/PLGA (46/28/6/20) | DD | 75:25 | 7.0 | Monophasic |
| 107 | SAIB/NMP/PLGA (53/28/19) | DD | 75:25 | 7.0 | Monophasic |
| 108 | SAIB/NMP/PLGA (53.5/27.5/19) | DD | 75:25 | 7.0 | Monophasic |
| 109 | SAIB/NMP/PLGA (54.5/27.5/18) | DD | 75:25 | 7.0 | Monophasic |
| 110 | SAIB/NMP/PLGA (54/26/20) | DD | 65:35 | 6.5 | Monophasic |
| 111 | SAIB/PC/PLGA (37/43/20) | DD | 75:25 | 7.0 | Monophasic |
| 112 | SAIB/PC/PLGA (30/50/20) | DD | 75:25 | 7.0 | Monophasic |

TABLE 1-continued

| Vehicle No. | Vehicle | Initiator | PLGA or PLA or TerCGL L:G or L:G:C | Mw (kDa) | Solubility Behavior |
|---|---|---|---|---|---|
| 113 | SAIB/PC/DMSO/PLGA (48/16/16/20) | DD | 75:25 | 7.0 | Monophasic |
| 114 | SAIB/PC/DMSO/PLGA (44/18/18/20) | DD | 75:25 | 7.0 | Monophasic |
| 115 | SAIB/PC/DMSO/PLGA (46/17/17/20) | DD | 75:25 | 7.0 | Monophasic |
| 116 | SAIB/NMP/PLGA (48/32/20) | DD | 75:25 | 7.0 | Monophasic |
| 117 | SAIB/NMP/PLGA (46/34/20) | DD | 90:10 | 6.6 | Monophasic |
| 118 | SAIB/NMP/PLGA (55/25/20) | C8 | 65:35 | 5.4 | Monophasic |
| 119 | SAIB/NMP/PLGA (55/25/20) | C16 | 65:35 | 5.8 | Monophasic |
| 120 | SAIB/NMP/PLGA (48/32/20) | DD | 90:10 | 6.6 | Monophasic |
| 121 | SAIB/DMSO/PLGA (55/25/20) | C8 | 65:35 | 5.4 | Turbid |
| 122 | SAIB/NMP/PLGA (47/35/18) | C8 | 65:35 | 5.4 | Monophasic |
| 123 | SAIB/DMSO/PLGA (55/25/20) | C16 | 65:35 | 5.8 | Monophasic |
| 124 | SAIB/PC/PLGA (43/37/20) | C8 | 65:35 | 5.4 | Monophasic |
| 125 | SAIB/PC/PLGA (43/37/20) | C16 | 65:35 | 5.8 | Monophasic |
| 126 | SAIB/NMP/PLA (55/25/20) | DD | 100:0 | 13.9 | Monophasic |

Example 5: Olanzapine In Vitro Release from Formulations Comprising Various Polymers and Solvents As discussed in more detail below, this Example was directed to comparing the olanzapine in vitro release behavior of formulations comprising olanzapine, sucrose acetate isobutyrate, various solvents (propylene carbonate, benzyl benzoate, dimethylsulfoxide), and polymer (poly(lactic acid) or poly(lactic acid)(glycolic acid) initiated with dodecanol (DD)).

Vehicle preparation was similar to that described in representative Example 2 above. Olanzapine was added to the vehicle followed by homogenization.

Specifically, the in vitro release behavior of the following formulations was characterized.

| Formulation No. | Formulation | Initiator | PLGA or PLA L:G | Mw (kDa) |
|---|---|---|---|---|
| O1 | SAIB/PC/PLGA/OLZ (44/20/16/20) | DD | 65:35 | 6.5 |
| O2 | SAIB/BB/PLGA/OLZ (44/20/16/20) | DD | 65:35 | 6.5 |
| O3 | SAIB/DMSO/PLGA/OLZ (44/20/16/20) | DD | 65:35 | 6.5 |

Release rate from olanzapine was measured using two techniques. In a dialysis tubing technique, 0.5 mL samples were placed in dialysis tubing in 100 mL PBS w/2% SDS. The samples were moved to new media for each time point (n=4). In the other technique, 0.5 mL samples were placed in 1000 mL PBS w/2% SDS in a USP Apparatus 2 (n=2).

Figure 7:
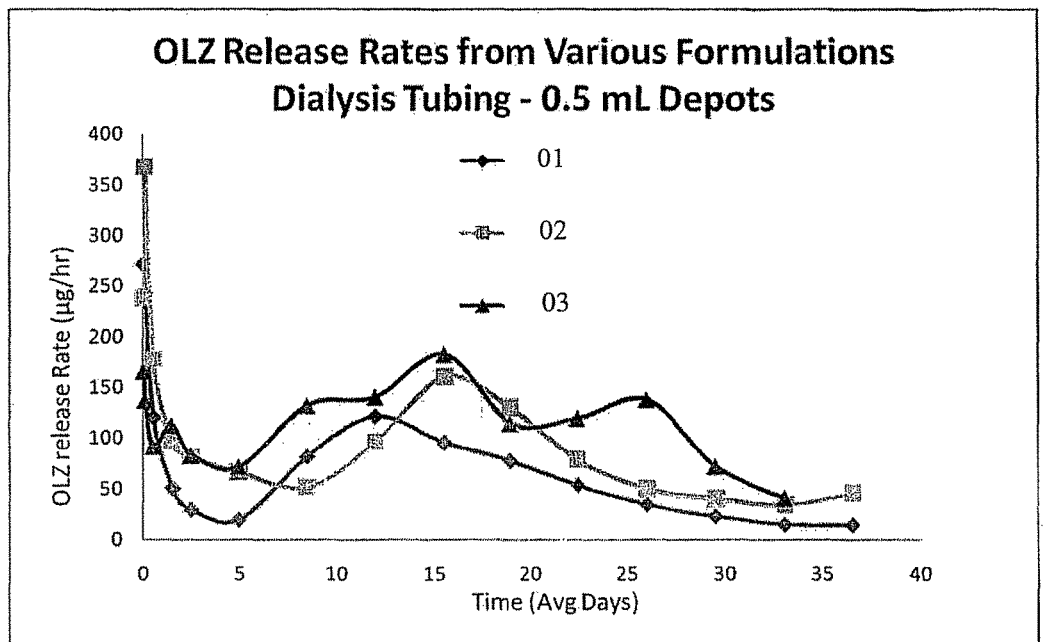
FIG. 7 shows in vitro release, as measured using dialysis tubing, of olanzapine from various vehicles.
Figure 8:
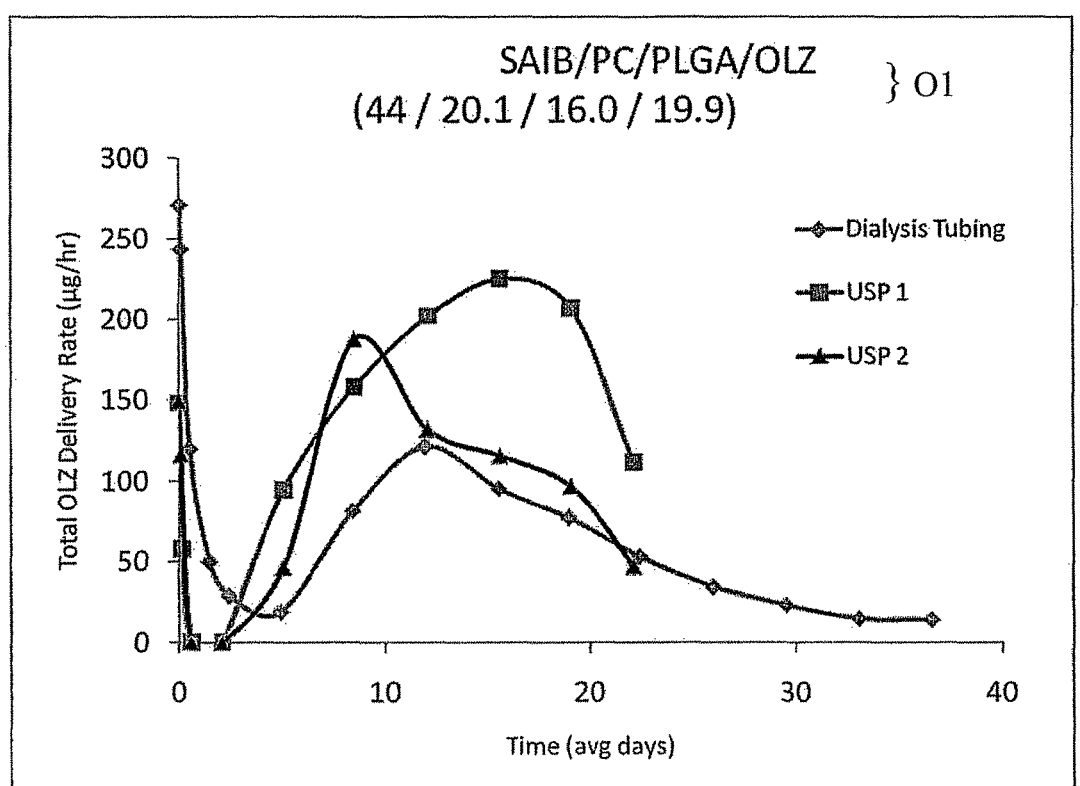
FIG. 8 shows in vitro release, as measured using dialysis tubing and a USP 2 apparatus, of olanzapine from a vehicle comprising sucrose acetate isobutyrate, propylene carbonate, and dodecanol-initiated poly(lactic acid)(glycolic acid).
Figure 9:
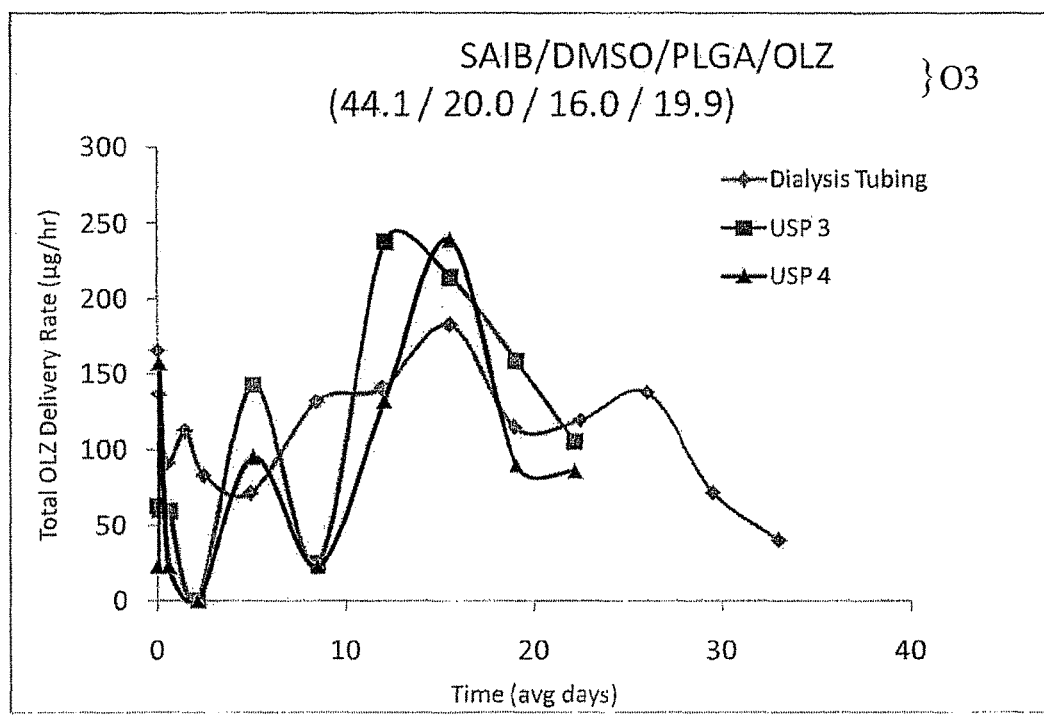
FIG. 9 shows in vitro release, as measured using dialysis tubing and a USP 2 apparatus, of olanzapine from a vehicle comprising sucrose acetate isobutyrate, dimethylsulfoxide, and dodecanol-initiated poly(lactic acid)(glycolic acid).

The release profiles from the formulations, as measured by the dialysis technique, are shown in FIG. 7. The release profiles, as measured by the dialysis and USP techniques, from formulations O1 and O3 are shown in FIGS. 8 and 9, respectively. These FIGS. show olanzapine release beyond 30 days.

Example 6: Exenatide In Vitro Release from Formulations Comprising Various Polymers and Solvents As discussed in more detail below, this Example was directed to comparing the exenatide in vitro release behavior of formulations comprising exenatide, sucrose acetate isobutyrate, various solvents (N-methyl-pyrrolidone, propylene carbonate, and dimethyl sulfoxide), and polymer (poly(lactic acid)(glycolic acid) with different initiators such as dodecanol (DD), 1-octanol (C8), and 1-hexadecanol (C16).

Vehicle preparation was similar to that described in representative Example 2 above. Exenatide was added to the vehicle followed by mixing.

Specifically, the in vitro release behavior of the following formulations was characterized.

| Formulation No. | Vehicle | Initiator | PLGA L:G | Mw (kDa) | Exenatide/ Formulation (mg/g) |
|---|---|---|---|---|---|
| E1 | SAIB/NMP/PLGA (50/30/20) | DD | 75:25 | 7.0 | 17.6 |
| E2 | SAIB/PC/PLGA (43/37/20) | C8 | 65:35 | 5.4 | 16.4 |
| E3 | SAIB/PC/PLGA (43/37/20) | C16 | 65:35 | 5.8 | 17.0 |
| E4 | SAIB/DMSO/PLGA (47/35/18) | C8 | 65:35 | 5.4 | 17.0 |
| E5 | SAIB/DMSO/PLGA (55/25/20) | C16 | 65:35 | 5.8 | 17.2 |

An aliquot (0.1 mL) of each composition was placed in a 2 mL conical vial with 1 mL of Dulbecco's Phosphate Buffered Saline (PBS) at 37° C., which vial was placed in an orbital shaker at 100 rpm (n=3). The release into the PBS was monitored for up to 6 days.

Figure 10:
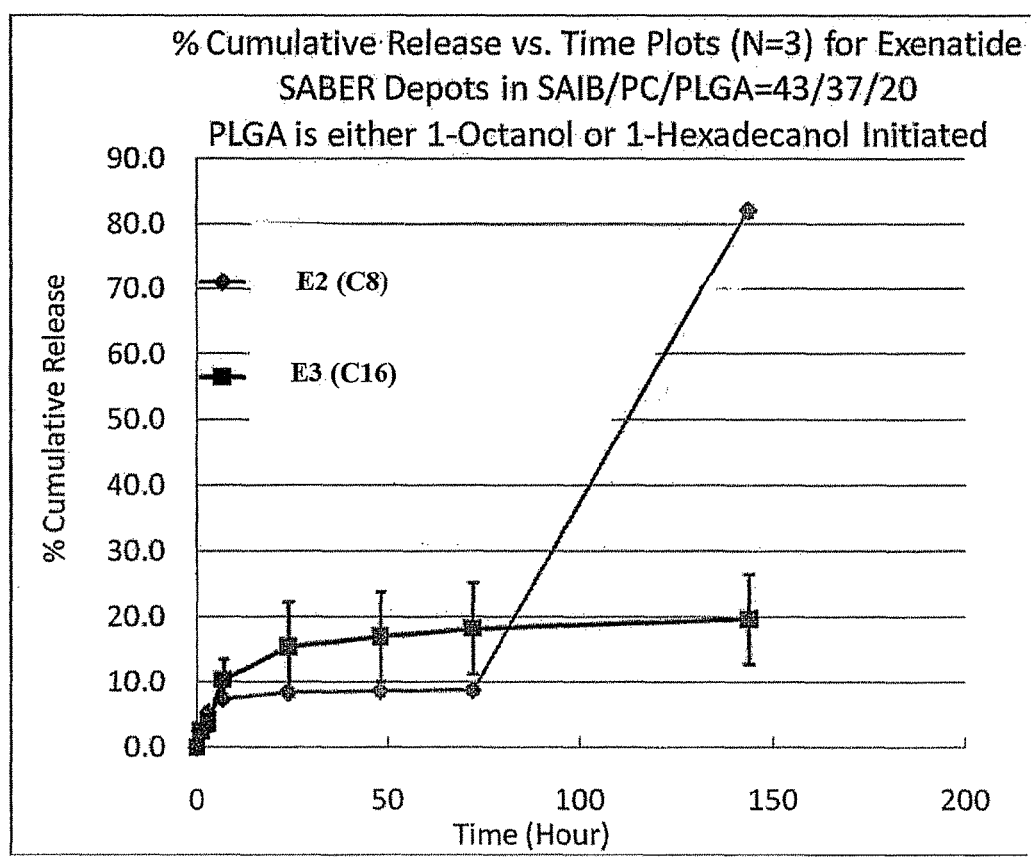
FIG. 10 shows in vitro release of exenatide from a vehicle comprising sucrose acetate isobutyrate, propylene carbonate, and poly(lactic acid)(glycolic acid) initiated with either octanol or 1-hexadecanol.
Figure 11:
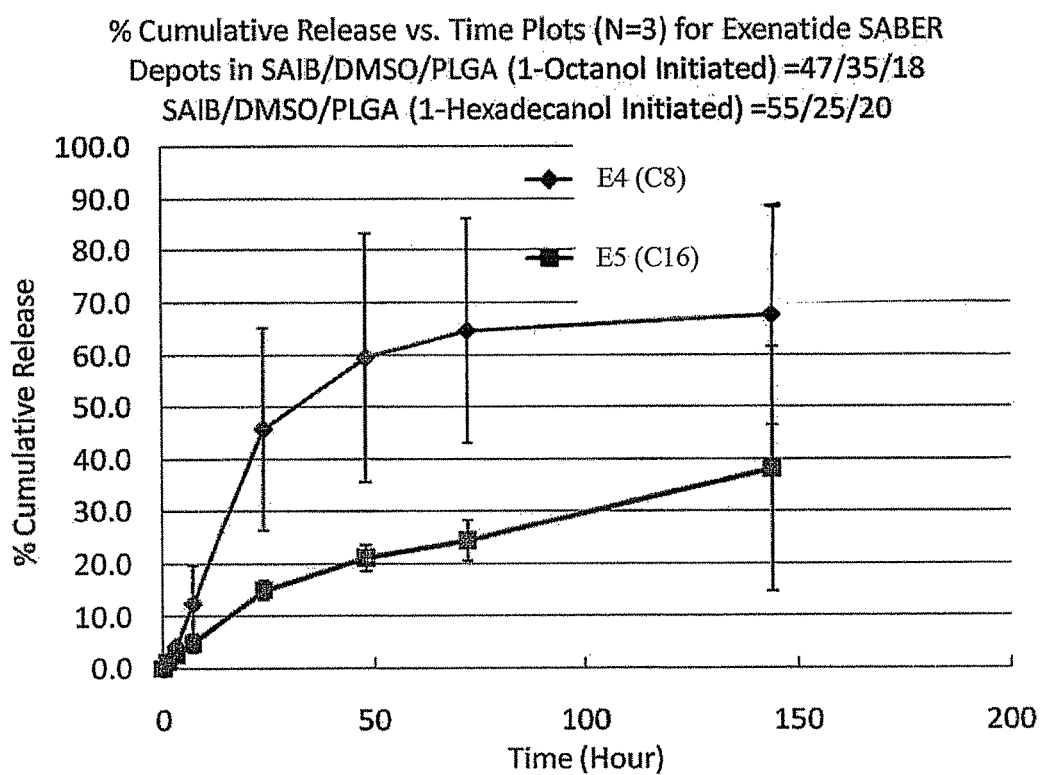
FIG. 11 shows in vitro release of exenatide from a vehicle comprising sucrose acetate isobutyrate, dimethylsulfoxide, and poly(lactic acid)(glycolic acid) initiated with either octanol or 1-hexadecanol.

The cumulative release profiles from the formulations comprising propylene carbonate and dimethylsulfoxide are shown in FIGS. 10 and 11, respectively. These FIGS. show exenatide release up to 150 hours. The cumulative release profile from the formulation comprising N-methyl-pyrrolidone is not shown because the exenatide degraded in the formulation.

The below Table lists the potency (% recovery) of exenatide depots at time 0.

Example 7: GLP-1 Analog In Vivo Release in Rats

As discussed in more detail below, this Example was directed to in vivo release in rats of two different GLP-1 analogs from formulations comprising the one of the GLP-1 analogs, sucrose acetate isobutyrate, solvent (e.g., benzyl alcohol, ethanol, dimethylsulfoxide, and/or N-methyl-pyrrolidone), and PLA R202H, i.e., a lactic acid-initiated poly (lactic acid) (PLA) having a Mw of 14 kDa.

The PK of each of the formulations shown in the below Table was evaluated in male Sprague-Dawley rats (N=3/group) following SC administration. The GLP-1 analogs in each of the formulations of Groups 1-6 were in suspension at the concentration shown below.

| Formulation No. | Vehicle composition | Formulation weight (mg) | Exenatide weight (mg) by theoretical calculation | Exenatide wt (mg) by HPLC | % Recovery (Exenatide wt by HPLC/Exenatide wt by theoretical wt calculation) * 100 |
|---|---|---|---|---|---|
| E1A | SAIB/NMP/PLGA | 110.4 | 1.943 | 2.158 | 111.1 |
| E1B | (Dodecanol initiated) = 50/30/20 | 114.0 | 2.006 | 2.204 | 109.9 |
| E2A | SAIB/PC/PLGA (1- | 123.4 | 2.024 | 2.322 | 114.7 |
| E2B | Octanol initiated) = 43/37/20 | 121.1 | 1.986 | 2.210 | 111.3 |
| E3A | SAIB/PC/PLGA (1- | 116.4 | 1.979 | 2.255 | 114.0 |
| E3B | Hexadecanol initiated) = 43/37/20 | 122.8 | 2.088 | 2.370 | 113.5 |
| E4A | SAIB/DMSO/PLGA | 117.4 | 1.996 | 1.968 | 98.6 |
| E4B | (1-Octanol initiated) = 47/35/18 | 114.4 | 1.945 | 2.047 | 105.2 |
| E5A | SAIB/DMSO/PLGA | 114.1 | 1.963 | 1.263 | 64.3 |
| E5B | (1-Hexadecanol | 119.1 | 2.049 | 2.049 | 72.3 |
| E5C | initiated) = 55/25/20 | 130.8 | 2.250 | 0.333 | 14.8 |
| E5D | | 118.2 | 2.033 | 0.356 | 17.5 |

*Formulations E5C and E5D were stored at RT for 6 days prior to extraction. Exenatide formulation was not stable.

The below Table lists the mass balance (the sum of % cumulative release of exenatide and % exenatide left in the depot after up to 6 days in the release medium) for all five exenatide depots.

| Formulation No. | Formulation wt (mg) | Exenatide weight (mg) by weight calculation | Exenatide wt (mg) left in the Depot by HPLC | % Remaining left in the Depot | % Cumulative release | Mass balance (% Cumulative release + % remaining left in the depot) |
|---|---|---|---|---|---|---|
| E1C | 113.4 | 1.996 | * | * | * | * |
| E1D | 110.8 | 1.950 | * | * | * | * |
| E1E | 111.2 | 1.957 | * | * | * | * |
| E2C | 118.1 | 1.937 | 0.318 | 16.4 | 81.7 | 98.1 |
| E2D | 116.6 | 1.912 | 0.356 | 18.6 | 81.3 | 99.9 |
| E2E | 120.0 | 1.968 | 0.393 | 20.0 | 82.9 | 102.9 |
| E3C | 122.9 | 2.089 | 1.806 | 86.4 | 13.8 | 110.2 |
| E3D | 120.8 | 2.054 | 0.643 | 31.3 | 27.3 | 58.6 |
| E3E | 123.0 | 2.091 | 1.841 | 88.1 | 18.1 | 106.2 |
| E4C | 118.5 | 2.015 | 0.204 | 10.1 | 91.5 | 101.6 |
| E4D | 117.8 | 2.003 | 0.651 | 32.5 | 59.4 | 91.9 |
| E4E | 117.9 | 2.004 | 0.974 | 48.6 | 51.9 | 100.5 |
| E5E | 111.9 | 1.925 | 0.643 | 33.4 | 65.1 | 98.5 |
| E5F | 105.6 | 1.816 | 1.373 | 75.6 | 23.6 | 99.2 |
| E5G | 110.4 | 1.899 | 0.898 | 47.3 | 25.6 | 72.9 |

*Exenatide degraded in formulation.

| Formulation No. | GLP-1 Analog (Concentration) | Vehicle Composition [wt %] | Dose Route | Dose Volume (µL) |
|---|---|---|---|---|
| G1 | GLP#1 (20 mg/mL) | SAIB/DMSO/PLA R202H (30/50/20) | SC | 20 |
| G2 | GLP#1 (20 mg/mL) | SAIB/EtOH/BA/PLA R202H (79/10/1/10) | SC | 20 |
| G3 | GLP#1 (20 mg/mL) | SAIB/NMP/BA/PLA R202H (65/15/10/10) | SC | 20 |
| G4 | GLP#2 (2 mg/mL) | SAIB/EtOH/BA/PLA R202H (79/10/1/10) | SC | 20 |
| G5 | GLP#2 (2 mg/mL) | SAIB/NMP/BA/PLA R202H (65/15/10/10) | SC | 20 |
| G6 | GLP#2 (2 mg/mL) | SAIB/NMP/EtOH/PLA R202H (55/10/15/20) | SC | 20 |

GLP#1 = a first GLP-1 Analog
GLP#2 = a second GLP-1 Analog

Blood samples were obtained at several intervals beginning on the day of dosing continuing up to Day 7. The concentration of GLP-1 analog in rat plasma samples was determined using an HPLC/MS/MS method.

Figure 12:
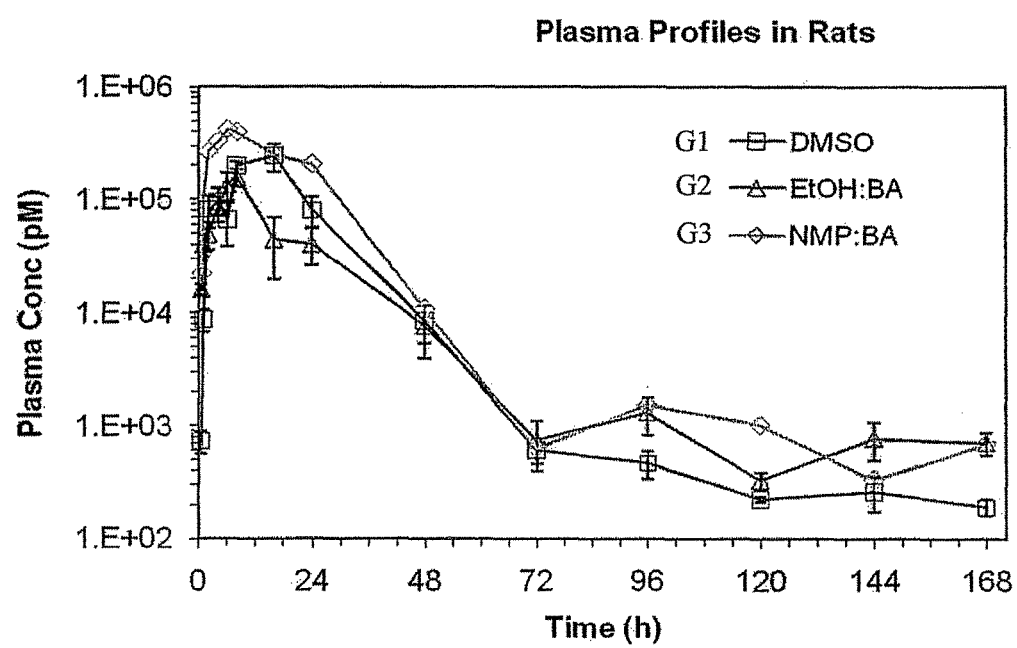
FIG. 12 shows the PK profile of a first GLP-1 analog in rats from compositions comprising the first GLP-1 analog, sucrose acetate isobutyrate, solvent (e.g., dimethylsulfoxide, benzyl alcohol, ethanol, and/or N-methyl-pyrrolidone), and a lactic acid-initiated poly(lactic acid) (PLA).
Figure 13:
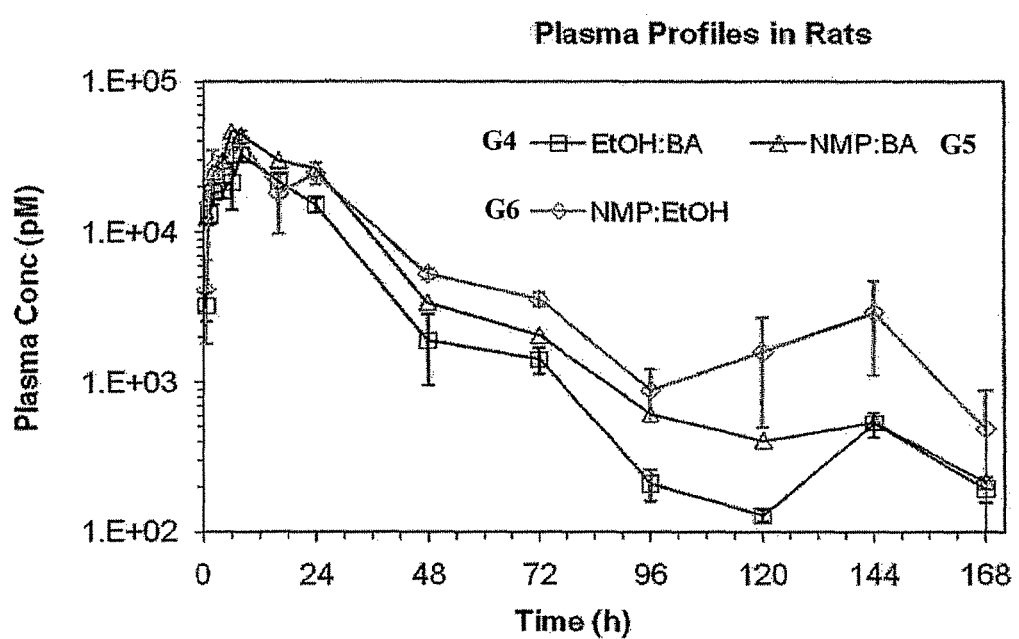
FIG. 13 shows the PK profile of a second GLP-1 analog in rats from compositions comprising the first GLP-1 analog, sucrose acetate isobutyrate, solvent (e.g., benzyl alcohol, ethanol, and/or N-methyl-pyrrolidone), and a lactic acid-initiated poly(lactic acid) (PLA).

The resulting mean PK profiles in rats of the GLP-1 analog #1 and GLP-1 analog #2 are shown in FIGS. 12 and 13, respectively (error bars are SEM). The results from this study showed that most of the GLP-1 analog release from the formulations occurred within a few days after subcutaneous (SC) administration of GLP-1 analog formulations in rats.

Example 8: Risperidone Formulations

Various risperidone formulations, such as those shown in Table 2, were prepared. Formulation Nos. R1 to R6 were solutions. Otherwise, the formulations were suspensions of risperidone. In Table 2, the proportion of vehicle components is shown in parts by weight, unless otherwise indicated.

Table 2 shows that the risperidone particles used to make the compositions were sometimes unmilled, but were typically milled by wet milling or jet milling.

The wet milling process was conducted using a standard agitator bead mill, such as Dynomill/MULTILAB from WAB. Risperidone was added to water (pH may be adjusted with ammonia solution as necessary) to form a slurry. The slurry was introduced into an agitator bead mill containing ceramic beads. The slurry was milled, with temperature control to keep the slurry below 20° C., such as about 15° C. Milling time in the wet milling equipment was monitored to yield the desired particle size. The slurry was then quickly transferred to a lyophilizer and lyophilized using standard lyophilization cycles. Water and ammonia were essentially removed during lyophilization. A an exemplary lyophilization cycle is shown below:

Freeze Cycle
  Shelf Temperature Set Point: −30° C.
  Duration: 180 mins (3 hrs)
Primary Drying
  Shelf Temperature Set Point: −6° C.
  Vacuum Set point: 700 mT
  Duration: 1440 mins (24 hrs)
Secondary Drying
  Shelf Temperature Set Point: 5° C.
  Vacuum Set point: 100 mT
  Duration: 1440 mins (24 hrs)

As shown in Table 2, aqueous wet milling was sometimes performed in the presence of additives, the proportion of which is shown in parts by weight. When Pluronic F68 or Lutrol F68 was used as a milling additive without any other additives, the weight ratio of risperidone to F68 ranged from 95:5 to 70:30, unless otherwise indicated.

The jet milling process involved comminuting the risperidone using a jet mill, e.g., using a Jet-O-Mizer jet mill. Multiple passes through the jet mill were sometimes used to achieve the desired reduction of the initial particle size. Liquid nitrogen was at least typically used to assist in the fracture of the particles during this milling process.

Before milling, the as received particles typically had a median particle size, as measured by laser diffraction, ranging from 10 µm to 50 µm, with some as received lots having particles as large as 300 µm. When particles were jet milled, the resulting particles typically had a median particle size, as measured by laser diffraction, ranging from 2 µm to 10 µm. When particles were wet milled and lyophilized, the resulting particles typically had a median particle size, as measured by laser diffraction, ranging from 1 µm to 10 µm.

Risperidone particles were combined with vehicle using standard methods. For instance, the particles were weighed in a glass jar. Vehicle was added. The mixture was homogenized using a PowerGen 1000 homogenizer, e.g., set at setting 2 to setting 4 for a total of 4-6 minutes.

Table 2 includes the following abbreviations:
RSP: risperidone
SAIB: sucrose acetate isobutyrate
NMP: N-methyl-pyrrolidone
DMSO: dimethylsulfoxide
CremophorEL: Cremophor EL
Pluronic L44: Pluronic L44
BB: benzyl benzoate
PC: propylene carbonate
DMA: dimethylacetamide
Solutol: Solutol® HS 15 polyoxyethylene esters of 12-hydroxystearic acid
PLGA: poly(lactic acid)(glycolic acid)
PLA: poly(lactic acid)
PLA R202H: Resomer 202H poly(lactic acid)
DD: dodecanol
LA: lactic acid
L:G: molar ratio of lactic acid to glycolic acid
C8: octanol
C16: 1-hexadecanol
PVP: Plasdone C-17 polyvinylpyrrolidone
F68: Lutrol F68 or Pluronic F68
HPMC: hydroxypropyl methylcellulose
Tween 20: polyoxyethylene (20) sorbitan monolaurate
Tween 80: polyoxyethylene (20) sorbitan monooleate
CMC: sodium caboxymethylcellulose
DOC: deoxycholate

TABLE 2

| Form. No. | Vehicle | Initiator | PLGA or PLA L:G | Mw (kDa) | RSP (wt %) | RSP Milling Conditions |
|---|---|---|---|---|---|---|
| R1 | SAIB/BA/EtOH/PLA R202H (45/22.5/12.5/10) | LA | 100:0 | 14 | 10 | Not milled |
| R2 | SAIB/BA/EtOH/PLA R202H (35/22.5/12.5/20) | LA | 100:0 | 14 | 10 | Not milled |
| R3 | SAIB/BA/EtOH/PLA R202H (25/22.5/12.5/30) | LA | 100:0 | 14 | 10 | Not milled |
| R4 | SAIB/BA/BB/PLA R202H (40/20/10/20) | LA | 100:0 | 14 | 10 | Not milled |
| R5 | SAIB/BA/BB/PLA R202H (40/25/5/20) | LA | 100:0 | 14 | 10 | Not milled |
| R6 | SAIB/BA/BB/PLA R202H/RSP (30/25/5/30/10) | LA | 100:0 | 14 | 10 | Not milled |
| R7 | SAIB/NMP/PLGA (55/25/20) | HD | 65:35 | 5.1 | 10 | Jet milled |
| R7* | SAIB/NMP/PLGA (55/25/20) | HD | 65:35 | 5.1 | 10 | Not milled |
| R8 | SAIB/DMSO/PLGA 50/22/18 | DD | 65:35 | 6.3 | 10 | Jet milled |
| R9 | SAIB/DMSO/PLGA/PLA R202H 50/22/9/9 | DD LA | 65:35 100:0 | 6.3 14 | 10 | Jet milled |
| R10 | SAIB/NMP/PLGA (55/25/20) | DD | 65:35 | 6.3 | 10 | Jet milled |
| R11 | SAIB/NMP/PLGA (55/25/20) | DD | 65:35 | 6.3 | 17.5 | Jet milled |
| R12 | SAIB/NMP/PLGA (45/25/30) | DD | 65:35 | 6.5 | 10 | Jet milled |
| R13 | SAIB/NMP/PLGA (45/25/30) | DD | 65:35 | 6.5 | 17.5 | Jet milled |
| R14 | SAIB/NMP/PLGA (60/20/20) | DD | 65:35 | 6.5 | 10 | Jet milled |
| R15 | SAIB/NMP/DMSO/PLGA (55/15/10/20) | DD | 65:35 | 6.5 | 10 | Jet milled |
| R16 | SAIB/NMP/PLGA (60/20/20) | DD | 65:35 | 6.5 | 17.5 | Jet milled |
| R17 | SAIB/NMP/PLGA (55/25/20) | DD | 65:35 | 6.3 | 9 | Jet milled |
| R18 | SAIB/NMP/DMSO/PLGA (55/15/5/25) | DD | 65:35 | 6.5 | 10 | Jet milled |
| R19 | SAIB/NMP/DMSO/PLGA (55/15/7/23) | DD | 65:35 | 6.5 | 9 | Jet milled |
| R20 | SAIB/NMP/DMSO/PLGA (55/15/7/23) | DD | 65:35 | 6.5 | 17.5 | Jet milled |
| R21 | SAIB/PC/PLGA (55/25/20) | DD | 65:35 | 6.5 | 9 | Jet milled |
| R22 | SAIB/NMP/PLGA (55/25/20) | DD | 65:35 | 6.3 | 9 | Wet milled in 1 wt % PEG4000 |
| R23 | SAIB/NMP/PLGA (55/25/20) | DD | 65:35 | 6.3 | 9 | Wet milled in 1 wt % PVP |
| R24 | SAIB/PC/PLGA (50/30/20) | DD | 65:35 | 6.5 | 9 | Jet milled |
| R25 | SAIB/NMP/PLGA (55/25/20) | DD | 65:35 | 6.3 | 9 | Not milled |
| R26 | SAIB/NMP/PLGA (55/25/20) | DD | 65:35 | 6.3 | 5 | Jet milled |
| R27 | SAIB/NMP/PLGA (55/25/20) | DD | 65:35 | 6.3 | 25 | Jet milled |
| R28 | SAIB/NMP/PLGA (55/25/20) | DD | 65:35 | 6.3 | 35 | Jet milled |
| R29 | SAIB/NMP/PLGA (55/25/20) | DD | 65:35 | 6.3 | 9 | Wet milled in 10 wt % F68 |
| R30 | SAIB/NMP/PLGA (55/25/20) | DD | 75:25 | 6.5 | 9 | Jet milled |
| R31 | SAIB/NMP/PLGA (55/25/20) | DD | 75:25 | 6.5 | 9 | Wet milled for 10 minutes |
| R32 | SAIB/NMP/PLGA (55/25/20) | DD | 75:25 | 6.5 | 9 | Wet milled at slow rpm for 35 minutes |
| R33 | SAIB/NMP/PLGA (55/25/20) | DD | 75:25 | 6.5 | 9 | Wet milled with 95 RSP:5 PVP |
| R34 | SAIB/NMP/PLGA (55/25/20) | DD | 75:25 | 6.5 | 9 | Wet milled with 95 RSP:5 HPMC |
| R35 | SAIB/NMP/PLGA (55/25/20) | DD | 75:25 | 6.5 | 17.5 | Wet milled for 10 minutes |

TABLE 2-continued

| Form. No. | Vehicle | PLGA or PLA Initiator | L:G | Mw (kDa) | RSP (wt %) | RSP Milling Conditions |
|---|---|---|---|---|---|---|
| R36 | SAIB/NMP/PLGA (55/25/20) | DD | 75:25 | 6.5 | 17.5 | Wet milled at slow rpm for 35 minutes |
| R37 | SAIB/NMP/PLGA (55/25/20) | DD | 75:25 | 6.5 | 17.5 | Wet milled with 95 RSP:5 PVP |
| R38 | SAIB/NMP/PLGA (55/25/20) | DD | 75:25 | 6.5 | 17.5 | Wet milled |
| R39 | SAIB/NMP/PLGA (55/25/20) | DD | 75:25 | 6.9 | 9 | Wet milled for 10 minutes |
| R40 | SAIB/NMP/PLGA (55/25/20) | DD | 75:25 | 6.9 | 9 | Wet milled with 95 RSP:5 PVP |
| R41 | SAIB/NMP/PLGA (55/25/20) | DD | 75:25 | 6.9 | 9 | Jet milled |
| R42 | SAIB/NMP/PLGA (55/25/20) | DD | 75:25 | 6.9 | 9 | Wet milled |
| R43 | SAIB/NMP/PLGA/PLA R202H (55/25/17.5/2.5) | DD LA | 85:15 100:0 | 7.7 14 | 9 | Wet milled |
| R44 | SAIB/NMP/PLGA (52.5/27.5/20) | DD | 75:25 | 6.9 | 17.5 | Wet milled |
| R45 | SAIB/NMP/DMSO/PLGA (50/25/5/20) | DD | 75:25 | 5.9 | 9 | Wet milled |
| R46 | SAIB/NMP/DMSO/PLGA (50/25/5/20) | DD | 75:25 | 5.9 | 17.5 | Wet milled |
| R47 | SAIB/NMP/DMSO/PLGA (52/19/9/20) | DD | 75:25 | 5.9 | 9 | Wet milled |
| R48 | SAIB/NMP/DMSO/PLGA (52/19/9/20) | DD | 75:25 | 5.9 | 17.5 | Wet milled |
| R49 | SAIB/NMP/PLGA (55/25/20) | DD | 75:25 | 6.9 | 17.5 | Wet milled with 95 RSP:5 PVP |
| R50 | SAIB/NMP/PLGA (55/25/20) | DD | 75:25 | 6.9 | 9 | Wet milled with F68 |
| R51 | SAIB/NMP/PLGA (55/25/20) | DD | 75:25 | 6.9 | 17.5 | Wet milled with F68 |
| R52 | SAIB/NMP/PLGA (55/25/20) | DD | 75:25 | 6.9 | 9 | Wet milled 8 minutes |
| R53 | SAIB/NMP/PLGA (50/30/20) | DD | 75:25 | 6.9 | 9 | Wet milled 12 minutes |
| R54 | SAIB/NMP/PLGA (48/32/20) | DD | 75:25 | 6.9 | 9 | Wet milled 12 minutes |
| R55 | SAIB/NMP/PLGA (48/32/20) | DD | 75:25 | 6.9 | 17.5 | Wet milled 12 minutes |
| R56 | SAIB/NMP/PLGA (51/29/20) | DD | 75:25 | 6.9 | 9 | Wet milled 12 minutes |
| R57 | SAIB/NMP/PLGA (50.5/29.5/20) | DD | 75:25 | 6.9 | 9 | Wet milled 12 minutes |
| R58 | SAIB/NMP/DMSO/PLGA (50/25/5/20) | DD | 75:25 | 6.9 | 9 | Wet milled 12 minutes |
| R59 | SAIB/NMP/PLGA (50/30/20) | DD | 75:25 | 6.9 | 9 | Wet milled 12 minutes |
| R60 | SAIB/NMP/DMSO/PLGA (48/21/11/20) | DD | 75:25 | 6.9 | 9 | Wet milled 12 minutes |
| R61 | SAIB/NMP/PLGA (55/25/20) | DD | 75:25 | 7.0 | 9 | Wet milled 12 minutes |
| R62 | SAIB/NMP/PLGA (55/25/20) | DD | 75:25 | 7.0 | 9 | Wet milled |
| R63 | SAIB/NMP/PLGA (55/25/20) | DD | 75:25 | 7.0 | 9 | Jet milled |
| R64 | SAIB/NMP/PLGA (55/25/20) | DD | 75:25 | 7.0 | 9 | Wet milled 8 minutes |
| R65 | SAIB/NMP/PLGA (50/30/20) | DD | 75:25 | 7.0 | 9 | Wet milled 12 minutes |
| R66 | SAIB/NMP/PLGA (50/30/20) | DD | 75:25 | 7.0 | 9 | Wet milled |
| R67 | SAIB/NMP/PLGA (50/30/20) | DD | 75:25 | 7.0 | 9 | Jet milled |
| R68 | SAIB/NMP/DMSO/PLGA (50/20/10/20) | DD | 75:25 | 6.9 | 9 | Jet milled |
| R69 | SAIB/NMP/DMSO/PLGA (50/20/10/20) | DD | 75:25 | 6.9 | 9 | Wet milled |
| R70 | SAIB/NMP/PLGA (46/34/20) | DD | 75:25 | 7.0 | 17.5 | Wet milled |
| R71 | SAIB/NMP/PLGA (46/34/20) | DD | 75:25 | 7.0 | 17.5 | Wet milled |
| R72 | SAIB/NMP/PLGA (46/34/20) | DD | 75:25 | 7.0 | 17.5 | Wet milled with F68 |

TABLE 2-continued

| Form. No. | Vehicle | PLGA or PLA Initiator | L:G | Mw (kDa) | RSP (wt %) | RSP Milling Conditions |
|---|---|---|---|---|---|---|
| R73 | SAIB/NMP/DMSO/PLGA (46/22.5/11.5/20) | DD | 75:25 | 7.0 | 17.5 | Wet milled |
| R74 | SAIB/NMP/PLGA (50/30/20) | DD | 75:25 | 7.0 | 9 | Wet milled 36 minutes |
| R75 | SAIB/NMP/PLGA (50/30/20) | DD | 75:25 | 7.0 | 9 | Wet milled 46 minutes |
| R76 | SAIB/NMP/PLGA (50/30/20) | DD | 75:25 | 7.0 | 9 | Wet milled 46 minutes with 95 RSP:5 PVP |
| R77 | SAIB/NMP/PLGA (50/30/20) | DD | 75:25 | 7.0 | 9 | Wet milled 8 minutes with 95 RSP:5 PVP |
| R78 | SAIB/NMP/DMSO/PLGA (50/20/10/20) | DD | 75:25 | 7.0 | 9 | Wet milled 46 minutes |
| R79 | SAIB/NMP/PLGA (52/29/19) | DD | 75:25 | 7.0 | 9 | Wet milled 46 minutes |
| R80 | 0.9 wt % paliperidone in SAIB/NMP/PLGA (52/29/19) | DD | 75:25 | 7.0 | 9 | Wet milled 90 minutes |
| R81 | SAIB/NMP/PLGA (50/30/20) | DD | 75:25 | 7.0 | 9 | Wet milled 46 minutes with F68 |
| R82 | SAIB/NMP/PLGA (50/30/20) | DD | 75:25 | 7.0 | 9 | Wet milled 46 minutes with 95 RSP:2.5 F68:2.5 Tween 80 |
| R83 | SAIB/NMP/PLGA (55/25/20) | DD | 75:25 | 7.0 | 9 | Wet milled 46 minutes |
| R84 | SAIB/NMP/PLGA (50/30/20) | DD | 75:25 | 7.0 | 9 | Wet milled with 95 RSP:5 CMC |
| R85 | SAIB/NMP/PLGA (50/30/20) | DD | 75:25 | 7.0 | 9 | Wet milled 46 minutes with 95 RSP:5 Tween 20 |
| R86 | SAIB/NMP/PLGA (50/30/20) | DD | 75:25 | 7.0 | 9 | Wet milled 46 minutes with 95 RSP:2.5 PVP:2.5 DOC |
| R87 | SAIB/NMP/PLGA (50/30/20) | DD | 75:25 | 7.0 | 9 | Wet milled 90 minutes with F68 |
| R88 | SAIB/NMP/PLGA (50/30/20) | DD | 75:25 | 7.0 | 9 | Wet milled 90 minutes |
| R89 | SAIB/NMP/PLGA (50/30/20) | DD | 75:25 | 7.0 | 9 | Wet milled with 80 RSP:20 F68 |
| R90 | SAIB/NMP/PLGA (50/30/20) | DD | 75:25 | 7.0 | 9 | Wet milled with 95 RSP:5 mannitol |
| R91 | SAIB/PC/PLGA (44/36.5/19.5) | DD | 75:25 | 7.0 | 9 | Wet milled 46 minutes |
| R92 | SAIB/NMP/PLGA (44/36/20) | DD | 75:25 | 7.0 | 9 | Wet milled |
| R93 | SAIB/NMP/PLGA (40/40/20) | DD | 75:25 | 7.0 | 9 | Wet milled |
| R94 | SAIB/NMP/PLGA (31/49/20) | DD | 75:25 | 7.0 | 9 | Wet milled |
| R95 | SAIB/NMP/PLGA (50/30/20) | DD | 75:25 | 7.0 | 10 | Wet milled 46 minutes |
| R96 | SAIB/NMP/PLGA (50/30/20) | DD | 75:25 | 7.0 | 10 | Wet milled with RSP:F68 95:5 |
| R97 | SAIB/NMP/PLGA (50/30/20) | DD | 75:25 | 7.0 | 9 | Wet milled with RSP:F68 90:10 |
| R98 | SAIB/NMP/PLGA (50/30/20) | DD | 75:25 | 7.0 | 9 | Wet milled with RSP:F68 80:20 |
| R99 | SAIB/NMP/PLGA (52/29/19) | DD | 75:25 | 7.0 | 9 | Wet milled with F68 |
| R100 | SAIB/NMP/PLGA (58/27/15) | DD | 75:25 | 7.0 | 9 | Wet milled 46 minutes |
| R101 | SAIB/NMP/PLGA (55/28/17) | DD | 75:25 | 7.0 | 9 | Wet milled 46 minutes |
| R102 | SAIB/PC/PLGA (44/37/19) | DD | 75:25 | 7.0 | 9 | Wet milled 46 minutes |

TABLE 2-continued

| Form. No. | Vehicle | PLGA or PLA Initiator | L:G | Mw (kDa) | RSP (wt %) | RSP Milling Conditions |
|---|---|---|---|---|---|---|
| R103 | SAIB/NMP/DMSO/PLGA (50/15.5/14.5/20) | DD | 75:25 | 7.0 | 9 | Wet milled 90 minutes |
| R104 | SAIB/NMP/DMSO/PLGA (49.5/10/20.5/20) | DD | 75:25 | 7.0 | 9 | Wet milled 90 minutes |
| R105 | SAIB/DMSO/PLGA (48/32/20) | DD | 75:25 | 7.0 | 9 | Wet milled 90 minutes |
| R106 | SAIB/PC/PLGA (38/42/20) | DD | 75:25 | 7.0 | 9 | Wet milled |
| R107 | SAIB/PC/PLGA (34/46/20) | DD | 75:25 | 7.0 | 9 | Wet milled |
| R108 | SAIB/PC/PLGA (28/52/20) | DD | 75:25 | 7.0 | 9 | Wet milled |
| R109 | SAIB/NMP/DMSO/PLGA (50/20/10/20) | DD | 75:25 | 7.0 | 9 | Wet milled 90 minutes |
| R110 | SAIB/NMP/DMSO/PLGA (50/20/10/20) | DD | 75:25 | 7.0 | 9 | Wet milled 90 minutes with sucrose |
| R111 | SAIB/NMP/DMSO/PLGA (50/20/10/20) | DD | 75:25 | 7.0 | 9 | Wet milled 90 minutes with trehalose |
| R112 | SAIB/NMP/DMSO/PLGA (50/20/10/20) | DD | 75:25 | 7.0 | 9 | Wet milled 180 minutes with 95 RSP:5 CMC |
| R113 | SAIB/NMP/DMSO/PLGA (50/20/10/20) | DD | 75:25 | 7.0 | 9 | Wet milled with 95 RSP:2.5 CMC:2.5 F68 |
| R114 | SAIB/NMP/DMSO/PLGA (50/20/10/20) | DD | 75:25 | 7.0 | 9 | Wet milled 180 minutes with F68 |
| R115 | SAIB/NMP/PLGA (50/30/20) | DD | 75:25 | 7.0 | 9 | Wet milled 130 minutes |
| R116 | SAIB/NMP/PLGA (50/30/20) | DD | 75:25 | 7.0 | 9 | Wet milled 130 minutes with 95 RSP:5 arginine |
| R117 | SAIB/NMP/PLGA (50/30/20) | DD | 75:25 | 7.0 | 9 | Wet milled 130 minutes with 95 RSP:5 dextran |
| R118 | SAIB/NMP/PLGA (50/30/20) | DD | 75:25 | 7.0 | 9 | Wet milled 130 minutes with 95 RSP:2.5 PVP:2.5 DOC |
| R119 | SAIB/NMP/PLGA (50/30/20) | DD | 75:25 | 7.0 | 9 | Wet milled 240 minutes |
| R120 | SAIB/NMP/PLGA (50/30/20) | DD | 75:25 | 7.0 | 9 | Wet milled 240 minutes with DOC |
| R121 | SAIB/NMP/PLGA (50/30/20) | DD | 75:25 | 7.0 | 9 | Wet milled 240 minutes with 95 RSP:2.5 DOC:2.5 F68 |
| R122 | SAIB/NMP/PLGA (50/30/20) | DD | 75:25 | 7.0 | 9 | Wet milled 240 minutes with 95 RSP:2.5 PVP:2.5 DOC |
| R123 | SAIB/NMP/PLGA (50/30/20) | DD | 75:25 | 7.0 | 9 | Wet milled 240 minutes with 95 RSP:2.5 PVP:2.5 CMC |
| R124 | SAIB/NMP/PLGA (50/30/20) | DD | 75:25 | 7.0 | 9 | Wet milled 90 minutes with F68 |
| R125 | SAIB/PC/PLGA (44/37/19) | DD | 75:25 | 7.0 | 9 | Wet milled 200 minutes |
| R126 | SAIB/NMP/PC/PLGA (46/10/24/20) | DD | 75:25 | 7.0 | 9 | Wet milled 90 minutes |
| R127 | SAIB/NMP/PC/PLGA (48/20/12/20) | DD | 75:25 | 7.0 | 10 | Wet milled 90 minutes |
| R128 | SAIB/DMA/PLGA (56/24/20) | DD | 75:25 | 7.0 | 9 | Wet milled 130 minutes |
| R129 | SAIB/NMP/Miglyol/PLGA (49.5/29.5/1/20) | DD | 75:25 | 7.0 | 9 | Wet milled 180 minutes |
| R130 | SAIB/NMP/Miglyol/PLGA (47/28/5/20) | DD | 75:25 | 7.0 | 9 | Wet milled 180 minutes |
| R131 | SAIB/PC/PLGA (44/37/19) | DD | 75:25 | 7.0 | 9 | Wet milled |

TABLE 2-continued

| Form. No. | Vehicle | Initiator | L:G | PLGA or PLA Mw (kDa) | RSP (wt %) | RSP Milling Conditions |
|---|---|---|---|---|---|---|
| R132 | SAIB/NMP/PC/PLGA (46/10/24/20) | DD | 75:25 | 7.0 | 9 | Wet milled |
| R133 | SAIB/NMP/PLGA (54.5/27.5/18) | DD | 75:25 | 7.0 | 9 | Jet milled |
| R134 | SAIB/PC/PLGA (37/43/20) | DD | 75:25 | 7.0 | 17.5 | Wet milled |
| R135 | SAIB/PC/PLGA (30/50/20) | DD | 75:25 | 7.0 | 17.5 | Wet milled |
| R136 | SAIB/PC/DMSO/PLGA (46/17/17/20) | DD | 75:25 | 7.0 | 9 | Wet milled |
| R137 | SAIB/NMP/PLGA (50/30/20) | DD | 75:25 | 7.0 | 8.9 | Wet milled |
| R138 | SAIB/NMP/PLGA (48/32/20) | DD | 75:25 | 7.0 | 17.5 | Wet milled |
| R139 | SAIB/NMP/PLGA (55/25/20) | C8 | 65:35 | 5.4 | 9 | Wet milled |
| R140 | SAIB/NMP/PLGA (55/25/20) | C16 | 65:35 | 5.8 | 9 | Wet milled |
| R141 | SAIB/NMP/PLA (55/25/20) | DD | 100:0 | 13.9 | 9 | Wet milled |

Example 9: Settling in N-methylpyrrolidone and Propylene Carbonate Formulations As discussed in more detail below, this Example was directed to comparing the risperidone particle settling behavior of suspension formulations based on N-methylpyrrolidone as compared with suspension formulations based on propylene carbonate. Real-time settling was analyzed.

Formulation No. R66 consisted of SAIB/NMP/PLGA/RSP in the following weight proportion: 45.5/27.3/18.2/9.0. Formulation No. R131 consisted of SAIB/PC/PLGA/RSP in the following weight proportions 40.0/33.7/17.3/9.0. It should be noted that Formulation Nos. R66 and R131 were formulated to yield approximately the same viscosity (see below Table). However, to achieve similar viscosities, more PC must be added to the vehicle, with a corresponding decrease in SAIB (and a minor decrease in PLGA).

|  | Formulation No. R66 (NMP formulation) | Formulation No. 131 (PC formulation) |
|---|---|---|
| Placebo Vehicle Composition | SAIB/NMP/PLGA: 50/30/20 | SAIB/PC/PLGA: 44/37/19 |
| Placebo Vehicle Density (gm/mL) | 1.123 | 1.179 |
| Viscosity of placebo vehicle at 25° C. | 374 cP | 372 cP |
| Viscosity of placebo vehicle at 5° C. | 2100-2300 cP @ 6-8 s$^{-1}$ | 1750-1900 cP @ 6-8 s$^{-1}$ |
| Risperidone solubility in vehicle | 9.2 mg/mL | 7.4 mg/mL |
| Viscosity of formulation at 25° C. (i.e., with 9% RSP) | 656 cP | 721 cP |

Starting RSP particle size (post milling & lyophilization) for both Formulation No. R66 and Formulation No. R131 was D(0.1)=0.63 µm, D(0.5)=1.99 µm, and D(0.9)=3.94 µm.

Formulation Nos. R66 and R131 were gamma irradiated at 15 kGy.

The below Table shows the real-time settling of samples stored at the indicated conditions. About 2 mL of each of the formulations was placed in tubes. After the indicated storage times, 100 µL aliquots were removed from the very top, middle and bottom layer of the tubes and weighed into 25 mL volumetric flasks. Samples were extracted and assayed for the potency using HPLC.

Figure 14:
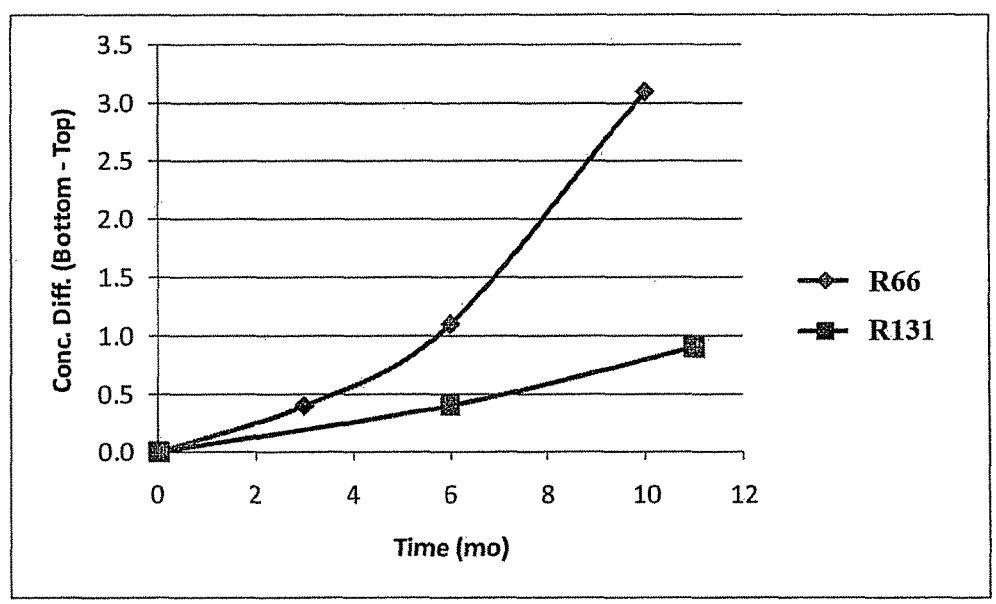
FIG. 14 compares the real time settling behavior of risperidone particles in a composition based on N-methyl-pyrrolidone versus a composition based on propylene carbonate, both stored at 5° C.

The below Table, which is graphically summarized in FIG. 14, shows the real time settling behavior of Formulations No. R66 (NMP based) and Formulation No. R131 (PC based) at 5° C.

| Formulation | Composition | Storage Condition | % RSP Top-Bottom | Difference (Bottom-Top) |
|---|---|---|---|---|
| R66 | SAIB/NMP/PLGA/RSP 45.5/27.3/18.2/9.0 | T0 (post irradiation) | 9.00% | 0 |
|  |  | 6 months @−20° C. | 8.8-8.9% | 0.1% |
|  |  | 10 months @−20° C. | 8.8-8.8% | 0 |
|  |  | 3 months @5° C. | 8.9-9.3% | 0.4% |
|  |  | 6 months @5° C. | 8.6-9.7% | 1.1% |
|  |  | 10 months @5° C. | 6.7-9.8% | 3.1% |

-continued

| Formulation | Composition | Storage Condition | % RSP Top-Bottom | Difference (Bottom-Top) |
|---|---|---|---|---|
| R131 | SAIB/PC/PLGA/RSP 40.0/33.7/17.3/9.0 | T0 (post irradiation) | 9.01% | 0 |
| | | 6 months @5° C. | 8.9-9.3% | 0.4% |
| | | 11 months @5° C. | 9.3%-10.2% | 0.9% |
| | | 1 month @25° C. | 8.9%-9.2% | 0.3% |
| | | 11 months @25° C. | 8.6%-11.8% | 3.2% |

The difference in the above-noted settling versus the difference in vehicle density is notable. As shown in the first Table of this Example, the viscosity of the placebo vehicle for Formulation No. R66 at 5° C. is slightly higher than the viscosity of the placebo vehicle for Formulation No. R131 at 5° C. The density of risperidone is 1.30 g/mL. Thus, the difference in density between risperidone and each of the vehicles was:

$\rho_1-\rho_2$=1.30 g/mL−1.123 g/mL=0.177 g/mL for Formulation No. R66

$\rho_1-\rho_2$=1.30 g/mL−1.179 g/mL=0.121 g/mL for Formulation No. R131

Thus, the density difference between the placebo vehicles for Formulation Nos. R66 and R131 is about 46%.

The concentration difference for real time settling is relatively higher. As shown above in the second Table of this Example, the difference in settling is 3.1% (bottom−top) for Formulation No. R66 at 10 months at 5° C. versus 0.9% (bottom−top) for Formulation No. R131 at 11 months at 5° C.

In view of the above, the density difference is only about 46%, but the concentration difference for real-time settling is close to 250%.

Example 10: Risperidone In Vitro Release from Formulations Comprising Various Polymers As discussed in more detail below, this Example was directed to comparing the risperidone in vitro release behavior of formulations comprising risperidone, sucrose acetate isobutyrate, N-methyl-pyrrolidone, and polymer (poly(lactic acid)(glycolic acid) or poly(lactic acid)).

Specifically, the in vitro release behavior of the following formulations was characterized.

An aliquot (0.5 mL) of each composition was placed in 100 mL of phosphate buffered saline (PBS) at 37° C. with gentle stirring (n=4). The release into the PBS was monitored.

Figure 15:
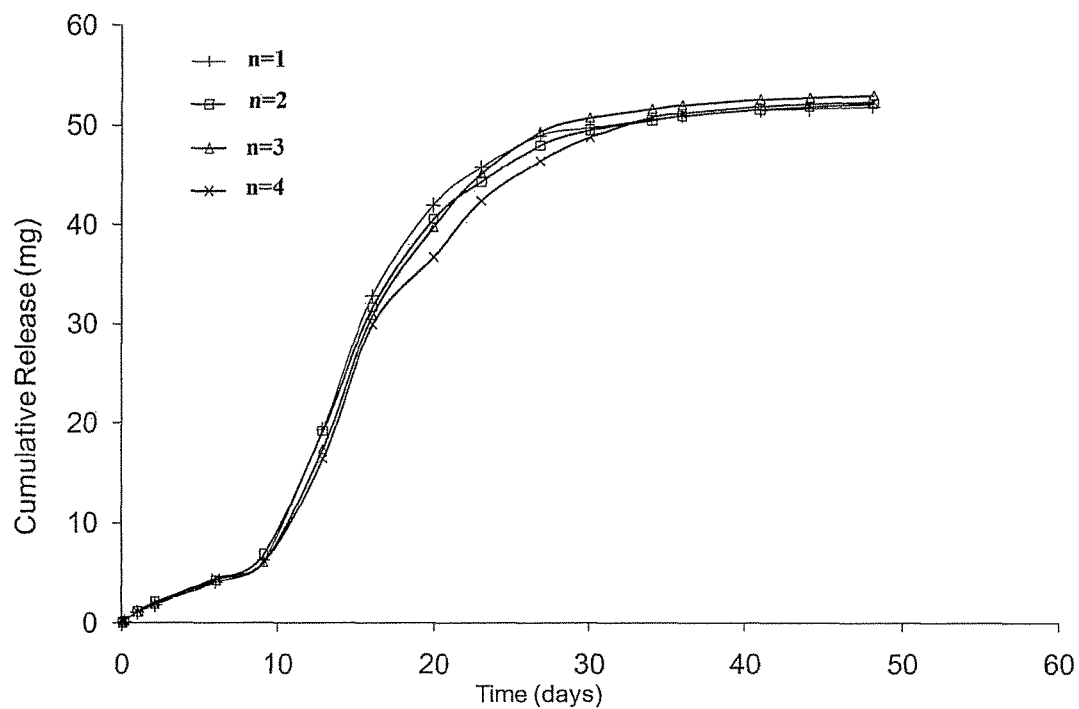
FIG. 15 shows in vitro release of risperidone from a vehicle comprising sucrose acetate isobutyrate, N-methyl-pyrrolidone, and octanol-initiated poly(lactic acid)(glycolic acid).
Figure 16:
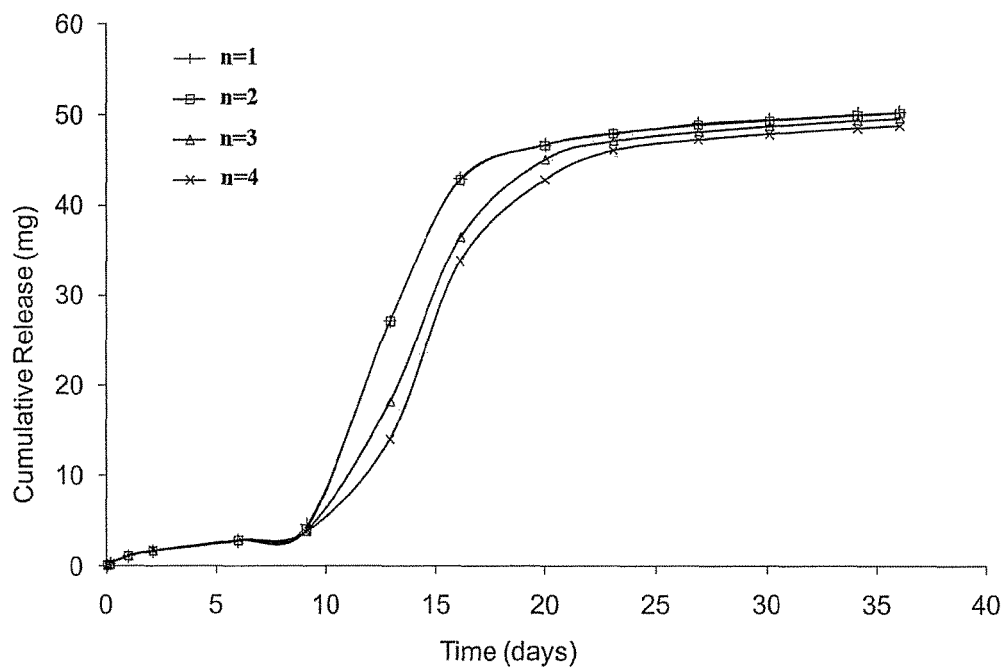
FIG. 16 shows in vitro release of risperidone from a vehicle comprising sucrose acetate isobutyrate, N-methyl-pyrrolidone, and hexadecanol-initiated poly(lactic acid)(glycolic acid).
Figure 17:
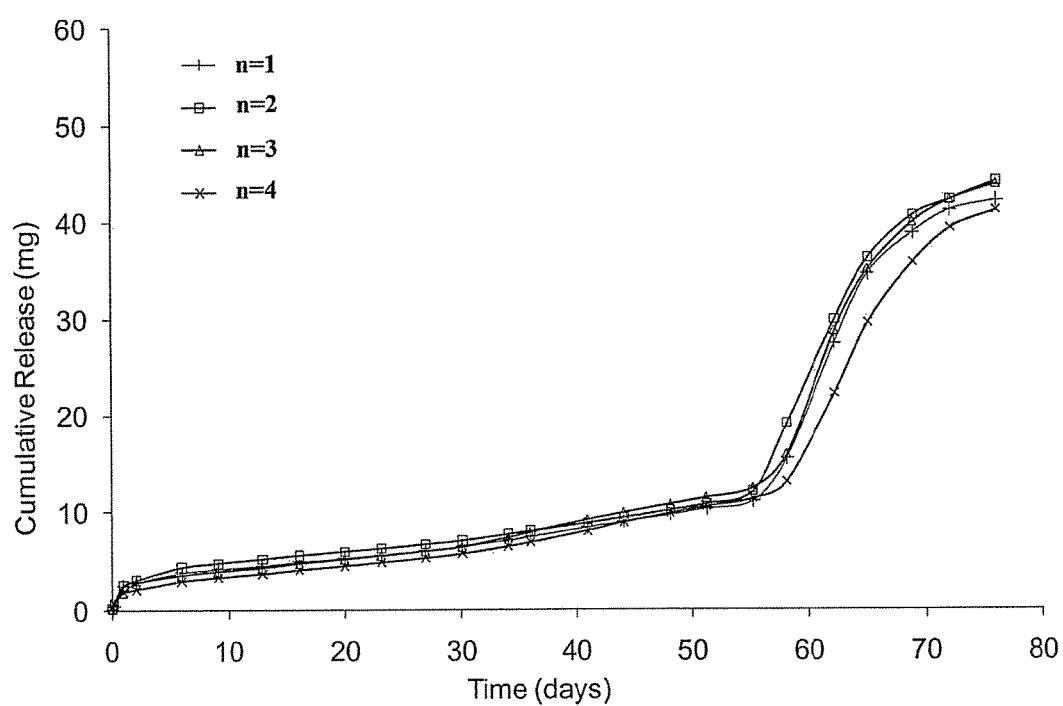
FIG. 17 shows in vitro release of risperidone from a vehicle comprising sucrose acetate isobutyrate, N-methyl-pyrrolidone, and dodecanol-initiated poly(lactic acid).

The cumulative release profiles are shown in FIGS. 15 to 17. Each of the formulations showed extended release of risperidone for at least 20 days.

Example 11: Risperidone In Vivo Release in Rats

As discussed in more detail below, this Example was directed to in vivo release in rats of risperidone from formulations comprising risperidone, sucrose acetate isobutyrate, solvent (e.g., benzyl alcohol, ethanol, benzyl benzoate, and N-methyl-pyrrolidone), and polymer (e.g., hexanediol-initiated poly(lactic acid) (PLA) and poly(lactic acid) (glycolic acid) (PLGA)).

The PK of each of seven risperidone-vehicle formulations, shown in the below Table, was evaluated in male Sprague-Dawley rats (N=6/group) following SC administration. The risperidone in the formulations of Groups 1-6 was in solution, whereas the risperidone in the formulation of Group 7 was in suspension. A control group in which risperidone was delivered by IV bolus administration was also included for the purpose of determining SC bioavailability.

| Formulation No. | Vehicle | PLGA or PLA | | | RSP (wt %) | RSP Milling Conditions |
|---|---|---|---|---|---|---|
| | | Initiator | L:G | Mw (kDa) | | |
| R139 | SAIB/NMP/PLGA (55/25/20) | C8 | 65:35 | 5.4 | 9 | Wet milled |
| R140 | SAIB/NMP/PLGA (55/25/20) | C16 | 65:35 | 5.8 | 9 | Wet milled |
| R141 | SAIB/NMP/PLA (55/25/20) | DD | 100:0 | 13.9 | 9 | Wet milled |

| Group | Formulation No. | Formulation Composition [wt %] | PLGA or PLA Initiator | L:G | Mw (kDa) | Dose Route | Dose Volume (µL) |
|---|---|---|---|---|---|---|---|
| 1 | R1 | SAIB/BA/EtOH/PLA R202H/RSP (45/22.5/12.5/10/10) | LA | 100:0 | 14 | SC | 100 |
| 2 | R2 | SAIB/BA/EtOH/PLA R202H/RSP (35/22.5/12.5/20/10) | LA | 100:0 | 14 | SC | 100 |
| 3 | R3 | SAIB/BA/EtOH/PLA R202H/RSP (25/22.5/12.5/30/10) | LA | 100:0 | 14 | SC | 100 |
| 4 | R4 | SAIB/BA/BB/PLA R202H/RSP (40/20/10/20/10) | LA | 100:0 | 14 | SC | 100 |
| 5 | R5 | SAIB/BA/BB/PLA R202H/RSP (40/25/5/20/10) | LA | 100:0 | 14 | SC | 100 |
| 6 | R6 | SAIB/BA/BB/PLA R202H/RSP (30/25/5/30/10) | LA | 100:0 | 14 | SC | 100 |
| 7 | R7 | 10 wt % RSP in SAIB/NMP/PLGA (55/25/20) | HD | 65:35 | 5.1 | SC | 100 |
| 8 | NA | 0.4 mg/mL RSP in pH 5.4 citrate buffer | NA | NA | NA | IV bolus | 300 |

RSP = Risperidone

Blood samples were obtained at several intervals beginning on the day of dosing continuing up to Day 28. The concentration of risperidone and 9-OH risperidone (a major metabolite that is pharmacologically active) in rat plasma samples was determined using an HPLC/MS/MS method.

Figure 18:
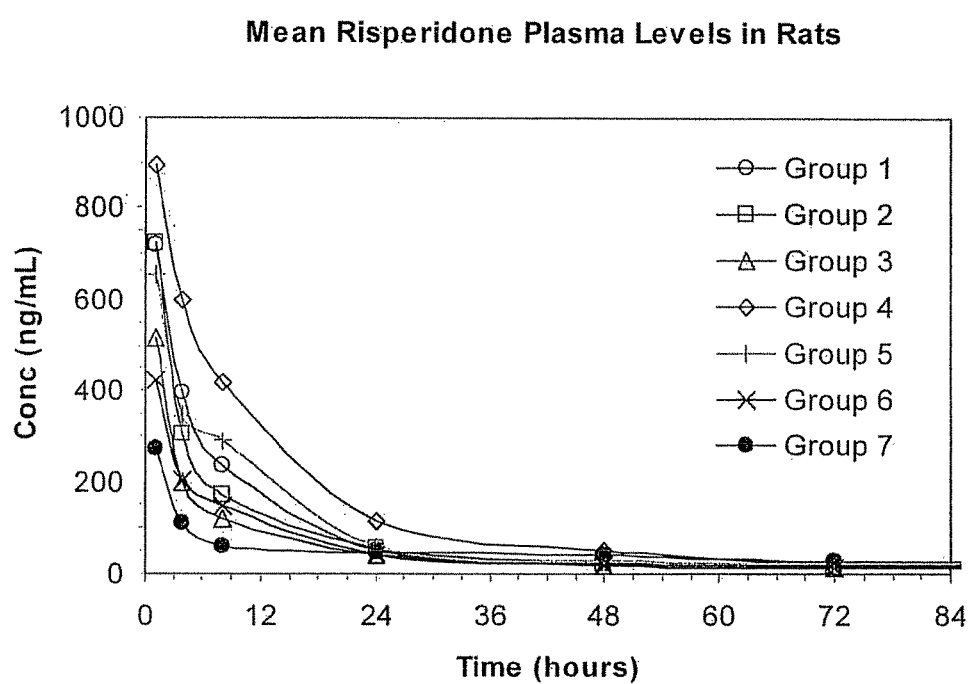
FIG. 18 shows the PK profile of risperidone in rats from compositions comprising risperidone, sucrose acetate isobutyrate, solvent (e.g., benzyl alcohol, ethanol, benzyl benzoate, and N-methyl-pyrrolidone), and polymer (e.g., poly (lactic acid) (PLA) and poly(lactic acid)(glycolic acid) (PLGA)).
Figure 19:
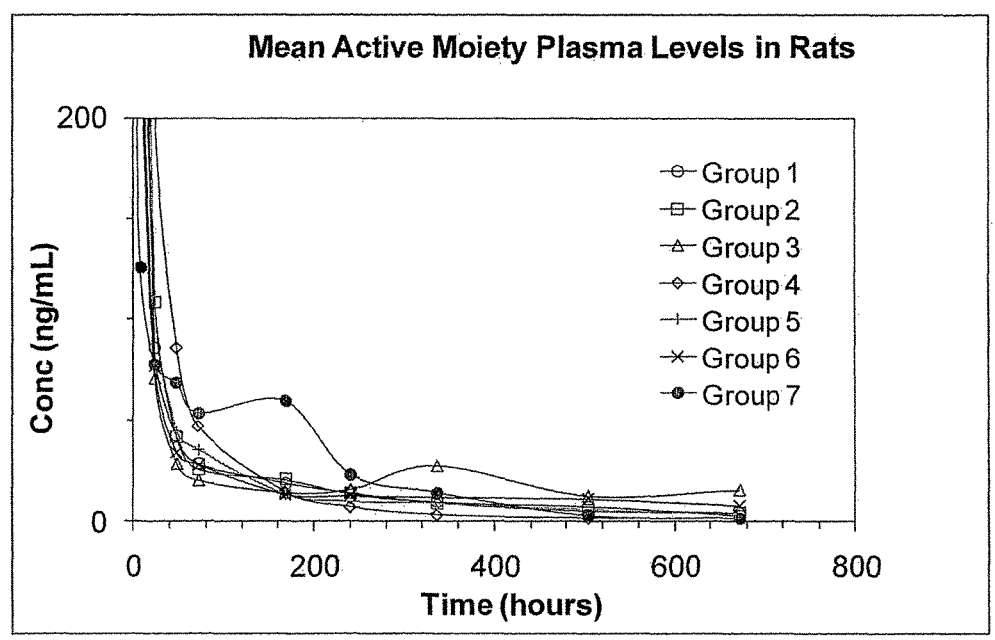
FIG. 19 shows the pharmaceutically active moiety (risperidone+9-hydroxy risperidone) PK profile following subcutaneous (SC) administration of the compositions shown in FIG. 18.
Figure 20:
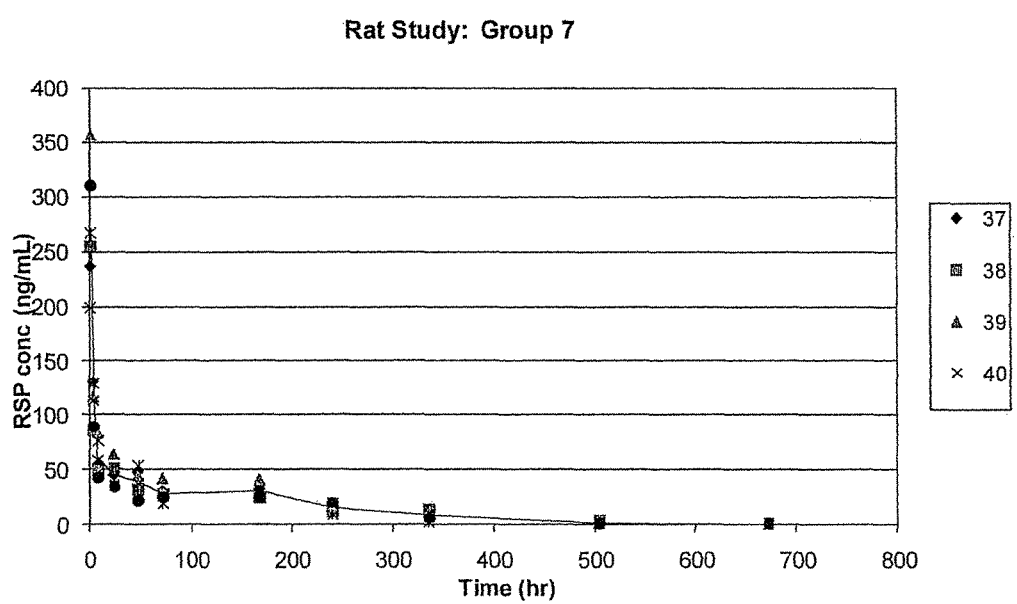
FIG. 20 shows the PK profile of risperidone in individual rats following SC administration of one of the risperidone compositions shown in FIG. 18.

The resulting PK profiles in rats are shown in FIGS. 18 to 20. FIG. 18 shows the mean risperidone PK profiles. FIG. 19 shows the mean pharmaceutically active moiety (risperidone+9-hydroxy risperidone) PK profiles. FIG. 20 shows the risperidone PK profile of individual rats from Group 7.

The results from this study showed relatively large initial release of drug/metabolite into the systemic circulation after subcutaneous (SC) administration of risperidone-solution formulations in rats.

Example 12: Gamma Radiation Stability Study

As discussed in more detail below, this Example was directed to evaluating the gamma radiation stability of formulations with or without risperidone comprising sucrose acetate isobutyrate, N-methyl-pyrrolidone, and hexanediol-initiated poly(lactic acid)(glycolic acid).

Specifically, samples of the below formulations were stored neat at 37° C., with or without being treated with 25 kGy of gamma irradiation.

| Formulation No. | Formulation Composition [wt %] | Initiator | L:G | PLGA Mw (kDa) | Gamma Radiation (kGy) |
|---|---|---|---|---|---|
| NA | SAIB/NMP/PLGA (55/25/20) | HD | 65:35 | 5.1 | None |
| NA | SAIB/NMP/PLGA (55/25/20) | HD | 65:35 | 5.1 | 25 |

-continued

| Formulation No. | Formulation Composition [wt %] | Initiator | L:G | PLGA Mw (kDa) | Gamma Radiation (kGy) |
|---|---|---|---|---|---|
| R7 | 10 wt % RSP in SAIB/NMP/PLGA (55/25/20) | HD | 65:35 | 5.1 | None |
| R7 | 10 wt % RSP in SAIB/NMP/PLGA (55/25/20) | HD | 65:35 | 5.1 | 25 |

Figure 21:
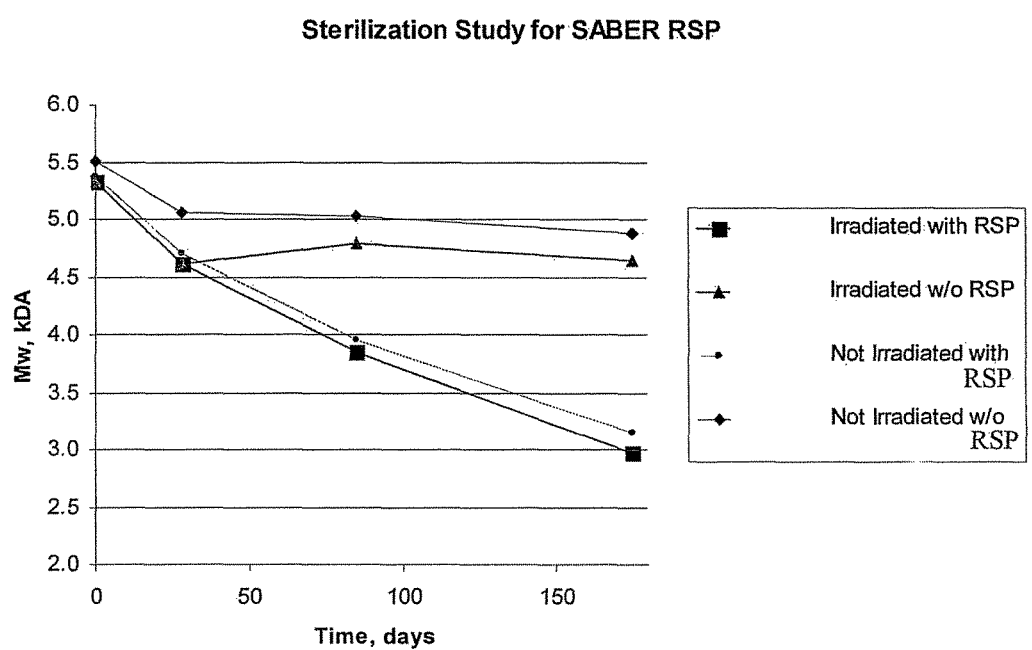
FIG. 21 shows the molecular weight of polymer with respect to storage time in compositions with or without risperidone and with or without gamma radiation treatment.

The molecular weight of the polymer was monitored for degradation. Results are shown in FIG. 21, which shows that the presence or absence of risperidone affected molecular weight more than gamma irradiation.

Example 13: Risperidone In Vivo Release in Rats

As discussed in more detail below, this Example was directed to in vivo release in rats of risperidone from formulations comprising risperidone, sucrose acetate isobutyrate, solvent (N-methyl-pyrrolidone or dimethylsulfoxide), dodecanol-initiated poly(lactic acid)(glycolic acid), and optionally poly(lactic acid).

The risperidone formulations were generally prepared as described above. The risperidone particles were jet milled.

The PK of each of three risperidone-vehicle formulations, shown in the below Table, was evaluated in male Sprague-Dawley rats (N=6/group) following SC administration. The risperidone in each of these formulations was milled. A control group in which risperidone was delivered by IV bolus administration was also included for the purpose of determining SC bioavailability.

| Group | Form. No. | Formulation Composition [wt %] (nominal RSP particle size) (RSP solubility in vehicle) | PLGA or PLA | | | Dose Route | Nominal RSP Dose (mg) | Nominal RSP Dose (mg/kg) | Dose Volume (μL) |
| | | | Initiator | L:G | Mw (kDa) | | | | |
|---|---|---|---|---|---|---|---|---|---|
| 1 | R10 | SAIB/NMP/PLGA/RSP 50/22/18/10 (2-5 μm) (8 mg/mL) | DD | 65:35 | 6.3 | SC | 17 | 49 | 150 |
| 2 | R8 | SAIB/DMSO/PLGA/ RSP 50/22/18/10 (2-5 μm) (6 mg/mL) | DD | 65:35 | 6.3 | SC | 17 | 49 | 150 |
| 3 | R9 | SAIB/DMSO/PLGA/ PLA R202H/RSP 50/22/9/9/10 (2-5 μm) (7 mg/mL) | DD LA | 65:35 100:0 | 6.3 14 | SC | 17 | 49 | 150 |
| 4 | NA | 0.4 mg/mL RSP in citrate buffer | NA | NA | NA | IV bolus | 0.12 | 0.34 | 300 |

Nominal dose based on a 350 g rat
RSP = Risperidone

Blood samples were obtained at several intervals beginning on the day of dosing continuing up to Day 28. The concentration of risperidone and 9-OH risperidone (a major metabolite) in rat plasma samples was determined using an HPLC/MS/MS method.

Figure 22:
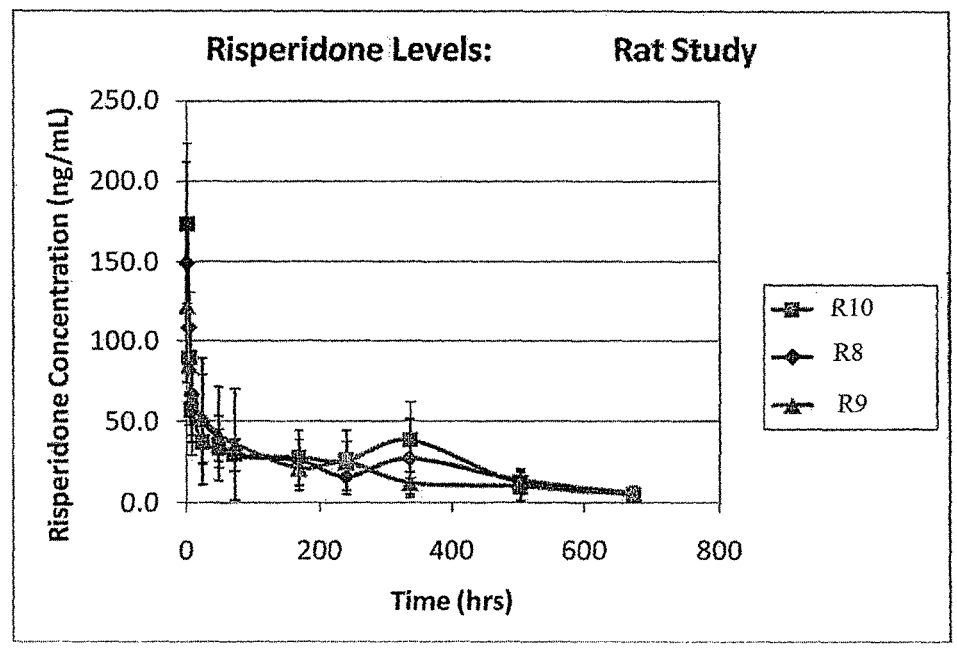
FIG. 22 shows the PK profile of risperidone in rats from compositions comprising risperidone, sucrose acetate isobutyrate, solvent (N-methyl-pyrrolidone or dimethylsulfoxide), dodecanol-initiated poly(lactic acid)(glycolic acid), and optionally poly(lactic acid).
Figure 23:
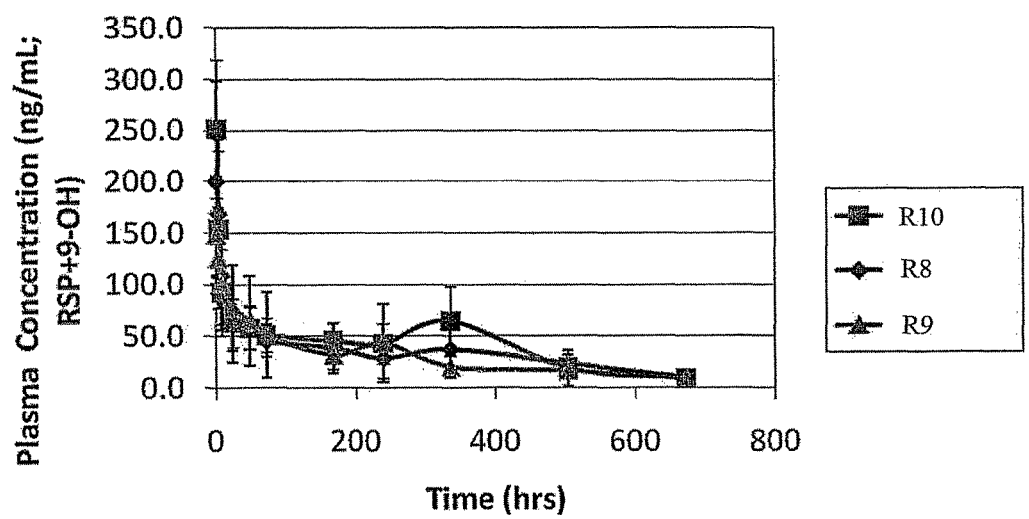
FIG. 23 shows the pharmaceutically active moiety (risperidone+9-hydroxy risperidone) PK profile following SC administration of the compositions shown in FIG. 22.
Figure 24:
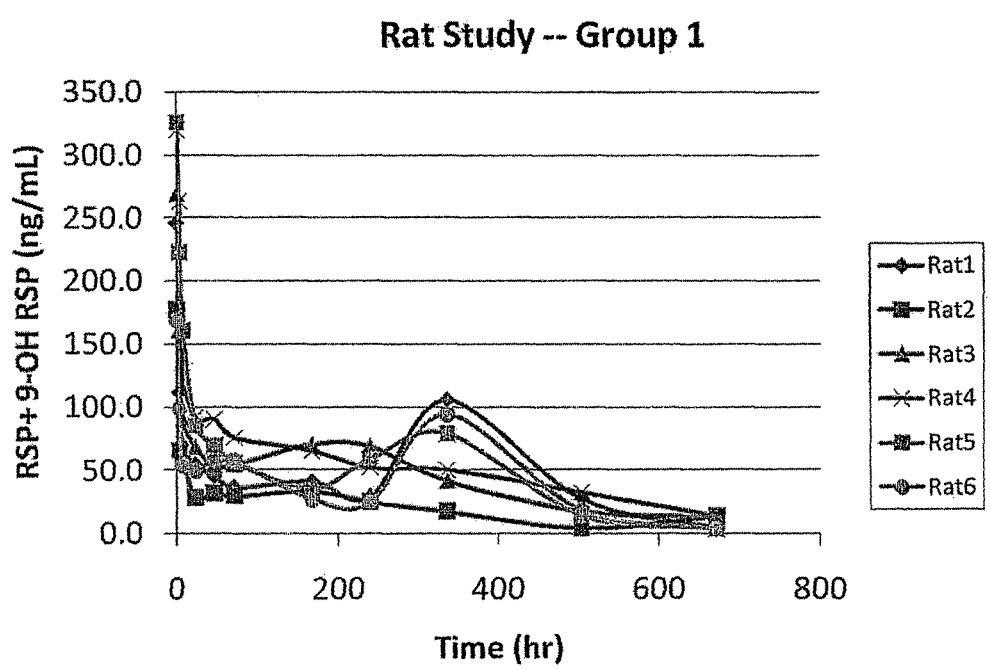
FIG. 24 shows the pharmaceutically active moiety PK profile of individual rats following SC administration of one of the risperidone compositions shown in FIG. 23.

The resulting PK profiles in rats are shown in FIGS. 22 to 24. FIG. 22 shows the risperidone PK profiles. FIG. 23 shows the pharmaceutically active moiety (risperidone+9-hydroxy risperidone) PK profile. The data indicate that a similar kinetic profile exists for both parent drug and its active metabolite. FIG. 24 shows the pharmaceutically active moiety PK profile of individual rats for Group 1.

The PK profile in rats obtained with Formulation No. R10 indicated that risperidone was released into the systemic circulation in a slow and sustained manner over the 28-day post-administration blood sampling period. Plasma levels of risperidone gradually declined following administration and no evidence of dose dumping or large increases in drug levels were observed. Similar profiles were noted with other formulations tested in this study. Peak levels of risperidone and 9-OH risperidone for Formulation No. R10 are compared with those for the IV bolus in the below Table.

| | RSP | | 9-OH RSP | |
|---|---|---|---|---|
| Group | Cmax ng/mL | Tmax | Cmax ng/mL | Tmax |
| 1 (49 mg/kg), SC | 174 ± 50 | 0.04 days | 81 ± 23 | 0.04 days |
| RSP in Citrate Buffer pH 5; (0.34 mg/kg), IV | 512 ± 176 | 0.03 hr | 50 ± 15 | 1.0 hr |

$C_{max}$ data expressed as Mean ± standard deviation;
$T_{max}$ data expressed as Median values
RSP = Risperidone
9-OH RSP = 9-hydroxy risperidone Peak risperidone levels following a risperidone dose of 49 mg/kg were approximately one-third of those following a 0.34 mg/kg IV dose of risperidone.

The below Table summarizes exposure (AUC) and bioavailability data for risperidone, 9-OH risperidone and pharmaceutically active moiety including that associated with initial burst ($AUC_{0-24\ hr}$) and over 28 days following the administration of Formulation No. R10. Exposure over the first 24 hours was ~9.3% of the total AUC and plasma levels were sustained over 21-28 days indicating a lack of dose dumping. The data from this study provided additional information that risperidone-vehicle formulations administered subcutaneously were capable of providing for the sustained release of risperidone without significant bursts of parent drug. The extent of exposure over the initial 24 hours seen in this study provided empirical proof that risperidone-vehicle administered subcutaneously would not result in high levels of risperidone and associated acute toxicity.

| Analyte | $T_{max}$ (days) | $C_{max}$ (ng/mL) | $T_{1/2}$ (days) | $AUC_{0-24\ hr}$ (day-ng/mL) | $AUC_{0-28\ d}$ (day-ng/mL) | $AUC_{0-24\ hr}/AUC_{0-28\ d} \times 100$ (%) |
|---|---|---|---|---|---|---|
| RSP | 0.04 ± 0 | 174 ± 50 | 6.59 ± 4.05 | 64.1 ± 24.9 | 701 ± 189 | 9.3 ± 2.8 |
| 9-OH RSP | 0.08 ± 0.06 | 81 ± 23 | 5.64 ± 3.08 | 38.9 ± 15.9 | 449 ± 129 | 8.6 ± 1.9 |
| AM | 0.04 ± 0 | 251 ± 68 | 6.41 ± 3.71 | 103 ± 40.7 | 1150 ± 305 | 9.0 ± 2.4 |

Figure 25:
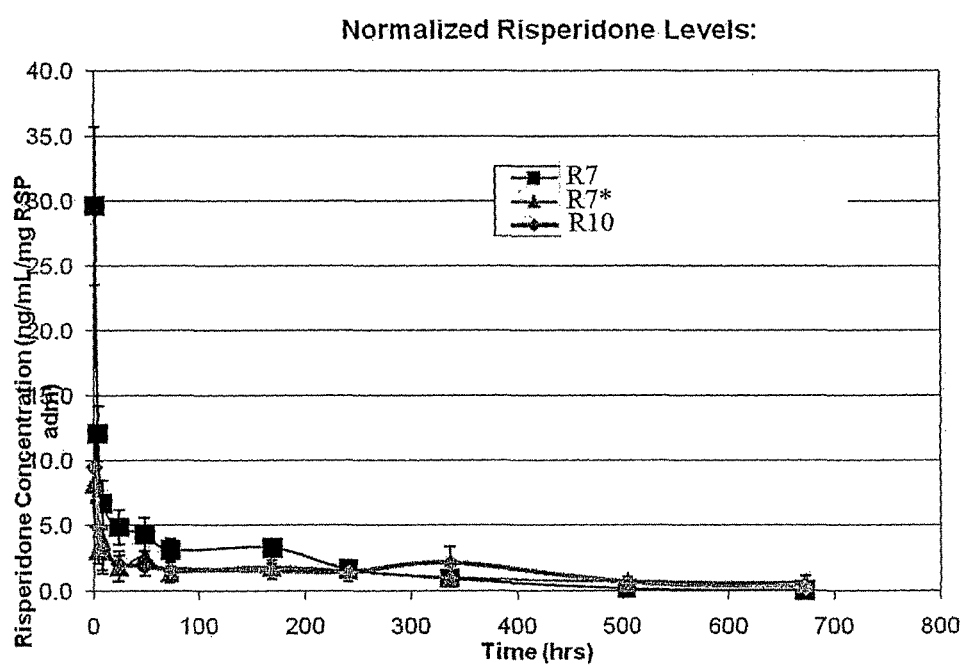
FIG. 25 compares the PK profile of risperidone in rats from three compositions: (1) made with large particle risperidone and a vehicle including hexanediol-initiated poly (lactic acid)(glycolic acid) (PLGA); (2) made with small particle risperidone and a vehicle including hexanediol-initiated PLGA; and (3) made with small particle risperidone and a vehicle including dodecanol-initiated PLGA.
Figure 26:
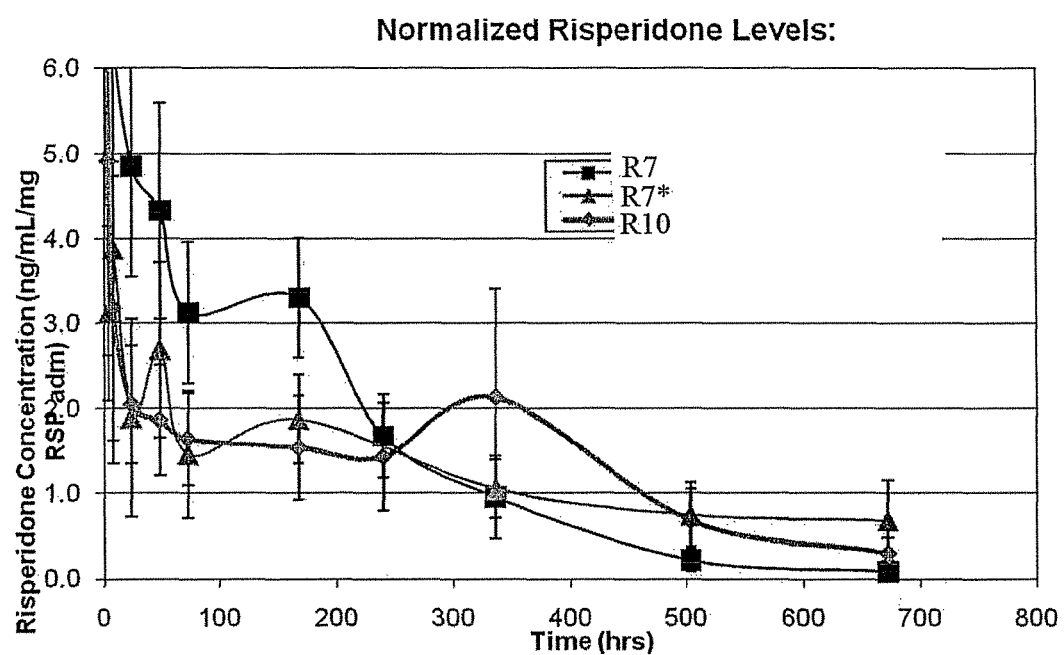
FIG. 26 is an expanded view of a portion of FIG. 25.
Figure 27:
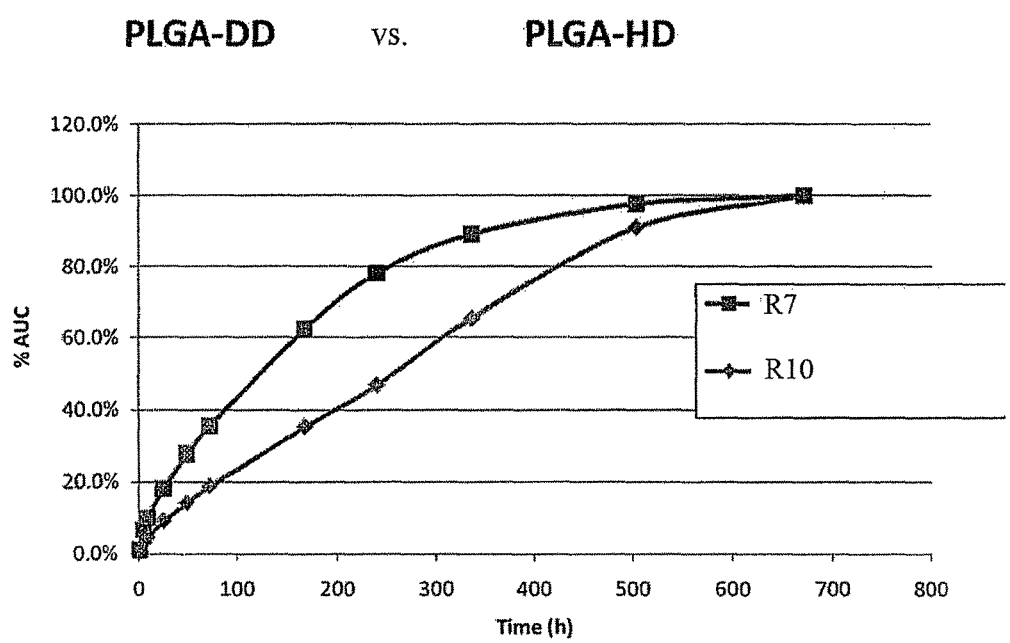
FIG. 27 involves the same experiment as shown in FIGS. 25 and 26, and compares the AUC from compositions: (1) made with small particle risperidone and a vehicle including hexanediol-initiated PLGA; and (2) made with small particle risperidone and a vehicle including dodecanol-initiated PLGA.

Data expressed as Mean ± standard deviation (Median ± % co-efficient of variation values reported for $T_{max}$)
RSP = Risperidone
9-OH RSP = 9-hydroxy risperidone
AM = Active Moiety As shown in FIGS. 25 and 26, Formulation No. R10 (milled drug, dodecanol-initiated PLGA) resulted in significantly less burst than Formulation No. R7 (milled drug, hexanediol-initiated PLGA). Formulation No. R10 appears to have corrected the plasma level drop-off (after 240 hours) observed with Formulation No. R7 with milled drug. FIG. 27 shows that Formulation No. R10 provides a better AUC profile than observed with Formulation No. R7 with milled drug.

In a separate study, Formulation No. R7* (with as received risperidone) was administered to rats. The resulting PK profile of Formulation No. R7* (with unmilled risperidone) was similar to that of Formulation No. R10 through 504 hours (3 wks).

In summary, the results from this study demonstrated that continuous and sustained release of risperidone was achievable with subcutaneous administration of Formulation No. R10 (dodecanol-initiated PLGA) in rats in the absence of an excessive initial release of drug/metabolite into the systemic circulation.

Example 14: Risperidone In Vivo Release in Dogs

As discussed in more detail below, this Example was directed to in vivo release in dogs of risperidone from formulations comprising risperidone, sucrose acetate isobutyrate, solvent, and dodecanol-initiated poly(lactic acid) (glycolic acid) (L:G=75:25).

This single dose PK study in beagle dogs evaluated four risperidone-vehicle formulations, shown in the below Table.

The four formulations were each administered once to separate groups of five male beagle dogs (animals 3-5.5 years of age and weighing 8.4-11.4 kg at study initiation) subcutaneously (in the midscapular area) at a nominal dose and dose volume of 52-53 mg and 0.5 mL, respectively. Another group of five males was dosed IV with risperidone (0.6 mg total dose at a dose volume of 5 mL). The formulations which were tested (and their components) and the study design are provided in the below Table.

Each of the formulations was irradiated at 15 kGy. The formulations were stable on irradiation and on storage. The formulations had greater than 99% risperidone purity after 6 months storage at 5 C. For Formulation No. R66, PLGA molecular weight after 6 months storage at 5 C was greater than 90% of initial molecular weight.

Blood was collected and analyzed for risperidone and 9-OH risperidone levels in plasma, up to and including 42 days after treatment. Clinical signs were recorded daily and body weights recorded weekly starting with the day of dosing (Day 0).

All animals in Groups 3 and 4 and the majority of animals in Groups 1, 2 and 5 exhibited clinical signs consistent with the pharmacological properties of risperidone on the day of dosing. The dosage administered to the dogs was approximately 7-fold greater on a body weight basis than the human dose used in the Phase 1 trial described in Example 15, below. These observations included hypoactivity, tremors that affected the front legs and/or the whole body and hyperactivity, manifested by chewing the hardware in the cage. Aside from one Group 3 and one Group 5 animal that exhibited similar clinical signs on Day 2, no other test article-related clinical signs were observed. No differences in body weight were seen amongst the different groups. Mean body weights declined slightly in all groups the first week of the study but remained stable or increased back toward baseline levels thereafter.

Figure 28:
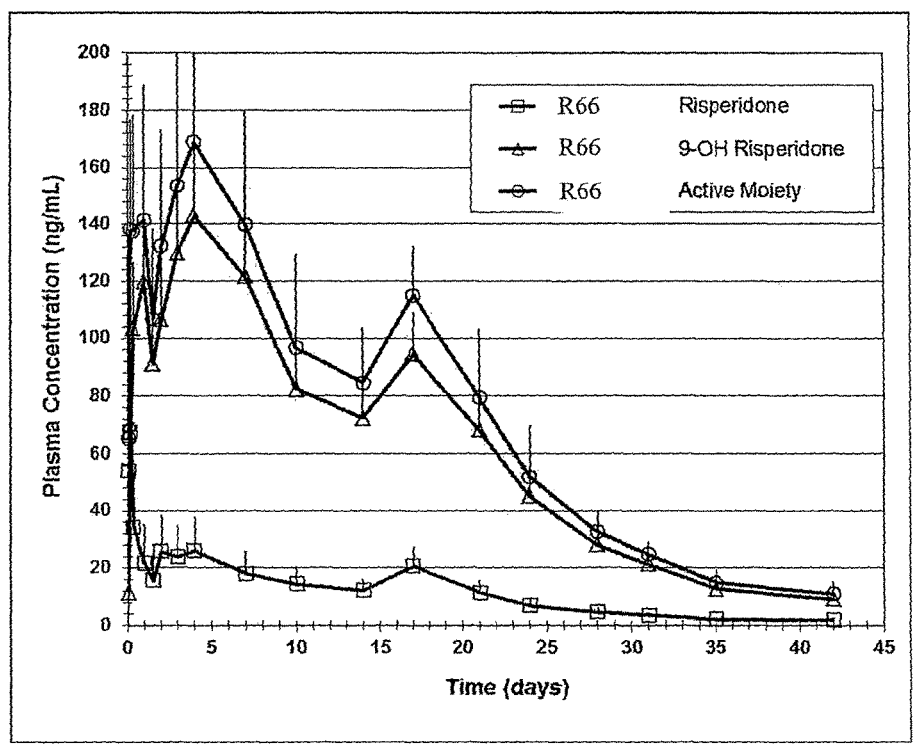
FIG. 28 shows pharmacokinetic profiles in dogs following SC administration of a 9 wt % risperidone composition.

Based on AUC values, the overall exposure of dogs to risperidone and 9-OH risperidone during the 42-day sample collection period appeared to be similar for animals given the different risperidone-vehicle formulations. Risperidone exhibited good bioavailability following SC administration to dogs with Formulation No. R66. The PK profile following the SC administration of Formulation No. R66 was characterized by the slow and sustained release of drug into plasma with levels declining over time and therapeutically active levels being maintained for 4 weeks (FIG. 28). Mean levels of risperidone and pharmaceutically active moiety did not exceed 181 ng/mL and 350 ng/mL (average $C_{max}$ for risperidone and pharmaceutically active moiety following 2 mg oral Risperdal administration) respectively, for Formulation No. R66 indicating drug burst/dumping did not occur.

Figure 29:
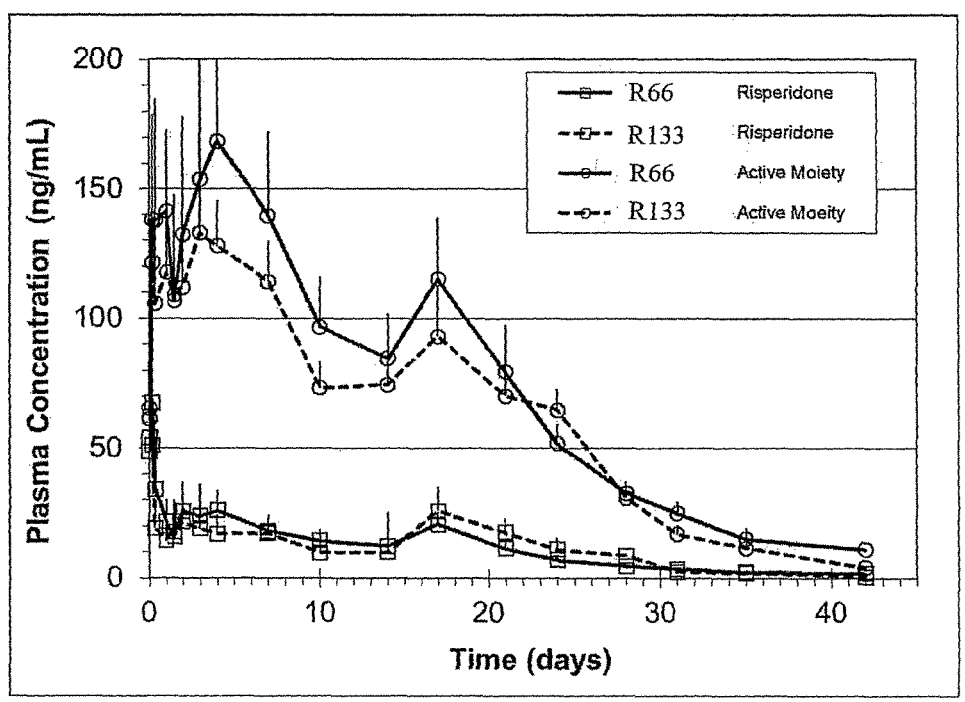
FIG. 29 shows the effect of particle size on PK profile in dogs.

A comparison of Group 2 (Formulation No. R66, 0.5-2 μm) and Group 5 (Formulation No. R133, 2-5 μm) demonstrated that for formulations with the same viscosity, but different particle size (i.e., 0.5-2 μm vs. 2-5 μm for Groups 2 and 5, respectively), and slightly different composition, the risperidone PK profile was nearly identical (FIG. 29).

A summary of the PK parameters obtained with Formulation No. R66 is provided in the below Table.

| Group | Form. No. | Formulation Composition SAIB/NMP/PC/PLGA/RSP [wt %] (nominal RSP particle size) | PLGA Initiator | L:G | Mw (kDa) | Dose Route | Nominal RSP Dose (mg) | Nominal RSP Dose (mg/kg) | Dose Volume (mL) |
|---|---|---|---|---|---|---|---|---|---|
| 1 | NA | 0.12 mg/mL RSP in citrate buffer | NA | NA | NA | IV bolus | 0.6 | 0.06 | 5 |
| 2 | R66 | 46/27/0/18/9 (0.5-2 μm) | DD | 75:25 | 7.0 | SC | 53 | 5.3 | 0.5 |
| 3 | R131 | 40/0/34/17/9 (0.5-2 μm) | DD | 75:25 | 7.0 | SC | 52 | 5.2 | 0.5 |
| 4 | R126 | 42/9/22/18/9 (0.5-2 μm) | DD | 75:25 | 7.0 | SC | 52 | 5.2 | 0.5 |
| 5 | R133 | 50/25/0/16/9 (2-5 μm) | DD | 75:25 | 7.0 | SC | 52 | 5.2 | 0.5 |

Nominal dose based on a 10 kg dog
Study report describes composition of vehicle into which, specified wt % of risperidone is dispersed.
RSP = risperidone
PC = propylene carbonate

| Analyte | $T_{max}$ (days) | $C_{max}$ (ng/mL) | $T_{1/2}$ (days) | $AUC_{0-24\,hr}$ (day-ng/mL) | $AUC_{0-28\,d}$ (day-ng/mL) | $AUC_{0-24\,hr}/AUC_{0-28\,d} \times 100$ (%) | $F_{last}$ (%) |
|---|---|---|---|---|---|---|---|
| RSP | 0.142 ± 0.056 | 73.0 ± 54.5 | 7.2 ± 2.7 | 35.1 ± 34.9 | 431 ± 342 | 7.4 ± 1.8 | 114 |
| 9-OH RSP | 8.6 ± 7.1 | 158 ± 79.0 | 12.3 ± 9.5 | 94.1 ± 45.5 | 2329 ± 1023 | 4.0 ± 0.3 | NC |
| AM | 10.6 ± 7.9 | 187 ± 97.2 | 10.2 ± 7.7 | 130 ± 78.6 | 2763 ± 1323 | 4.5 ± 0.6 | 97 |

Data expressed as Mean ± standard deviation
Bioavailability vs. IV bolus
RSP = Risperidone
9-OH RSP = 9-hydroxy risperidone
AM = Active Moiety = RSP + 9-OH RSP
NC = Not Calculated In summary, the results of this study indicated that Formulation No. R66 exhibited a PK profile consistent with a low initial burst and no dose dumping and prolonged, continuous, and sustained release into plasma.

Example 15: A Pilot, Open-Label, Non-Randomized, Single Ascending Dose, Safety and Pharmacokinetic Phase I Clinical Trial with Injectable Risperidone-Vehicle and the DosePro® Delivery System in Patients with Chronic, Stable Schizophrenia or Schizoaffective Disorder The primary objectives of this study were:

To assess the pharmacokinetic (PK) profile of a risperidone-vehicle formulation administered as a single subcutaneous (SC) injection via needle and syringe or via the DosePro® needle-free Delivery System administered at an equivalent dose.

To evaluate the safety and tolerability of a risperidone-vehicle formulation administered as a single SC injection or via the DosePro® needle-free delivery system administered to the abdominal region.

This was an open-label, single ascending dose (SAD), safety and PK study in patients with chronic, stable schizophrenia or schizoaffective disorder. Forty patients (male and female) with schizophrenia or schizoaffective disorder on antipsychotic maintenance medication were enrolled into three cohorts (10 patients per cohort).

On study day −3, subjects received a single oral dose of 2 mg and plasma PK samples were collected prior to dosing and at 0.333, 0.667, 1, 1.5, 2, 2.5, 3, 4, 6, 8, 12, 24, 48 and 72 hours post-dose.

On study day 1, subjects were randomized to receive a single SC dose of either 25, 50 or 100 mg or 50 mg via a needle-free delivery system, and plasma PK samples were collected prior to dosing and at 0.333, 0.667, 1, 2, 4, 8, 12, 16, 24, 30, 36, 42, 48, 60, 72, 84, 96, 108, 120, 132, 144, 192, 240, 312, 384, 480, 552, 648, 720 and 816 hours post-dose.

The drug product was supplied in 2 mL glass vials, containing a minimum of 1.0 mL of risperidone-vehicle formulation. Each 1.0 mL drug product comprised 100 mg of risperidone formulated with vehicle. The risperidone-vehicle formulation (Formulation No. R137) was comprised of the 8.9 wt % of risperidone formulated with inactive ingredients SAIB, NMP, and PLGA-DD (L:G=75:25; Mw=7.0 kDa) at a weight ratio of 50/30/20. The storage condition for the risperidone-vehicle formulation was −20° C., and the formulation was administered at room temperature.

Patients were administered study drug as follows:

Cohort A—25 mg of risperidone-vehicle formulation was administered as a SC injection of 0.25 mL (100 mg/mL concentration) in the abdominal region.

Cohort B—50 mg of Risperidone-vehicle formulation was administered as 0.5 mL (100 mg/mL concentration) via the DosePro® needle-free delivery system in the abdominal region.

Cohort C—50 mg of risperidone-vehicle formulation was administered as a SC injection of 0.5 mL (100 mg/mL concentration) in the abdominal region.

Cohort D—100 mg of risperidone-vehicle formulation was administered as a SC injection of 1.0 mL (100 mg/mL concentration) in the abdominal region.

Figure 31:
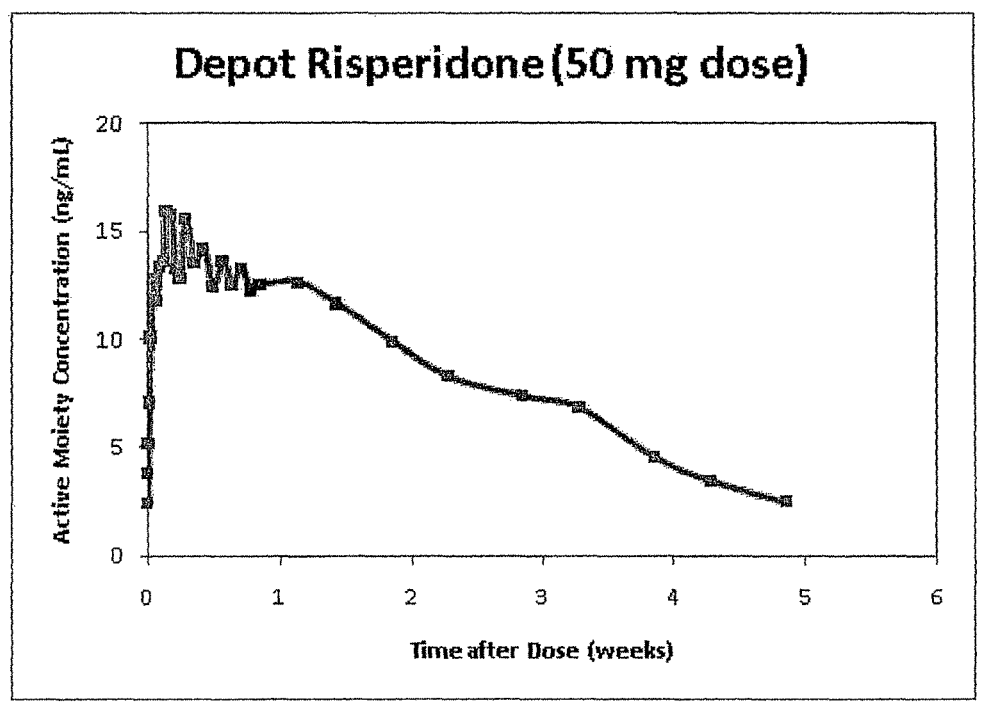
FIG. 31 shows the PK profile when 50 mg of risperidone in the SAIB based vehicle was administered via a DosePro® needle-free injector of 0.5 mL (100 mg/mL concentration) in the abdominal region of humans.

Single dose PK parameters for risperidone, 9-OH risperidone, and pharmaceutically active moiety were analyzed from the concentration time data. The results from Cohorts A, C, and D are shown in FIG. 30. The results from Cohort B are shown in FIG. 31. Extended risperidone delivery was observed for periods greater than 4 weeks. These data show that loading doses are not required.

Example 16: Pharmacokinetic Simulations Based on Phase I Clinical Trial Data and Comparison with Risperdal Consta and Invega Sustenna The clinical trial data of Cohorts A, C, and D from above Example 15 was analyzed with the following goals:

To develop a population PK model for risperidone after administration of oral and SC formulations to healthy subjects of Cohorts A, C, and D;

To conduct model-based simulations to assess the steady-state risperidone and 9-OH-risperidone concentrations achieved after various SC dosing regimens; and To compare steady-state profiles with mean steady-state profiles for Risperdal Consta and Invega Sustenna obtained from the literature.

Population PK analysis was performed using the first-order conditional estimation method with η-ε interaction as implemented in NONMEM® Version 7.1.2.

Interindividual variability ($\omega^2$) for each parameter was estimated using an exponential error model; in some cases a logistical transform was instead used to constrain values between 0 and 1.

A proportional error model was used to characterize residual error ($\sigma^2$) separately for risperidone and 9-OH-risperidone.

Candidate population PK models were assessed by:

Evaluation of individual and population mean PK parameter estimates and their precision measured by the % standard error of the mean (% SEM);

Graphical examination of diagnostic goodness-of-fit plots;

Graphical examination of the agreement between the observed and individual post-hoc predicted concentration-time data;

Reduction in both $\sigma^2$ and $\omega^2$; and

Comparison of minimum objective function values (MVOF) for nested models.

Stage 1: Oral Data only

Based upon inspection of individual PK profiles, a 2-compartment (2-CMT) model with first-order absorption plus and first-order elimination was initially evaluated to characterize both the plasma risperidone and 9-OH-risperidone PK data and was parameterized using:

A Fraction of dose which escapes first-pass metabolism and is systemically available as parent ($F_n$) or metabolite ($1-F_n$)

First-order rate-constant ($k_{a,PO}$) and lag time ($T_{lag}$) for the appearance of either parent or metabolite in the plasma Total parent clearance (CL), the systemically available fraction of parent which is converted to metabolite ($F_m$; $CL_{pm}=CL \cdot F_m$), and the metabolite clearance ($CL_m$)

Central volume of distribution for parent (Vc) and metabolite ($Vc_m$)

Distribution clearance between the central and peripheral CMT for parent (CLd) and metabolite ($CLd_m$)

Peripheral volume of distribution for parent (Vp) and metabolite ($Vp_m$)

Stage 2: Oral and Subcutaneous Data

Bi- and tri-phasic absorption models were implemented to allow for an initial plus two very slow release phases of only the parent risperidone into the systemic circulation (once there, the distribution and metabolism was assumed to be the same as from an oral dose) estimating these additional parameters:

Fraction of SC dose which rapidly goes into the systemic circulation starting at time 0 (FRC) at the first-order rate constant $k_{a,SC1}$ A fraction of the remainder of the SC dose [FRC2·(1−FRC)] which slowly enters the systemic circulation after a prolonged delay ($T_{lag4}$) at the SC depot site at the first-order rate constant $k_{a,SC2}$ The remainder of the SC dose [1−FRC2·(1−FRC)−FRC] which slowly enters the systemic circulation after a prolonged delay ($T_{lag9}$) at the SC depot site at the first-order rate constant $k_{a,SC3}$ Relative bioavailability of the SC relative to PO dose ($F_{sc}$)

Figure 34:
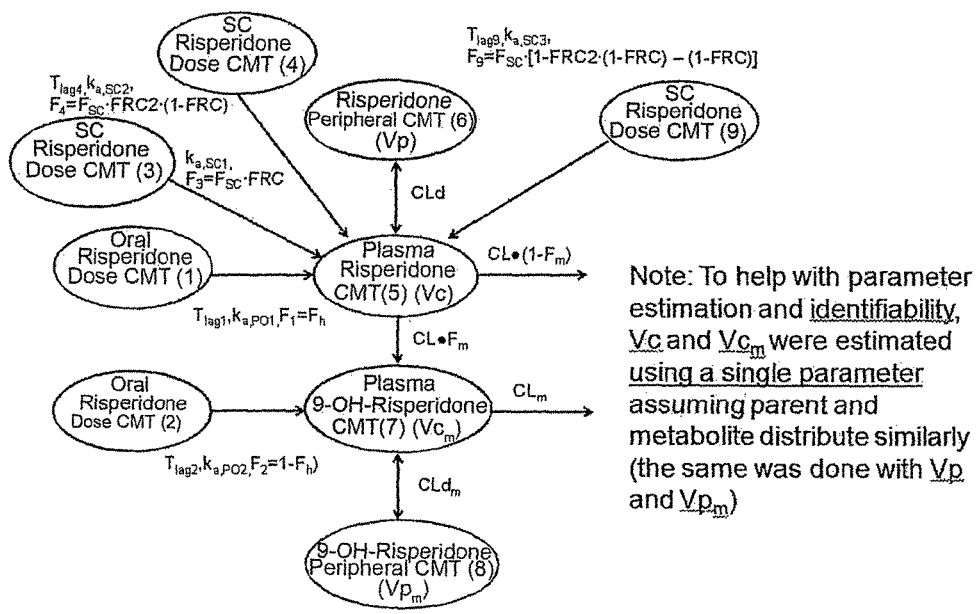
FIG. 34 shows a structural population PK model for PO and SC data.

There is assumed to be no first-pass effect for risperidone for SC dosing. The resulting base structural model for per oral (PO) dosing only is shown in FIG. 32. The resulting base structural model for PO and SC dosing is shown in FIG. 33. The resulting structural population PK model for PO and SC data is shown in FIG. 34.

Monte Carlo Simulations:

Using the final population PK model, MCS was performed to generate risperidone and 9-OH-risperidone concentrations up to 28 days post dose after a single-dose and at steady-state (after 4 monthly doses).

The $5^{th}$, $50^{th}$ and $95^{th}$ percentiles of the active moiety concentrations (sum of risperidone and 9-OH-risperidone concentrations) at steady-state were calculated and plotted by dose group.

Summary statistics of active moiety exposure measures at steady-state (Cmax, Cmin, AUC, etc.) were also calculated and presented tabularly by dose group.

Steady-state active moiety concentration-time data for Risperdal Consta and Invega Sustenna were digitized from the literature and overlaid upon the simulated PK data of the present invention after a single-dose (for comparison to Sustenna only) and at steady-state (for comparison to both Consta and Sustenna).

Note that the digitization process is not without error and is meant solely to be used as a visual guide to compare to the regimens of the present invention simulated using the population PK model.

Figure 35:
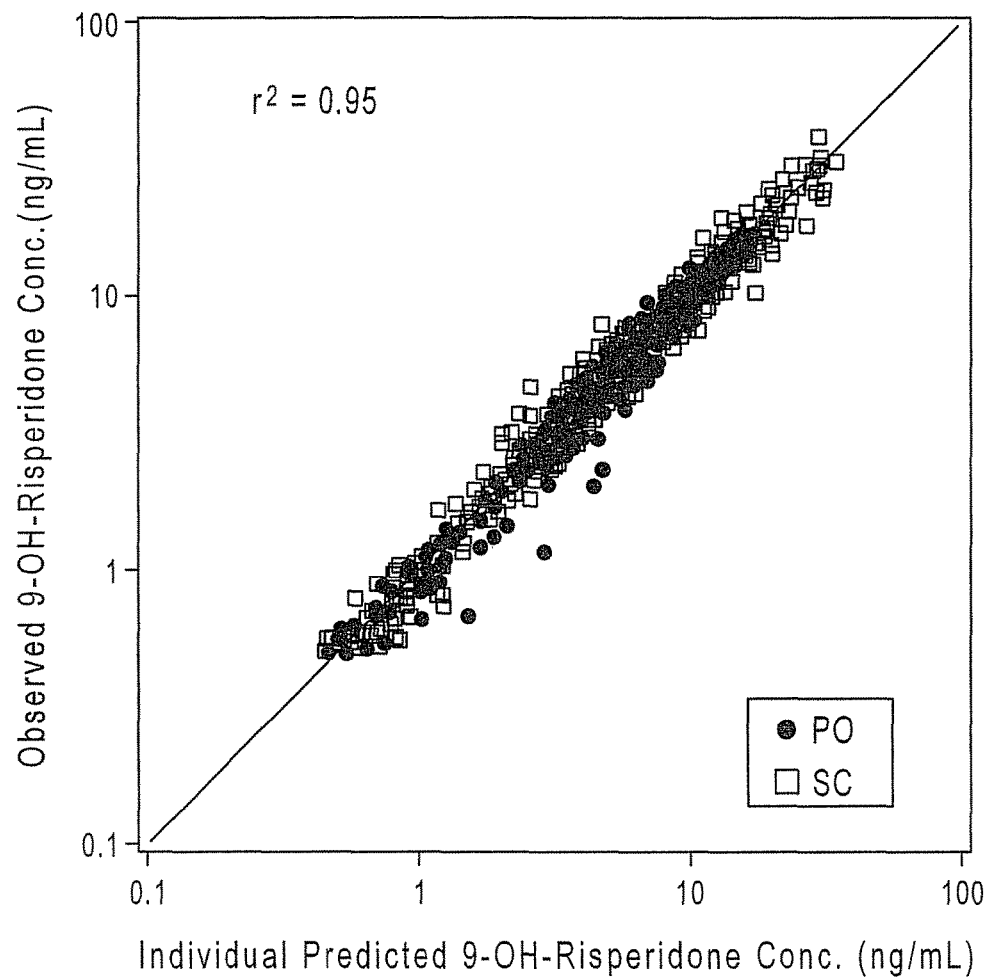
FIG. 35 shows the predictive value of the PK model.

FIG. 35 shows the predictive value of the model.

Figure 36:
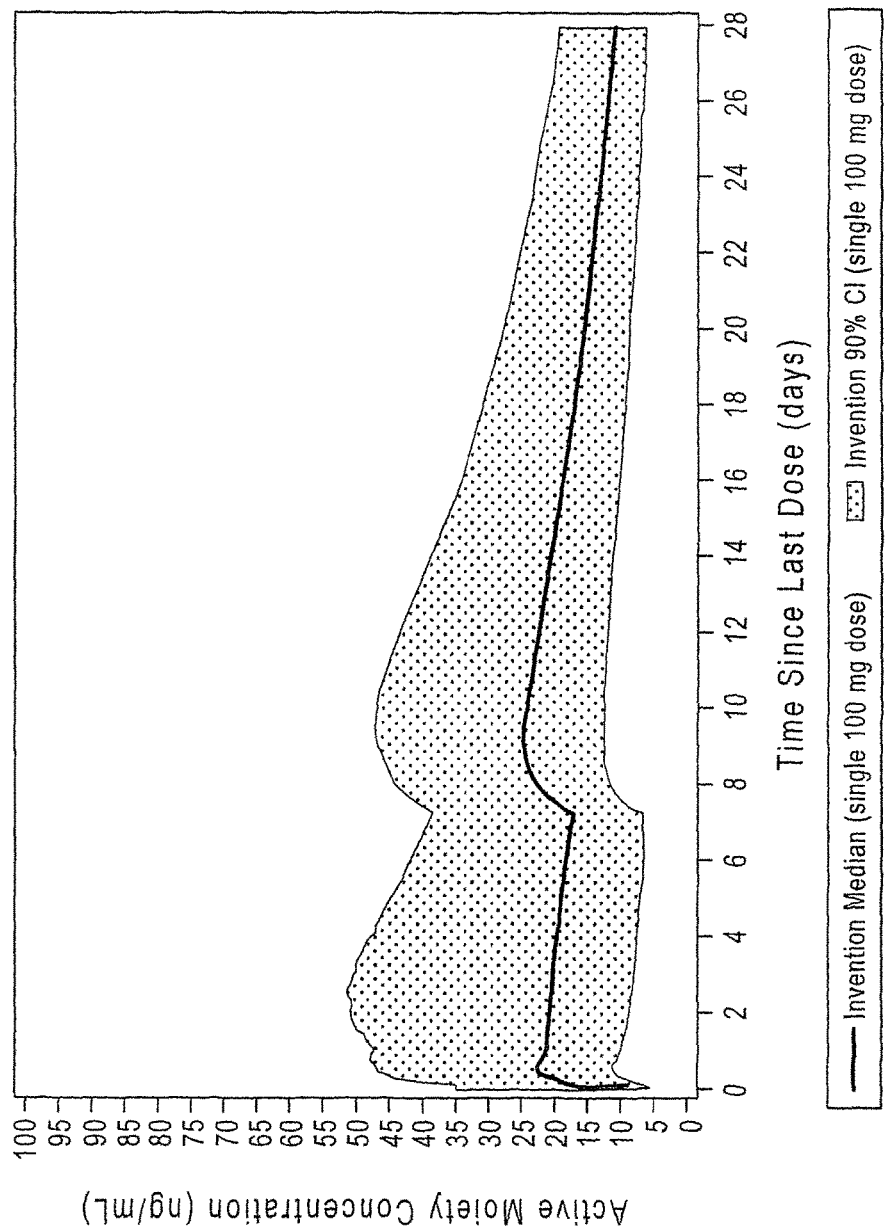
FIG. 36 shows the PK model prediction for a single 100 mg dose of the present invention.
Figure 37A:
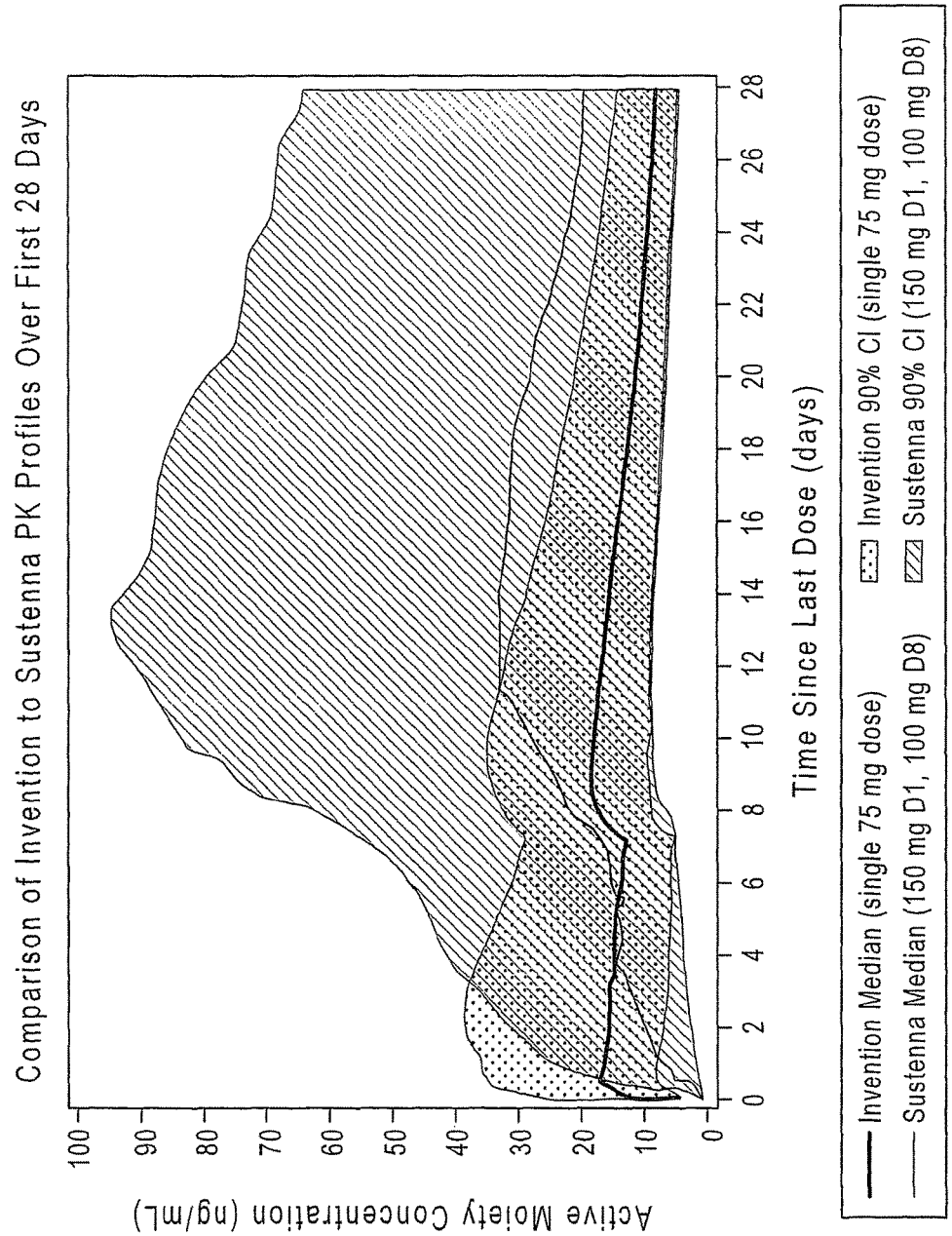
FIGS. 37a and b show the PK model predictions for a single dose of 75 mg and 100 mg, respectively, of the present invention in comparison with paliperidone palmitate (Invega Sustenna).
Figure 37B:
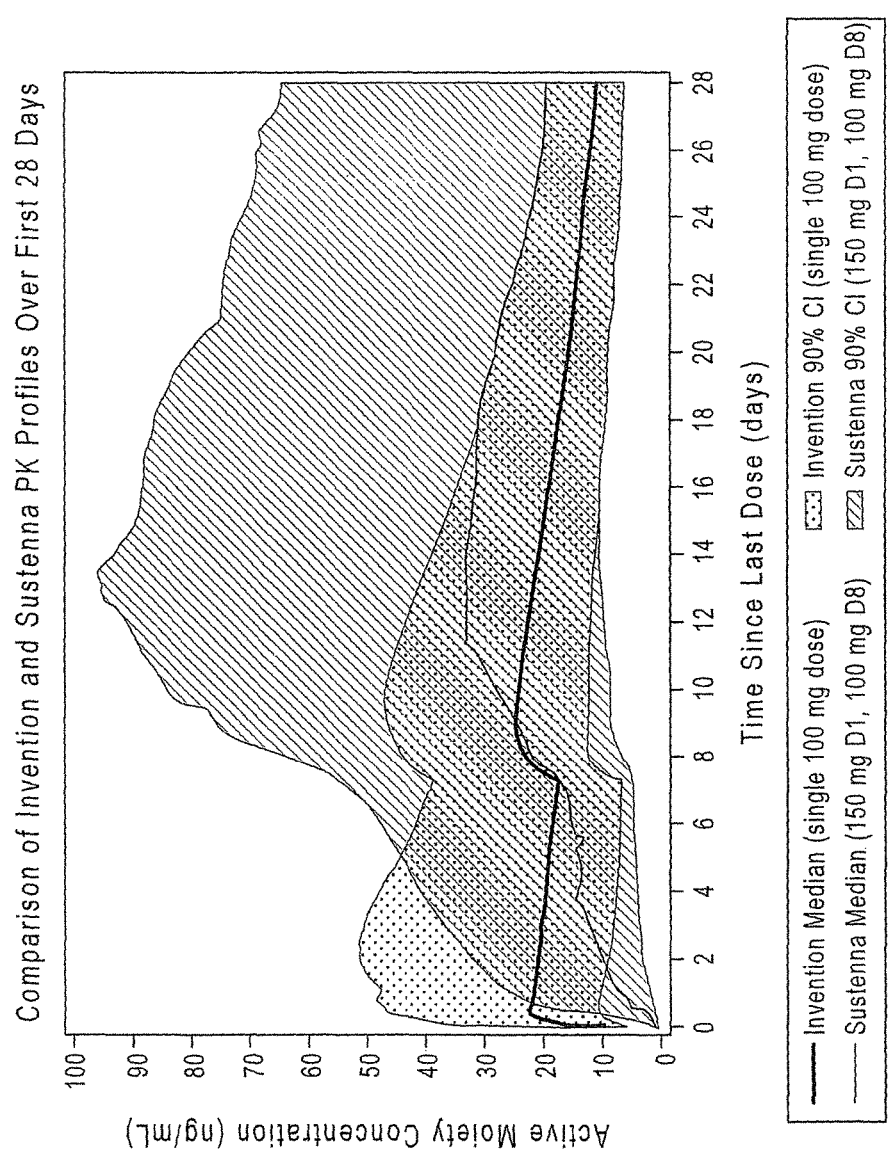

FIG. 36 shows the PK model prediction for a single 100 mg dose of the present invention. FIG. 37 shows the PK model predictions for a single dose of 75 mg and 100 mg, respectively, of the present invention in comparison with paliperidone palmitate (Invega Sustenna).

Figure 38:
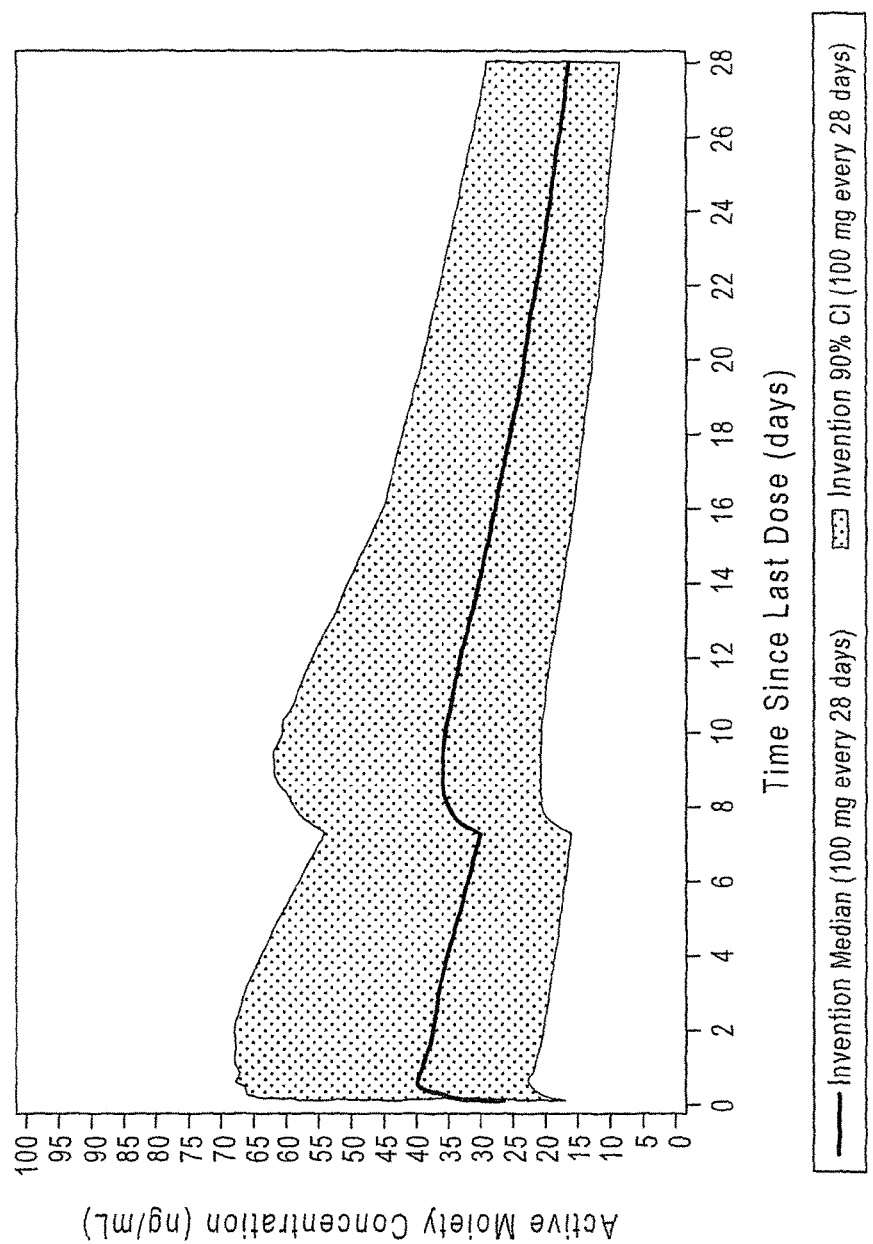
FIG. 38 shows the PK model prediction for steady state (after several doses) plasma levels, for 100 mg dosed every 28 days, of the present invention.
Figure 39:
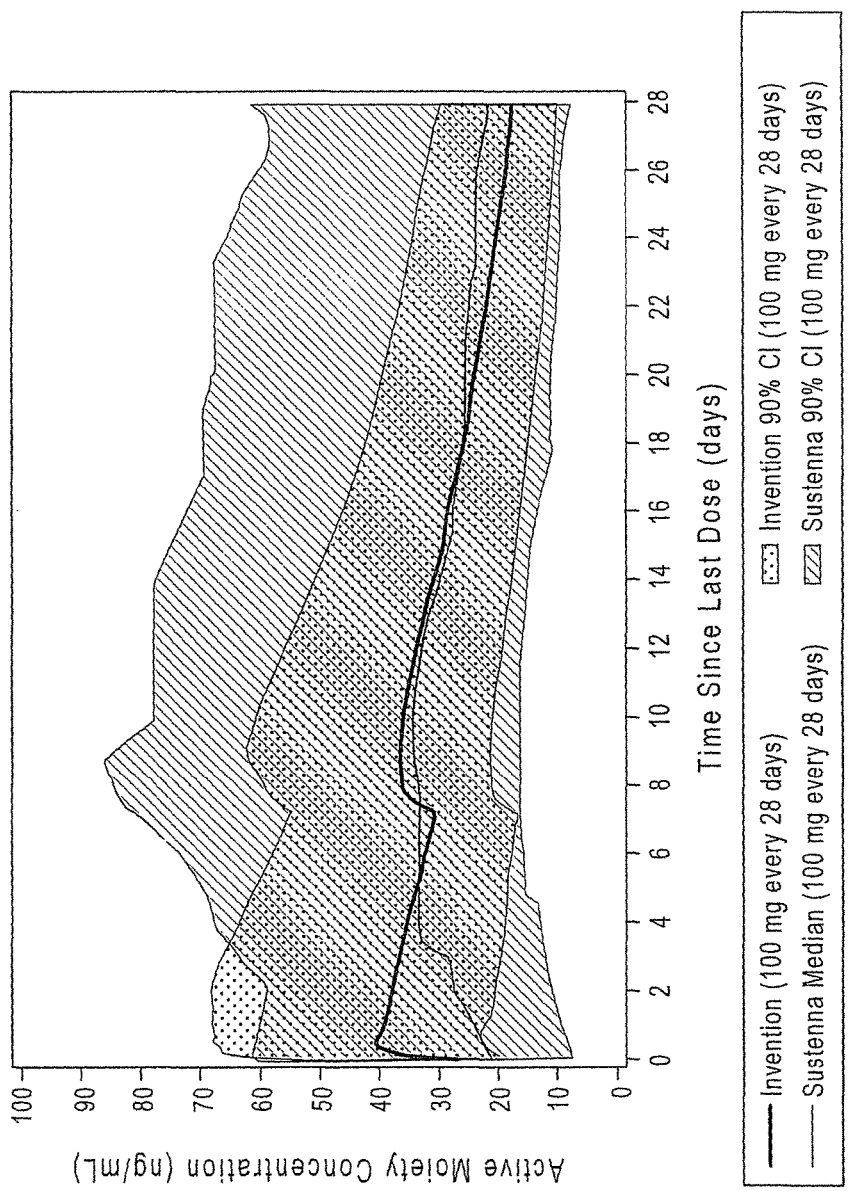
FIG. 39 shows the PK model predictions for steady state (after several doses) plasma levels for 100 mg dosed every 28 days, of the present invention in comparison with paliperidone palmitate (Invega Sustenna).

FIG. 38 shows the PK model prediction for steady state (after several doses) plasma levels, for 100 mg dosed every 28 days, of the present invention. FIG. 39 shows the PK model predictions for steady state (after several doses) plasma levels for 100 mg dosed every 28 days, of the present invention in comparison with paliperidone palmitate (Invega Sustenna).

Example 17: Risperidone In Vivo Release in Dogs Involving Varying Risperidone Concentration and Varying L:G Ratio As discussed in more detail below, this Example was directed to in vivo release in dogs of risperidone from formulations comprising different concentrations of risperidone, sucrose acetate isobutyrate, N-methylpyrrolidone, and dodecanol-initiated poly(lactic acid)(glycolic acid)s having different L:G ratios.

This single dose PK study in beagle dogs evaluated three risperidone-vehicle formulations. The three formulations were each administered once to separate groups of five male beagle dogs (approximately 2-4 years of age and weighing 9.5-11.7 kg at study initiation) subcutaneously (in the mid-scapular area). The formulations which were tested (and their components) and the study design are provided in the below Table.

| Group | Formulation Composition SAIB/NMP/PLGA/RSP [wt %] | PLGA Initiator | PLGA L:G | PLGA Mw (kDa) | Dosage Level (mg/kg)* | Dose Volume (mL/kg) | Dose Route |
|---|---|---|---|---|---|---|---|
| 1 | 45.5/27.3/18.2/9.0 | DD | 75:25 | 7 | 5.4 | 0.05 | SC |
| 2 | 38.0/28.0/16.5/17.5 | DD | 75:25 | 7 | 10.2 | 0.05 | SC |
| 3 | 39.6/26.4/16.5/17.5 | DD | 90:10 | 6.6 | 10.2 | 0.05 | SC |

*Assumed a 10 kg dog weight.

Each of the formulations was irradiated at 15 kGy. The formulations were stable on irradiation.

Blood was collected and analyzed for risperidone and 9-OH risperidone levels in plasma, up to and including 42 days after treatment. Clinical signs were recorded daily and body weights recorded weekly starting with the day of dosing (Day 0). Body weight change was unremarkable over the course of this study.

Based on the results of this study, a single IV dose of Risperidone dose of 0.6 mg or ~0.06 mg/kg and 3 SABER-Risperidone formulations administered individually as single subcutaneous injection in non-naïve male beagle dogs were generally well-tolerated over the course of the study (49 days).

Observations of hypoactivity and a mild to moderate tremors were noted post-dose and through 48 hours of dose administration. Palpable masses developed on the dorsal thoracic area (injection site) occurring at 7-10 days post dose administration in Groups 2-4 (subcutaneous injection) and resolving by Day 35. The dosage administered to the dogs was approximately 7-fold greater on a body weight basis than the human dose used in the Phase I trial described in Example 15, above.

Figure 40:
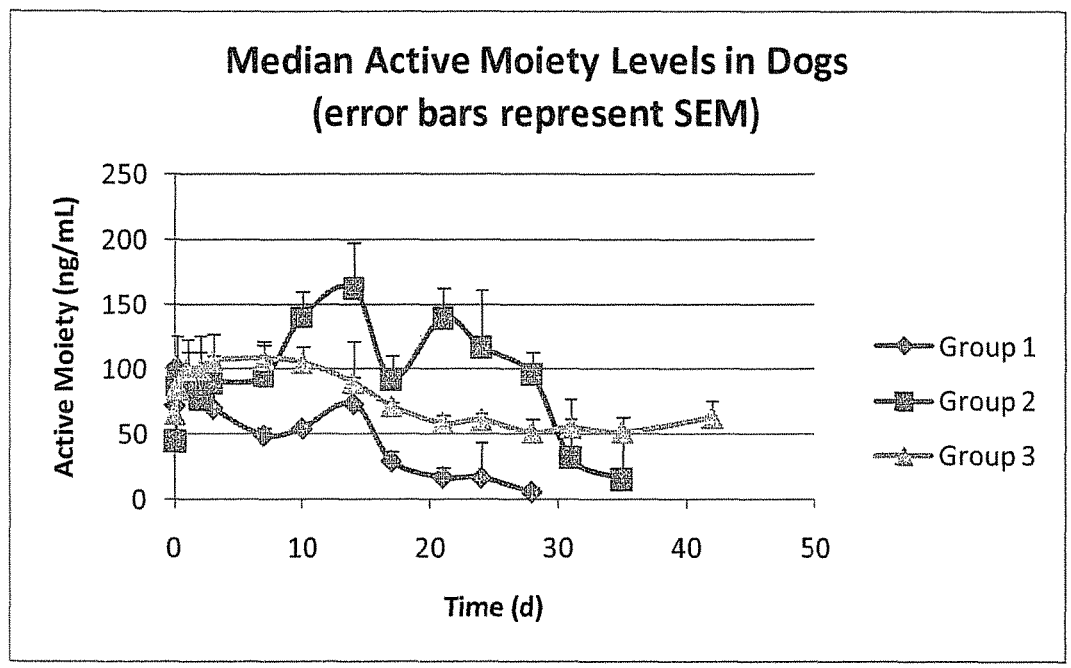
FIG. 40 shows the effect of risperidone concentration and L:G ratio on PK profile in dogs.

The PK profiles following SC administration are shown in FIG. 40. Comparing the profiles of Groups 1 and 2 shows that increasing the risperidone concentration from 9 wt % to 17.5 wt % increased the release rate. Comparing the profiles of Groups 2 and 3 shows that increasing the L:G ratio from 75:25 to 90:10 extended the release duration.

In summary, the results of this study indicated that each of the formulations resulted in a PK profile consistent with a low initial burst and no dose dumping and prolonged, continuous, and sustained release into plasma.

Example 18: Aripiprazole In Vitro Release from Formulations Comprising Polymer and Various Solvents As discussed in more detail below, this Example was directed to comparing the aripiprazole in vitro release behavior of a formulation comprising aripiprazole, sucrose acetate isobutyrate, various solvents (N-methylpyrrolidone and propylene carbonate), and poly(lactic acid)(glycolic acid) initiated with dodecanol (DD).

Two different vehicles were prepared: SAIB/PC/PLGA (44/37/17) and SAIB/NMP/PLGA (50/30/20). The PLGA was PLGA-DD (L:G=75:25; Mw=7 kDa). The vehicles were prepared by weighing each excipient by weight % and were sonicated until a clear solution was achieved.

Aripiprazole was added to the vehicle followed by homogenization. In particular, aripiprazole as received was weighed into 5 mL glass vials at a loading of 200 mg/mL. One (1) mL of the respective vehicles was weighed in from respective glass jars. After 10 minutes the mixture was mixed well by a homogenizer probe with set 3 on PowerGen 1000 homogenizer until a uniform suspension was obtained.

The in vitro release behavior of the aripiprazole formulations was characterized as follows. Aripiprazole suspension formulation (0.05 mL) was dispensed and weighed into a 50 mL, conical bottom, polypropylene tube with screw cap (Falcon tubes). Then, 50 mL of 0.01N HCl buffered at pH 4.5 and pre-equilibrated to 37° C., was added to each vial and the vials capped. The release study was conducted in quadruplicate for each formulation in a Jeol Tech Orbital Shaker at 37° C. set to 100 rpm. At each time point, 50 mL of the release medium was removed (without disrupting the formulation) and replaced with new medium. The solution was either diluted with 50% ammonium acetate:30% acetonitrile:20% Methanol or directly transferred to HPLC vial for analysis. Aripiprazole release was monitored for 22 days. Formulation remaining in the release medium at the end of the release experiment was extracted using EtOAc to establish mass balance.

Figure 41:
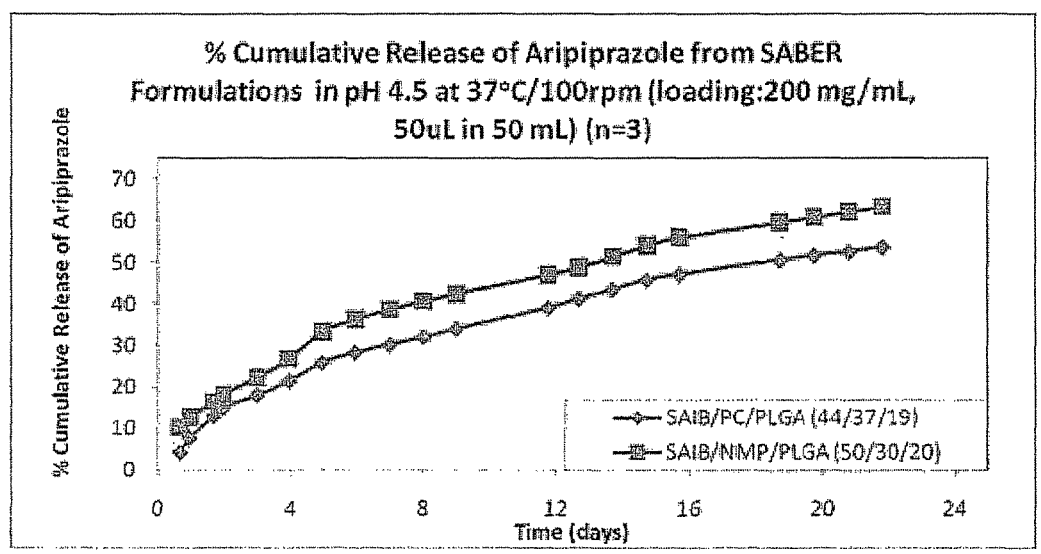
FIG. 41 shows release profiles from compositions comprising aripiprazole, sucrose acetate isobutyrate, solvent (N-methylpyrrolidone or propylene carbonate), and poly (lactic acid)(glycolic acid) initiated with dodecanol.

The release profiles from the formulations are shown in FIG. 41. This FIG. shows aripiprazole release for at least 22 days.

In addition, other aripiprazole formulations were tested in vitro. Aripiprazole (30 mg/mL) in 68/32 SAIB/BA, tested in 100 mL of PBS @ pH 6+1% SDS, resulted in 98% release at 48 hours. Aripiprazole (40 mg/mL) in 72/28 SAIB/NMP, tested in 100 mL of PBS @ pH 6+1% SDS, resulted in 91% release at 48 hours. Aripiprazole (197 mg/mL) in 44/37/19 SAIB/PC/PLGA in 100 mL of PBS @ pH 6+1% SDS, resulted in 73% release at 122 hours. Aripiprazole (197 mg/mL) in 44/37/19 SAIB/PC/PLGA in 400 mL of PBS @ pH 6+no SDS, resulted in 1% release at 122 hours. Aripiprazole (197 mg/mL) in 50/30/20 SAIB/NMP/PLGA in 100 mL of PBS @ pH 6+1% SDS, resulted in 55% release at 122 hours. Aripiprazole (197 mg/mL) in 50/30/20 SAIB/NMP/PLGA in 400 mL of PBS @ pH 6+no SDS, resulted in ≥1% release at 122 hours. These results indicate that the release is significantly affected by the presence or absence of SDS in the in vitro release media.

The foregoing embodiments and advantages are merely exemplary and are not to be construed as limiting the present disclosure. The description of the present disclosure is intended to be illustrative, and not to limit the scope of the claims. Many alternatives, modifications, and variations will be apparent to those skilled in the art.

Having now fully described this disclosure, it will be understood to those of ordinary skill in the art that the methods of the present disclosure can be carried out with a wide and equivalent range of conditions, formulations, and other parameters without departing from the scope of the disclosure or any embodiments thereof.

All patents and publications cited herein are hereby fully incorporated by reference in their entirety. The citation of any publication is for its disclosure prior to the filing date and should not be construed as an admission that such publication is prior art or that the present disclosure is not entitled to antedate such publication by virtue of prior acts of invention.

What is claimed is:
1. A composition comprising:
a pharmaceutical active agent;
25 wt % to 80 wt %, based on total weight of the composition, of a non-polymeric, non-water soluble high viscosity liquid carrier material (HVLCM) having a viscosity of at least 5000 cP at 37° C. that does not crystallize neat at 25° C. and 1 atmosphere;
a lactic acid-based polymer comprising an alkoxy end group having 8 to 24 carbons, the lactic acid-based polymer having a lactic acid to glycolic acid molar ratio ranging from 100:0 to 40:60; and
an organic solvent comprising at least one member selected from N-methyl-pyrrolidone, dimethylsulfoxide, propylene carbonate, and benzyl benzoate.

2. The composition of claim 1, wherein the lactic-acid based polymer has a weight average molecular weight ranging from 1000 Daltons to 30,000 Daltons.

3. The composition of claim 1, wherein the pharmaceutical active agent comprises at least one member selected from peptide, protein, and small molecule.

4. The composition of claim 1, wherein the pharmaceutical active agent comprises risperidone or pharmaceutically acceptable salt thereof.

5. The composition of claim 1, wherein the pharmaceutical active agent comprises particles having a median particle size, as measured by laser diffraction, ranging from 0.5 micrometer to 10 micrometers.

6. The composition of claim 1, wherein the HVLCM comprises sucrose acetate isobutyrate.

7. The composition of claim 1, wherein the solvent comprises at least one member selected from N-methyl-pyrrolidone, dimethylsulfoxide, and propylene carbonate.

8. The composition of claim 1, wherein the composition has a viscosity of less than 3000 cP at a shear rate of 100 $s^{-1}$ at 25° C.

9. The composition of claim 1, wherein the composition has been irradiated with a sufficient amount of gamma irradiation to sterilize the composition.

10. The composition of claim 2, wherein the pharmaceutical active agent comprises at least one member selected from peptide, protein, and small molecule.

11. The composition of claim 10, wherein the pharmaceutical active agent comprises particles having a median particle size, as measured by laser diffraction, ranging from 0.5 micrometer to 10 micrometers.

12. The composition of claim 11, wherein the HVLCM comprises sucrose acetate isobutyrate.

13. The composition of claim 11, wherein the solvent comprises at least one member selected from N-methyl-pyrrolidone, dimethylsulfoxide, and propylene carbonate.

14. The composition of claim 12, wherein the solvent comprises at least one member selected from N-methyl-pyrrolidone, dimethylsulfoxide, and propylene carbonate.

15. The composition of claim 14, wherein the composition has a viscosity of less than 3000 cP at a shear rate of 100 $s^{-1}$ at 25° C.

16. The composition of claim 11, wherein the composition has been irradiated with a sufficient amount of gamma irradiation to sterilize the composition.

17. The composition of claim 1, wherein the lactic acid based-polymer is poly(lactic acid)(glycolic acid) having a lactic acid to glycolic acid molar ratio ranging from 95:5 to 60:40.

18. The composition of claim 2, wherein the lactic acid based-polymer is poly(lactic acid)(glycolic acid) having a lactic acid to glycolic acid molar ratio ranging from 95:5 to 60:40.

19. The composition of claim 7, wherein the lactic acid based-polymer is poly(lactic acid)(glycolic acid) having a lactic acid to glycolic acid molar ratio ranging from 95:5 to 60:40.

20. A composition comprising:
- 0.5 wt % to 50 wt %, based on total weight of the composition, of particles comprising a pharmaceutical active agent;
- 10 wt % to 60 wt %, based on total weight of the composition, of sucrose acetate isobutyrate;
- 1 wt % to 30 wt %, based on total weight of the composition, of a lactic acid-based polymer comprising an alkoxy end group having 8 to 24 carbons, the lactic acid-based polymer having a lactic acid to glycolic acid molar ratio ranging from 100:0 to 40:60, the lactic acid-based polymer having a weight average molecular weight ranging from 4000 Daltons to 30,000 Daltons; and
- 10 wt % to 50 wt %, based on total weight of the composition, of an organic solvent comprising at least one member selected from N-methyl-pyrrolidone, dimethylsulfoxide, propylene carbonate, and benzyl benzoate.

* * * * *